United States Patent
Thorne et al.

(10) Patent No.: US 11,253,559 B2
(45) Date of Patent: Feb. 22, 2022

(54) ONCOLYTIC VIRUSES TARGETING STAT3

(71) Applicant: UNIVERSITY OF PITTSBURGH—OF THE COMMONWEALTH SYSTEM OF HIGHER EDUCATION, Pittsburgh, PA (US)

(72) Inventors: Stephen Howard Thorne, Pittsburgh, PA (US); Daniel J. Byrd, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 12 days.

(21) Appl. No.: 16/252,338

(22) Filed: Jan. 18, 2019

(65) Prior Publication Data

US 2019/0142883 A1 May 16, 2019

Related U.S. Application Data

(63) Continuation of application No. PCT/US2017/042910, filed on Jul. 19, 2017.

(60) Provisional application No. 62/364,095, filed on Jul. 19, 2016.

(51) Int. Cl.
| | |
|---|---|
| *A61K 35/768* | (2015.01) |
| *A61P 35/00* | (2006.01) |
| *A61K 9/00* | (2006.01) |
| *C07K 14/07* | (2006.01) |
| *C07K 14/16* | (2006.01) |
| *C07K 14/47* | (2006.01) |
| *C12N 15/62* | (2006.01) |
| *C12N 9/16* | (2006.01) |
| *C12N 9/10* | (2006.01) |
| *C12N 1/10* | (2006.01) |
| *C07K 16/28* | (2006.01) |

(52) U.S. Cl.
CPC .......... *A61K 35/768* (2013.01); *A61K 9/0019* (2013.01); *A61P 35/00* (2018.01); *C07K 14/07* (2013.01); *C07K 14/16* (2013.01); *C07K 14/4702* (2013.01); *C12N 9/104* (2013.01); *C12N 9/16* (2013.01); *C12N 15/625* (2013.01); *C12Y 301/03048* (2013.01); *C07K 16/2827* (2013.01); *C12N 2710/24132* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 5,399,363 | A | 3/1995 | Liversidge et al. |
| 5,543,158 | A | 8/1996 | Gref et al. |
| 5,641,515 | A | 6/1997 | Ramtoola |
| 6,506,559 | B1 | 1/2003 | Fire et al. |
| 6,573,099 | B2 | 6/2003 | Graham |
| 2003/0083249 | A1* | 5/2003 | Brown ............... C07K 14/4702 514/17.4 |
| 2004/0248787 | A1 | 12/2004 | Naito et al. |
| 2013/0202577 | A1* | 8/2013 | Tiganis ................ C12Q 1/6886 424/94.6 |
| 2016/0060311 | A1 | 3/2016 | Jo et al. |
| 2016/0152678 | A1 | 6/2016 | Bancel et al. |

FOREIGN PATENT DOCUMENTS

| | | | |
|---|---|---|---|
| CN | 101381742 A | | 3/2009 |
| CN | 102796709 A | * | 11/2012 |
| CN | 103614416 B | * | 9/2016 |
| JP | 2016-512199 A | | 4/2016 |
| WO | WO 1999/032619 A1 | | 7/1999 |
| WO | WO 2001/036646 A1 | | 5/2001 |
| WO | WO 2001/068836 A2 | | 9/2001 |
| WO | WO-2011098806 A1 | * | 8/2011 .............. A61P 31/22 |
| WO | WO 2011/110359 A1 | | 9/2011 |
| WO | WO-2014185973 A2 | * | 11/2014 ......... A61K 31/5377 |
| WO | WO 2015/027163 A1 | | 2/2015 |
| WO | WO-2015184061 A2 | * | 12/2015 ....... A61K 39/39558 |

OTHER PUBLICATIONS

Borrelli et al., Molecules, 2018, 23:295. (Year: 2018).*
Yagil et al., Trends in Immunology, Feb. 22, 2010, 31(5):199-204. (Year: 2010).*
Anonymous: "Combining STAT3-Silencing and Oncolytic Vaccinia Virus to Enhance Anti-Tumor Therapeutic Activity," Project Information—1F32CA199981-01A1, (Mar. 7, 2016).
Duval et al., "The 'PINIT' motif, of a newly identified conserved domain of the PIAS protein family, is essential for nuclear retention of PIAS3L," FEBS Letters 554:111-118 (2003).
Lv et al., "Oncolytic vaccine virus harbouring the *IL-24* gene suppresses the growth of lung cancer by inducing apoptosis," Biochemical and Biophysical Research Communications 476:21-28 (2016).

(Continued)

*Primary Examiner* — Nicole Kinsey White
(74) *Attorney, Agent, or Firm* — Baker Botts L.L.P.

(57) ABSTRACT

This disclosure relates to modified viruses, e.g., oncolytic vaccinia viruses, which have been modified to contain an exogenous nucleic acid that expresses a protein that modulates STAT3 activity. It is based, at least in part, on the discovery that vaccinia viruses modified to contain nucleic acid encoding PIAS3 and that express PIAS3 or a fragment thereof can inhibit STAT3 activity and enhance the anti-cancer activity of the vaccinia virus. Accordingly, this disclosure provides for oncolytic vaccinia viruses and methods of using them in the treatment of cancers.

20 Claims, 9 Drawing Sheets

Specification includes a Sequence Listing.

(56) References Cited

OTHER PUBLICATIONS

Mautsa et al., "The PINIT domain of PIAS3: structure-function analysis of its interaction with STAT3," Journal of Molecular Recognition 24:795-803 (2011).
Ogata et al., "Overexpression of PIAS3 Suppresses Cell Growth, Restores the Drug Sensitivity of Human Lung Cancer Cells in Association with PI3-K/Akt Inactivation," Neoplasia 8(10):817-825 (2006).
Supplementary Partial European Search Report dated Feb. 18, 2020 in Application No. EP 17831813.
Alcami et al., "A Soluble Receptor for Interleukin-1β Encoded by Vaccinia Virus: A Novel Mechanism of Virus Modulation of the Host Response to Infection," Cell 71:153-167 (1992).
Altschul et al., "Gapped BLAST and PSI-BLAST: a new generation of protein database search programs," Nucleic Acids Res., 25(17):3389-3402 (1997).
Bu et al., "GRIM-19 inhibits the STAT3 signaling pathway and sensitizes gastric cancer cells to radiation," Gene 512:198-205 (2013).
Carpenter et al., "STAT3 Target Genes Relevant to Human Cancers," Cancers, 6:897-925 (2014).
Chartier et al., "Efficient Generation of Recombinant Adenovirus Vectors by Homologous Recombinationin *Escherichia coli*,", J. Virol 70(7):4805-4810 (1996).
Colamonici et al., "Vaccinia Virus B18R Gene Encodes a Type I Interferon-binding Protein That Blocks Interferon a Transmembrane Signaling," J. Biol. Chem. 270(27):15974-15978 (1995).
Fahy et al., "Vaccinia virus protein C16 acts intracellularly to modulate the host response and promote virulence," J. Gen. Virol. 89:2377-2387 (2008).
Furtek et al., "Strategies and Approaches of Targeting STAT3 for Cancer Treatment," ACS Chem. Biol. 11:308-318 (2016).
International Search Report dated Mar. 6, 2018 in International Application No. PCT/US17/42910.
Karlin et al., "Applications and statistics for multiple high-scoring segments in molecular sequences," PNAS USA, 90:5873-5877 (1993).
Kirn et al., "Targeted and armed oncolytic poxviruses: a novel multi-mechanistic therapeutic class for cancer," Nat Rev Cancer 9:64-71 (2009).
Paul et al., "Tumor gene therapy by MVA-mediated expression of T-cell—stimulating antibodies," Cancer Gene Ther. 9:470-477 (2002).
Siveen et al., "Targeting the STAT3 signaling pathway in cancer: Role of synthetic and natural inhibitors," Biochimica et Biophysica Acta 1845:136-154 (2014).
Symons et al., "Vaccinia Virus Encodes a Soluble Type I Interferon Receptor of Novel Structure and Broad Species Specificity," Cell 81:551-560 (1995).
Yue et al., "Targeting STAT3 in cancer: how successful are we?" Expert Opin. Investig. Drugs 18(1):45-56 (2009).
Naoki Kajiwara et al., "Cell penetrating peptide," Journal of Japanese Pharmacology 141:220-221 (2013) [with English machine translation].
Sampath et al., "Crosstalk between Immune Cell and Oncolytic Vaccinia Therapy Enhances Tumor Trafficking and Antitumor Effects," Mol. Ther., 21(3):620-628 (2013).
Shields et al., "TCPTP Regulates SFK and STAT3 Signaling and Is Lost in Triple-Negative Breast Cancers," Mol. Cell Biol., 33(3):557-570 (2013).

\* cited by examiner

SEQUENCE LISTING

<160> NUMBER OF SEQ ID NOS: 43

<210> SEQ ID NO 1
<211> LENGTH: 628
<212> TYPE: PRT
<213> ORGANISM: Homo sapiens

<400> SEQUENCE: 1

Met Ala Glu Leu Gly Glu Leu Lys His Met Val Met Ser Phe Arg Val
1               5                   10                  15

Ser Glu Leu Gln Val Leu Leu Gly Phe Ala Gly Arg Asn Lys Ser Gly
                20                  25                  30

Arg Lys His Glu Leu Leu Ala Lys Ala Leu His Leu Leu Lys Ser Ser
            35                  40                  45

Cys Ala Pro Ser Val Gln Met Lys Ile Lys Glu Leu Tyr Arg Arg Arg
        50                  55                  60

Phe Pro Arg Lys Thr Leu Gly Pro Ser Asp Leu Ser Leu Leu Ser Leu
65                  70                  75                  80

Pro Pro Gly Thr Ser Pro Val Gly Ser Pro Gly Pro Leu Ala Pro Ile
                85                  90                  95

Pro Pro Thr Leu Leu Ala Pro Gly Thr Leu Leu Gly Pro Lys Arg Glu
            100                 105                 110

Val Asp Met His Pro Pro Leu Pro Gln Pro Val His Pro Asp Val Thr
        115                 120                 125

Met Lys Pro Leu Pro Phe Tyr Glu Val Tyr Gly Glu Leu Ile Arg Pro
    130                 135                 140

Thr Thr Leu Ala Ser Thr Ser Ser Gln Arg Phe Glu Glu Ala His Phe
145                 150                 155                 160

Thr Phe Ala Leu Thr Pro Gln Gln Val Gln Gln Ile Leu Thr Ser Arg
                165                 170                 175

Glu Val Leu Pro Gly Ala Lys Cys Asp Tyr Thr Ile Gln Val Gln Leu
            180                 185                 190

Arg Phe Cys Leu Cys Glu Thr Ser Cys Pro Gln Glu Asp Tyr Phe Pro
        195                 200                 205

Pro Asn Leu Phe Val Lys Val Asn Gly Lys Leu Cys Pro Leu Pro Gly
    210                 215                 220

Tyr Leu Pro Pro Thr Lys Asn Gly Ala Glu Pro Lys Arg Pro Ser Arg
225                 230                 235                 240

Pro Ile Asn Ile Thr Pro Leu Ala Arg Leu Ser Ala Thr Val Pro Asn
                245                 250                 255

Thr Ile Val Val Asn Trp Ser Ser Glu Phe Gly Arg Asn Tyr Ser Leu
            260                 265                 270

Ser Val Tyr Leu Val Arg Gln Leu Thr Ala Gly Thr Leu Leu Gln Lys
        275                 280                 285

Leu Arg Ala Lys Gly Ile Arg Asn Pro Asp His Ser Arg Ala Leu Ile
    290                 295                 300

Lys Glu Lys Leu Thr Ala Asp Pro Asp Ser Glu Val Ala Thr Thr Ser
305                 310                 315                 320

Leu Arg Val Ser Leu Met Cys Pro Leu Gly Lys Met Arg Leu Thr Val
                325                 330                 335

Pro Cys Arg Ala Leu Thr Cys Ala His Leu Gln Ser Phe Asp Ala Ala
            340                 345                 350

Leu Tyr Leu Gln Met Asn Glu Lys Lys Pro Thr Trp Thr Cys Pro Val
        355                 360                 365

```
Cys Asp Lys Lys Ala Pro Tyr Glu Ser Leu Ile Ile Asp Gly Leu Phe
    370                 375                 380

Met Glu Ile Leu Ser Ser Cys Ser Asp Cys Asp Glu Ile Gln Phe Met
385                 390                 395                 400

Glu Asp Gly Ser Trp Cys Pro Met Lys Pro Lys Lys Glu Ala Ser Glu
                405                 410                 415

Val Cys Pro Pro Gly Tyr Gly Leu Asp Gly Leu Gln Tyr Ser Pro
            420                 425                 430

Val Gln Gly Gly Asp Pro Ser Glu Asn Lys Lys Lys Val Glu Val Ile
            435                 440                 445

Asp Leu Thr Ile Glu Ser Ser Asp Glu Gly Asp Leu Pro Pro Thr
450                 455                 460

Lys Lys His Cys Ser Val Thr Ser Ala Ala Ile Pro Ala Leu Pro Gly
465                 470                 475                 480

Ser Lys Gly Val Leu Thr Ser Gly His Gln Pro Ser Ser Val Leu Arg
                485                 490                 495

Ser Pro Ala Met Gly Thr Leu Gly Gly Asp Phe Leu Ser Ser Leu Pro
                500                 505                 510

Leu His Glu Tyr Pro Pro Ala Phe Pro Leu Gly Ala Asp Ile Gln Gly
        515                 520                 525

Leu Asp Leu Phe Ser Phe Leu Gln Thr Glu Ser Gln His Tyr Gly Pro
        530                 535                 540

Ser Val Ile Thr Ser Leu Asp Glu Gln Asp Ala Leu Gly His Phe Phe
545                 550                 555                 560

Gln Tyr Arg Gly Thr Pro Ser His Phe Leu Gly Pro Leu Ala Pro Thr
                565                 570                 575

Leu Gly Ser Ser His Cys Ser Ala Thr Pro Ala Pro Pro Gly Arg
                580                 585                 590

Val Ser Ser Ile Val Ala Pro Gly Gly Ala Leu Arg Glu Gly His Gly
            595                 600                 605

Gly Pro Leu Pro Ser Gly Pro Ser Leu Thr Gly Cys Arg Ser Asp Ile
        610                 615                 620

Ile Ser Leu Asp
625

<210> SEQ ID NO 2
<211> LENGTH: 184
<212> TYPE: PRT
<213> ORGANISM: Homo sapiens

<400> SEQUENCE: 2

Pro Phe Tyr Glu Val Tyr Gly Glu Leu Ile Arg Pro Thr Thr Leu Ala
1               5                   10                  15

Ser Thr Ser Ser Gln Arg Phe Glu Glu Ala His Phe Thr Phe Ala Leu
                20                  25                  30

Thr Pro Gln Gln Val Gln Gln Ile Leu Thr Ser Arg Glu Val Leu Pro
            35                  40                  45

Gly Ala Lys Cys Asp Tyr Thr Ile Gln Val Gln Leu Arg Phe Cys Leu
    50                  55                  60

Cys Glu Thr Ser Cys Pro Gln Glu Asp Tyr Phe Pro Pro Asn Leu Phe
65                  70                  75                  80

Val Lys Val Asn Gly Lys Leu Cys Pro Leu Pro Gly Tyr Leu Pro Pro
                85                  90                  95

Thr Lys Asn Gly Ala Glu Pro Lys Arg Pro Ser Arg Pro Ile Asn Ile
                100                 105                 110
```

```
Thr Pro Leu Ala Arg Leu Ser Ala Thr Val Pro Asn Thr Ile Val Val
        115                 120                 125

Asn Trp Ser Ser Glu Phe Gly Arg Asn Tyr Ser Leu Ser Val Tyr Leu
130                 135                 140

Val Arg Gln Leu Thr Ala Gly Thr Leu Leu Gln Lys Leu Arg Ala Lys
145                 150                 155                 160

Gly Ile Arg Asn Pro Asp His Ser Arg Ala Leu Ile Lys Glu Lys Leu
        165                 170                 175

Thr Ala Asp Pro Asp Ser Glu Val
        180

<210> SEQ ID NO 3
<211> LENGTH: 46
<212> TYPE: PRT
<213> ORGANISM: Homo sapiens

<400> SEQUENCE: 3

Leu Pro Phe Tyr Glu Val Tyr Gly Glu Leu Ile Arg Pro Thr Thr Leu
1               5                   10                  15

Ala Ser Thr Ser Ser Gln Arg Phe Glu Glu Ala His Phe Thr Phe Ala
            20                  25                  30

Leu Thr Pro Gln Gln Val Gln Gln Ile Leu Thr Ser Arg Glu
        35                  40                  45

<210> SEQ ID NO 4
<211> LENGTH: 51
<212> TYPE: PRT
<213> ORGANISM: Homo sapiens

<400> SEQUENCE: 4

Asp Val Thr Met Lys Pro Leu Pro Phe Tyr Glu Val Tyr Gly Glu Leu
1               5                   10                  15

Ile Arg Pro Thr Thr Leu Ala Ser Thr Ser Ser Gln Arg Phe Glu Glu
            20                  25                  30

Ala His Phe Thr Phe Ala Leu Thr Pro Gln Gln Val Gln Gln Ile Leu
        35                  40                  45

Thr Ser Arg
    50

<210> SEQ ID NO 5
<211> LENGTH: 188
<212> TYPE: PRT
<213> ORGANISM: Homo sapiens

<400> SEQUENCE: 5

Met Lys Pro Leu Pro Phe Tyr Glu Val Tyr Gly Glu Leu Ile Arg Pro
1               5                   10                  15

Thr Thr Leu Ala Ser Thr Ser Ser Gln Arg Phe Glu Glu Ala His Phe
            20                  25                  30

Thr Phe Ala Leu Thr Pro Gln Gln Val Gln Gln Ile Leu Thr Ser Arg
        35                  40                  45

Glu Val Leu Pro Gly Ala Lys Cys Asp Tyr Thr Ile Gln Val Gln Leu
50                  55                  60

Arg Phe Cys Leu Cys Glu Thr Ser Cys Pro Gln Glu Asp Tyr Phe Pro
65                  70                  75                  80

Pro Asn Leu Phe Val Lys Val Asn Gly Lys Leu Cys Pro Leu Pro Gly
            85                  90                  95
```

```
Tyr Leu Pro Pro Thr Lys Asn Gly Ala Glu Pro Lys Arg Pro Ser Arg
            100                 105                 110

Pro Ile Asn Ile Thr Pro Leu Ala Arg Leu Ser Ala Thr Val Pro Asn
        115                 120                 125

Thr Ile Val Val Asn Trp Ser Ser Glu Phe Gly Arg Asn Tyr Ser Leu
    130                 135                 140

Ser Val Tyr Leu Val Arg Gln Leu Thr Ala Gly Thr Leu Leu Gln Lys
145                 150                 155                 160

Leu Arg Ala Lys Gly Ile Arg Asn Pro Asp His Ser Arg Ala Leu Ile
                165                 170                 175

Lys Glu Lys Leu Thr Ala Asp Pro Asp Ser Glu Val
            180                 185

<210> SEQ ID NO 6
<211> LENGTH: 628
<212> TYPE: PRT
<213> ORGANISM: Mus musculus

<400> SEQUENCE: 6

Met Ala Glu Leu Gly Glu Leu Lys His Met Val Met Ser Phe Arg Val
1               5                   10                  15

Ser Glu Leu Gln Val Leu Leu Gly Phe Ala Gly Arg Asn Lys Ser Gly
            20                  25                  30

Arg Lys His Glu Leu Leu Ala Lys Ala Leu His Leu Leu Lys Ser Ser
        35                  40                  45

Cys Ala Pro Ser Val Gln Met Lys Ile Lys Glu Leu Tyr Arg Arg Arg
    50                  55                  60

Phe Pro Arg Lys Thr Leu Gly Pro Ser Asp Leu Ser Leu Leu Ser Leu
65                  70                  75                  80

Pro Pro Gly Thr Ser Pro Val Gly Ser Pro Gly Pro Leu Ala Pro Ile
                85                  90                  95

Pro Pro Thr Leu Leu Thr Pro Gly Thr Leu Leu Gly Pro Lys Arg Glu
            100                 105                 110

Val Asp Met His Pro Pro Leu Pro Gln Pro Val His Pro Asp Val Thr
        115                 120                 125

Met Lys Pro Leu Pro Phe Tyr Glu Val Tyr Gly Glu Leu Ile Arg Pro
    130                 135                 140

Thr Thr Leu Ala Ser Thr Ser Ser Gln Arg Phe Glu Glu Ala His Phe
145                 150                 155                 160

Thr Phe Ala Leu Thr Pro Gln Gln Leu Gln Gln Ile Leu Thr Ser Arg
                165                 170                 175

Glu Val Leu Pro Gly Ala Lys Cys Asp Tyr Thr Ile Gln Val Gln Leu
            180                 185                 190

Arg Phe Cys Leu Cys Glu Thr Ser Cys Pro Gln Glu Asp Tyr Phe Pro
        195                 200                 205

Pro Asn Leu Phe Val Lys Val Asn Gly Lys Leu Cys Pro Leu Pro Gly
    210                 215                 220

Tyr Leu Pro Pro Thr Lys Asn Gly Ala Glu Pro Lys Arg Pro Ser Arg
225                 230                 235                 240

Pro Ile Asn Ile Thr Pro Leu Ala Arg Leu Ser Ala Thr Val Pro Asn
                245                 250                 255

Thr Ile Val Val Asn Trp Ser Ser Glu Phe Gly Arg Asn Tyr Ser Leu
            260                 265                 270

Ser Val Tyr Leu Val Arg Gln Leu Thr Ala Gly Thr Leu Leu Gln Lys
        275                 280                 285
```

Leu Arg Ala Lys Gly Ile Arg Asn Pro Asp His Ser Arg Ala Leu Ile
            290                 295                 300

Lys Glu Lys Leu Thr Ala Asp Pro Asp Ser Glu Val Ala Thr Thr Ser
305                 310                 315                 320

Leu Arg Val Ser Leu Met Cys Pro Leu Gly Lys Met Arg Leu Thr Val
                325                 330                 335

Pro Cys Arg Ala Leu Thr Cys Ala His Leu Gln Ser Phe Asp Ala Ala
            340                 345                 350

Leu Tyr Leu Gln Met Asn Glu Lys Lys Pro Thr Trp Thr Cys Pro Val
        355                 360                 365

Cys Asp Lys Lys Ala Pro Tyr Glu Ser Leu Ile Ile Asp Gly Leu Phe
    370                 375                 380

Met Glu Ile Leu Asn Ser Cys Ser Asp Cys Asp Glu Ile Gln Phe Met
385                 390                 395                 400

Glu Asp Gly Ser Trp Cys Pro Met Lys Pro Lys Lys Glu Ala Ser Glu
                405                 410                 415

Val Cys Pro Pro Pro Gly Tyr Gly Leu Asp Gly Leu Gln Tyr Ser Ala
            420                 425                 430

Val Gln Glu Gly Ile Gln Pro Glu Ser Lys Lys Arg Val Glu Val Ile
        435                 440                 445

Asp Leu Thr Ile Glu Ser Ser Ser Asp Glu Glu Asp Leu Pro Pro Thr
    450                 455                 460

Lys His Cys Pro Val Thr Ser Ala Ala Ile Pro Ala Leu Pro Gly
465                 470                 475                 480

Ser Lys Gly Ala Leu Thr Ser Gly His Gln Pro Ser Ser Val Leu Arg
                485                 490                 495

Ser Pro Ala Met Gly Thr Leu Gly Ser Asp Phe Leu Ser Ser Leu Pro
            500                 505                 510

Leu His Glu Tyr Pro Pro Ala Phe Pro Leu Gly Ala Asp Ile Gln Gly
        515                 520                 525

Leu Asp Leu Phe Ser Phe Leu Gln Thr Glu Ser Gln His Tyr Gly Pro
    530                 535                 540

Ser Val Ile Thr Ser Leu Asp Glu Gln Asp Thr Leu Gly His Phe Phe
545                 550                 555                 560

Gln Tyr Arg Gly Thr Pro Ser His Phe Leu Gly Pro Leu Ala Pro Thr
                565                 570                 575

Leu Gly Ser Ser His Arg Ser Thr Pro Ala Pro Pro Gly Arg
            580                 585                 590

Val Ser Ser Ile Val Ala Pro Gly Ser Ser Leu Arg Glu Gly His Gly
        595                 600                 605

Gly Pro Leu Pro Ser Gly Pro Ser Leu Thr Gly Cys Arg Ser Asp Val
    610                 615                 620

Ile Ser Leu Asp
625

<210> SEQ ID NO 7
<211> LENGTH: 628
<212> TYPE: PRT
<213> ORGANISM: Rattus norvegicus

<400> SEQUENCE: 7

Met Ala Glu Leu Gly Glu Leu Lys His Met Val Met Ser Phe Arg Val
1               5                   10                  15

Ser Glu Leu Gln Val Leu Leu Gly Phe Ala Gly Arg Asn Lys Ser Gly

-continued

```
            20                  25                  30
Arg Lys His Glu Leu Leu Ala Lys Ala Leu His Leu Leu Lys Ser Ser
        35                  40                  45
Cys Ala Pro Ser Val Gln Met Lys Ile Lys Glu Leu Tyr Arg Arg Arg
    50                  55                  60
Phe Pro Arg Lys Thr Leu Gly Pro Ser Asp Leu Ser Leu Leu Ser Leu
65                  70                  75                  80
Pro Pro Gly Thr Ser Pro Val Gly Ser Pro Ser Pro Leu Ala Ser Ile
                85                  90                  95
Pro Pro Thr Leu Leu Thr Pro Gly Thr Leu Leu Gly Pro Lys Arg Glu
            100                 105                 110
Val Asp Met His Pro Pro Leu Pro Gln Pro Val His Pro Asp Val Thr
                115                 120                 125
Met Lys Pro Leu Pro Phe Tyr Glu Val Tyr Gly Glu Leu Ile Arg Pro
            130                 135                 140
Thr Thr Leu Ala Ser Thr Ser Ser Gln Arg Phe Glu Glu Ala His Phe
145                 150                 155                 160
Thr Phe Ala Leu Thr Pro Gln Gln Leu Gln Gln Ile Leu Thr Ser Arg
                165                 170                 175
Glu Val Leu Pro Gly Ala Lys Cys Asp Tyr Thr Ile Gln Val Gln Leu
            180                 185                 190
Arg Phe Cys Leu Cys Glu Thr Ser Cys Pro Gln Glu Asp Tyr Phe Pro
        195                 200                 205
Pro Asn Leu Phe Val Lys Val Asn Gly Lys Leu Cys Pro Leu Pro Gly
    210                 215                 220
Tyr Leu Pro Pro Thr Lys Asn Gly Ala Glu Pro Lys Arg Pro Ser Arg
225                 230                 235                 240
Pro Ile Asn Ile Thr Pro Leu Ala Arg Leu Ser Ala Thr Val Pro Asn
                245                 250                 255
Thr Ile Val Val Asn Trp Ser Ser Glu Phe Gly Arg Asn Tyr Ser Leu
            260                 265                 270
Ser Val Tyr Leu Val Arg Gln Leu Thr Ala Gly Thr Leu Leu Gln Lys
        275                 280                 285
Leu Arg Ala Lys Gly Ile Arg Asn Pro Asp His Ser Arg Ala Leu Ile
    290                 295                 300
Lys Glu Lys Leu Thr Ala Asp Pro Asp Ser Glu Val Ala Thr Thr Ser
305                 310                 315                 320
Leu Arg Val Ser Leu Met Cys Pro Leu Gly Lys Met Arg Leu Thr Val
                325                 330                 335
Pro Cys Arg Ala Leu Thr Cys Ala His Leu Gln Ser Phe Asp Ala Ala
            340                 345                 350
Leu Tyr Leu Gln Met Asn Glu Lys Lys Pro Thr Trp Thr Cys Pro Val
        355                 360                 365
Cys Asp Lys Lys Ala Pro Tyr Glu Ser Leu Ile Ile Asp Gly Leu Phe
    370                 375                 380
Met Glu Ile Leu Asn Ser Cys Ser Asp Cys Asp Glu Ile Gln Phe Met
385                 390                 395                 400
Glu Asp Gly Ser Trp Cys Pro Met Lys Pro Lys Lys Glu Ala Ser Glu
                405                 410                 415
Val Cys Pro Pro Pro Gly Tyr Gly Leu Asp Gly Leu Gln Tyr Ser Pro
            420                 425                 430
Val Gln Glu Gly Asn Gln Ser Glu Asn Lys Lys Arg Val Glu Val Ile
        435                 440                 445
```

```
Asp Leu Thr Ile Glu Ser Ser Ser Asp Glu Glu Asp Leu Pro Pro Thr
450                 455                 460

Lys Lys His Cys Pro Val Thr Ser Ala Ala Ile Pro Ala Leu Pro Gly
465                 470                 475                 480

Ser Lys Gly Ala Leu Thr Ser Gly His Gln Pro Ser Ser Val Leu Arg
            485                 490                 495

Ser Pro Ala Met Gly Thr Leu Gly Ser Asp Phe Leu Ser Ser Leu Pro
                500                 505                 510

Leu His Glu Tyr Pro Pro Ala Phe Pro Leu Gly Ala Asp Ile Gln Gly
        515                 520                 525

Leu Asp Leu Phe Ser Phe Leu Gln Thr Glu Ser Gln His Tyr Ser Pro
530                 535                 540

Ser Val Ile Thr Ser Leu Asp Glu Gln Asp Thr Leu Gly His Phe Phe
545                 550                 555                 560

Gln Phe Arg Gly Thr Pro Pro His Phe Leu Gly Pro Leu Ala Pro Thr
                565                 570                 575

Leu Gly Ser Ser His Arg Ser Ala Thr Pro Ala Pro Ala Pro Gly Arg
            580                 585                 590

Val Ser Ser Ile Val Ala Pro Gly Ser Ser Leu Arg Glu Gly His Gly
            595                 600                 605

Gly Pro Leu Pro Ser Gly Pro Ser Leu Thr Gly Cys Arg Ser Asp Val
610                 615                 620

Ile Ser Leu Asp
625

<210> SEQ ID NO 8
<211> LENGTH: 1887
<212> TYPE: DNA
<213> ORGANISM: Homo sapiens

<400> SEQUENCE: 8
atggcggagc tgggcgaatt aaagcacatg gtgatgagtt tccgggtgtc tgagctccag      60
gtgcttcttg gctttgctgg ccggaacaag agtggacgga agcacgagct cctggccaag     120
gctctgcacc tcctgaagtc cagctgtgcc cctagtgtcc agatgaagat caaagagctt     180
taccgacgac gctttccccg gaagaccctg ggccctctg atctctccct tctctctttg      240 cccccctggca cctctcctgt aggctcccct ggtcctctag ctcccattcc ccaacgctg     300 ttggccccctg caccctgct gggccccaag cgtgaggtgg acatgcaccc cctctgccc     360 cagcctgtgc accctgatgt caccatgaaa ccattgccct ctatgaagt ctatggggag     420 ctcatccggc caccaccct tgcatccact tctagccagc ggtttgagga gcgcactt      480 acctttgccc tcacacccca gcaagtgcag cagattctta catccagaga ggttctgcca     540
ggagccaaat gtgattatac catacaggtg cagctaaggt tctgtctctg tgagaccagc     600 tgccccccagg aagattattt tccccccaac ctctttgtca aggtcaatgg aaactgtgc     660 cccctgccgg gttaccttcc cccaaccaag aatggggccg agcccaagag gcccagccgc     720
cccatcaaca tcacacccct ggctcgactc tcagccactg ttcccaacac cattgtggtc     780
aattggtcat ctgagttcgg acggaattac tccttgtctg tgtacctggt gaggcagttg     840
actgcaggaa cccttctaca aaaactcaga gcaaaggta tccggaaccc agaccactcg     900
cgggcactga tcaaggagaa attgactgct gaccctgaca gtgaggtggc cactacaagt     960 ctccggggtgt cactcatgtg cccgctaggg aagatgcgcc tgactgtccc ttgtcgtgcc    1020
```

```
ctcacctgcg cccacctgca gagcttcgat gctgcccttt atctacagat gaatgagaag   1080
aagcctacat ggacatgtcc tgtgtgtgac aagaaggctc cctatgaatc tcttatcatt   1140
gatggtttat ttatggagat tcttagttcc tgttcagatt gtgatgagat ccaattcatg   1200
gaagatggat cctggtgccc aatgaaaccc aagaaggagg catctgaggt ttgcccccg    1260 ccagggtatg ggctggatgg cctccagtac agcccagtcc aggggggaga tccatcagag   1320
aataagaaga aggtcgaagt tattgacttg acaatagaaa gctcatcaga tgaggaggat   1380
ctgcccccta ccaagaagca ctgttctgtc acctcagctg ccatcccggc cctacctgga   1440
agcaaaggag tcctgacatc tggccaccag ccatcctcgg tgctaaggag ccctgctatg   1500
ggcacgttgg gtggggattt cctgtccagt ctcccactac atgagtaccc acctgccttc   1560
ccactgggag ccgacatcca aggtttagat ttatttttcat ttcttcagac agagagtcag   1620
cactatggcc cctctgtcat cacctcacta gatgaacagg atgcccttgg ccacttcttc   1680
cagtaccgag ggacccttc tcactttctg ggcccactgg cccccacgct ggggagctcc   1740
cactgcagcg ccactccggc gcccctcct ggccgtgtca gcagcattgt ggcccctggg   1800
ggggccttga gggaggggca tggaggaccc ctgccctcag gtccctcttt gactggctgt   1860
cggtcagaca tcatttccct ggactga                                       1887

<210> SEQ ID NO 9
<211> LENGTH: 552
<212> TYPE: DNA
<213> ORGANISM: Homo sapiens

<400> SEQUENCE: 9
cccttctatg aagtctatgg ggagctcatc cggcccacca cccttgcatc cacttctagc     60
cagcggtttg aggaagcgca ctttaccttt gccctcacac cccagcaagt gcagcagatt    120
cttacatcca gagaggttct gccaggagcc aaatgtgatt ataccataca ggtgcagcta    180
aggttctgtc tctgtgagac cagctgcccc caggaagatt attttccccc caacctcttt    240
gtcaaggtca atgggaaact gtgcccctg ccgggttacc ttccccccaac caagaatggg    300 gccgagccca gaggcccag ccgcccatc aacatcacac ccctggctcg actctcagcc    360
actgttccca acaccattgt ggtcaattgg tcatctgagt tcggacggaa ttactccttg    420
tctgtgtacc tggtgaggca gttgactgca ggaacccttc tacaaaaact cagagcaaag    480
ggtatccgga acccagacca ctcgcgggca ctgatcaagg agaaattgac tgctgaccct    540
gacagtgagg tg                                                       552

<210> SEQ ID NO 10
<211> LENGTH: 138
<212> TYPE: DNA
<213> ORGANISM: Homo sapiens

<400> SEQUENCE: 10
ttgcccttct atgaagtcta tggggagctc atccggccca ccaccttgc atccacttct      60 agccagcggt ttgaggaagc gcactttacc tttgccctca cccccagca agtgcagcag    120 attcttacat ccagagag                                                 138

<210> SEQ ID NO 11
<211> LENGTH: 11
<212> TYPE: PRT
<213> ORGANISM: Human immunodeficiency virus 1

<400> SEQUENCE: 11
```

Tyr Gly Arg Lys Lys Arg Arg Gln Arg Arg Arg
1               5                   10

<210> SEQ ID NO 12
<211> LENGTH: 33
<212> TYPE: DNA
<213> ORGANISM: Human immunodeficiency virus 1

<400> SEQUENCE: 12
tatggcagga agaagcggag acagcgacga aga                            33

<210> SEQ ID NO 13
<211> LENGTH: 33
<212> TYPE: DNA
<213> ORGANISM: Human immunodeficiency virus 1

<400> SEQUENCE: 13
tatggacgaa aaaacgacg acaacgacga cga                             33

<210> SEQ ID NO 14
<211> LENGTH: 24
<212> TYPE: DNA
<213> ORGANISM: Human immunodeficiency virus 1

<400> SEQUENCE: 14
cgacaacgac gaaagaagcg aggt                                      24

<210> SEQ ID NO 15
<211> LENGTH: 8
<212> TYPE: PRT
<213> ORGANISM: Human immunodeficiency virus 1

<400> SEQUENCE: 15

Arg Gln Arg Arg Lys Lys Arg Gly
1               5

<210> SEQ ID NO 16
<211> LENGTH: 40
<212> TYPE: PRT
<213> ORGANISM: Yersinia pestis

<400> SEQUENCE: 16

Lys Ser Lys Thr Glu Tyr Tyr Asn Ala Trp Ser Glu Trp Glu Arg Asn
1               5                   10                  15

Ala Pro Pro Gly Asn Gly Glu Gln Arg Glu Met Ala Val Ser Arg Leu
            20                  25                  30

Arg Asp Cys Leu Asp Arg Gln Ala
        35                  40

<210> SEQ ID NO 17
<211> LENGTH: 120
<212> TYPE: DNA
<213> ORGANISM: Yersinia pestis

<400> SEQUENCE: 17
aagagtaaga cggagtatta caatgcttgg tcagagtggg agcgaaacgc ccctccaggc    60
aatggggagc agcgagagat ggcggtgagt cggttgaggg actgtctcga caggcaggca   120

<210> SEQ ID NO 18
<211> LENGTH: 27
<212> TYPE: PRT
<213> ORGANISM: Unknown

```
<220> FEATURE:
<223> OTHER INFORMATION: Description of Unknown:
      Transportan sequence

<400> SEQUENCE: 18

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 19
<211> LENGTH: 81
<212> TYPE: DNA
<213> ORGANISM: Unknown
<220> FEATURE:
<223> OTHER INFORMATION: Description of Unknown:
      Transportan sequence

<400> SEQUENCE: 19
ggctggacac ttaacagcgc aggatatttg cttggcaaaa tcaatttgaa ggccttggct    60
gcgcttgcaa aaaaaattct c                                              81

<210> SEQ ID NO 20
<211> LENGTH: 16
<212> TYPE: PRT
<213> ORGANISM: Unknown
<220> FEATURE:
<223> OTHER INFORMATION: Description of Unknown:
      Penetratin sequence

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 48
<212> TYPE: DNA
<213> ORGANISM: Unknown
<220> FEATURE:
<223> OTHER INFORMATION: Description of Unknown:
      Penetratin sequence

<400> SEQUENCE: 21
cggcagataa aaatctggtt ccagaatcgg cgcatgaaat ggaagaaa                 48

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Arg Arg Arg Arg Arg Arg Arg His His His His His His
1               5                   10                  15

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
```
aggcggcgaa gacgccgcag gagacggcac caccatcacc atcac 45

<210> SEQ ID NO 24
<211> LENGTH: 124
<212> TYPE: PRT
<213> ORGANISM: Homo sapiens

<400> SEQUENCE: 24

| | | | | | | | | | | | | | | |
|---|---|---|---|---|---|---|---|---|---|---|---|---|---|---|
| Met | Glu | Asp | Gly | Ser | Trp | Cys | Pro | Met | Lys | Pro | Lys | Lys | Glu | Ala | Ser |
| 1 | | | | 5 | | | | | 10 | | | | | 15 | |
| Glu | Val | Cys | Pro | Pro | Gly | Tyr | Gly | Leu | Asp | Gly | Leu | Gln | Tyr | Ser |
| | | | 20 | | | | 25 | | | | 30 | | | |
| Pro | Val | Gln | Gly | Gly | Asp | Pro | Ser | Glu | Asn | Lys | Lys | Lys | Val | Glu | Val |
| | | 35 | | | | | 40 | | | | 45 | | | | |
| Ile | Asp | Leu | Thr | Ile | Glu | Ser | Ser | Ser | Asp | Glu | Glu | Asp | Leu | Pro | Pro |
| | 50 | | | | | 55 | | | | | 60 | | | | |
| Thr | Lys | Lys | His | Cys | Ser | Val | Thr | Ser | Ala | Ala | Ile | Pro | Ala | Leu | Pro |
| 65 | | | | | 70 | | | | | 75 | | | | | 80 |
| Gly | Ser | Lys | Gly | Val | Leu | Thr | Ser | Gly | His | Gln | Pro | Ser | Ser | Val | Leu |
| | | | | 85 | | | | | 90 | | | | | 95 | |
| Arg | Ser | Pro | Ala | Met | Gly | Thr | Leu | Gly | Gly | Asp | Phe | Leu | Ser | Ser | Leu |
| | | | 100 | | | | | 105 | | | | | 110 | | |
| Pro | Leu | His | Glu | Tyr | Pro | Pro | Ala | Phe | Pro | Leu | Gly |
| | | | 115 | | | | | 120 | | | |

<210> SEQ ID NO 25
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

| | | | | | | | | | | | | | | | |
|---|---|---|---|---|---|---|---|---|---|---|---|---|---|---|---|
| Met | Glu | Asp | Gly | Ser | Trp | Cys | Pro | Met | Lys | Pro | Lys | Lys | Glu | Ala | Ser |
| 1 | | | | 5 | | | | | 10 | | | | | 15 | |
| Glu | Val | Cys | Pro | Pro | Gly | Tyr | Gly | Leu | Asp | Gly | Leu | Gln | Tyr | Ser |
| | | | 20 | | | | 25 | | | | 30 | | | |
| Pro | Val | Gln | Gly | Gly | Asp | Pro | Ser | Glu | Asn | Lys | Lys | Lys | Val | Glu | Val |
| | | 35 | | | | | 40 | | | | 45 | | | | |
| Ile | Asp | Leu | Thr | Ile | Glu | Ser | Ser | Ser | Asp | Glu | Glu | Asp | Leu | Pro | Pro |
| | 50 | | | | | 55 | | | | | 60 | | | | |
| Thr | Lys | Lys | His | Cys | Ser | Val | Thr | Ser | Ala | Ala | Ile | Pro | Ala | Leu | Pro |
| 65 | | | | | 70 | | | | | 75 | | | | | 80 |
| Gly | Ser | Lys | Gly | Val | Leu | Thr | Ser | Gly | His | Gln | Pro | Ser | Ser | Val | Leu |
| | | | | 85 | | | | | 90 | | | | | 95 | |
| Arg | Ser | Pro | Ala | Met | Gly | Thr | Leu | Gly | Gly | Asp | Phe | Leu | Ser | Ser | Leu |
| | | | 100 | | | | | 105 | | | | | 110 | | |
| Pro | Leu | His | Glu | Tyr | Pro | Pro | Ala | Phe | Pro | Leu | Gly | Arg | Arg | Arg |
| | | | 115 | | | | | 120 | | | | | 125 | | |
| Arg | Arg | Arg | Arg | Arg | His | His | His | His | His |
| | | 130 | | | | | 135 | | |

<210> SEQ ID NO 26
<211> LENGTH: 124
<212> TYPE: PRT
<213> ORGANISM: Mus musculus

<400> SEQUENCE: 26

```
Met Glu Asp Gly Ser Trp Cys Pro Met Lys Pro Lys Glu Ala Ser
1               5                   10                  15

Glu Val Cys Pro Pro Gly Tyr Gly Leu Asp Gly Leu Gln Tyr Ser
            20                  25                  30

Ala Val Gln Glu Gly Ile Gln Pro Glu Ser Lys Lys Arg Val Glu Val
            35                  40                  45

Ile Asp Leu Thr Ile Glu Ser Ser Asp Glu Glu Asp Leu Pro Pro
    50                  55                  60

Thr Lys Lys His Cys Pro Val Thr Ser Ala Ala Ile Pro Ala Leu Pro
65              70                  75                  80

Gly Ser Lys Gly Ala Leu Thr Ser Gly His Gln Pro Ser Ser Val Leu
                85                  90                  95

Arg Ser Pro Ala Met Gly Thr Leu Gly Ser Asp Phe Leu Ser Ser Leu
                100                 105                 110

Pro Leu His Glu Tyr Pro Pro Ala Phe Pro Leu Gly
        115                 120
```

<210> SEQ ID NO 27
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Glu Asp Gly Ser Trp Cys Pro Met Lys Pro Lys Glu Ala Ser
1               5                   10                  15

Glu Val Cys Pro Pro Gly Tyr Gly Leu Asp Gly Leu Gln Tyr Ser
            20                  25                  30

Ala Val Gln Glu Gly Ile Gln Pro Glu Ser Lys Lys Arg Val Glu Val
            35                  40                  45

Ile Asp Leu Thr Ile Glu Ser Ser Asp Glu Glu Asp Leu Pro Pro
    50                  55                  60

Thr Lys Lys His Cys Pro Val Thr Ser Ala Ala Ile Pro Ala Leu Pro
65              70                  75                  80

Gly Ser Lys Gly Ala Leu Thr Ser Gly His Gln Pro Ser Ser Val Leu
                85                  90                  95

Arg Ser Pro Ala Met Gly Thr Leu Gly Ser Asp Phe Leu Ser Ser Leu
                100                 105                 110

Pro Leu His Glu Tyr Pro Pro Ala Phe Pro Leu Gly Arg Arg Arg
        115                 120                 125

Arg Arg Arg Arg Arg His His His His His His
        130                 135
```

<210> SEQ ID NO 28
<211> LENGTH: 225
<212> TYPE: PRT
<213> ORGANISM: Homo sapiens

<400> SEQUENCE: 28

```
Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
            35                  40                  45
```

```
Ser Ala Val Thr Gly Gly Glu Ala Asn Leu Leu Ser Ala Glu Pro
 50                  55                  60

Ala Gly Thr Phe Leu Ile Arg Asp Ser Ser Asp Gln Arg His Phe Phe
 65                  70                  75                  80

Thr Leu Ser Val Lys Thr Gln Ser Gly Thr Lys Asn Leu Arg Ile Gln
                 85                  90                  95

Cys Glu Gly Gly Ser Phe Ser Leu Gln Ser Asp Pro Arg Ser Thr Gln
                100                 105                 110

Pro Val Pro Arg Phe Asp Cys Val Leu Lys Leu Val His His Tyr Met
            115                 120                 125

Pro Pro Pro Gly Ala Pro Ser Phe Pro Ser Pro Thr Glu Pro Ser
        130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
            195                 200                 205

Gln Leu Pro Gly Pro Ile Arg Glu Phe Leu Asp Gln Tyr Asp Ala Pro
    210                 215                 220

Leu
225

<210> SEQ ID NO 29
<211> LENGTH: 675
<212> TYPE: DNA
<213> ORGANISM: Homo sapiens

<400> SEQUENCE: 29
atggtcaccc acagcaagtt tcccgccgcc gggatgagcc gcccctgga caccagcctg    60 cgcctcaaga ccttcagctc caagagcgag taccagctgg tggtgaacgc agtgcgcaag   120
ctgcaggaga gcggcttcta ctggagcgca gtgaccggcg cgaggcgaa cctgctgctc   180 agtgccgagc ccgccggcac ctttctgatc cgcgacagct cggaccagcg ccacttcttc   240
acgctcagcg tcaagaccca gtctgggacc aagaacctgc gcatccagtg tgagggggc   300 agcttctctc tgcagagcga tccccggagc acgcagcccg tgccccgctt cgactgcgtg   360
ctcaagctgg tgcaccacta catgccgccc cctggagccc cctccttccc ctcgccacct   420
actgaaccct cctccgaggt gcccgagcag ccgtctgccc agccactccc tgggagtccc   480 ccagaagag cctattacat ctactccggg ggcgagaaga tccccctggt gttgagccgg   540 ccctctcct ccaacgtggc cactcttcag catctctgtc ggaagaccgt caacggccac   600
ctggactcct atgagaaagt cacccagctg ccggggccca ttcgggagtt cctggaccag   660
tacgatgccc cgctt                                                   675

<210> SEQ ID NO 30
<211> LENGTH: 225
<212> TYPE: PRT
<213> ORGANISM: Mus musculus

<400> SEQUENCE: 30

Met Val Thr His Ser Lys Phe Pro Ala Ala Gly Met Ser Arg Pro Leu
 1                5                  10                  15
```

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
            115                 120                 125

Pro Pro Pro Gly Thr Pro Ser Phe Ser Leu Pro Pro Thr Glu Pro Ser
    130                 135                 140

Ser Glu Val Pro Glu Gln Pro Pro Ala Gln Ala Leu Pro Gly Ser Thr
145                 150                 155                 160

Pro Lys Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225

<210> SEQ ID NO 31
<211> LENGTH: 678
<212> TYPE: DNA
<213> ORGANISM: Mus musculus

<400> SEQUENCE: 31
atggtcaccc acagcaagtt tcccgccgcc gggatgagcc gcccccctgga caccagcctg     60 cgcctcaaga ccttcagctc caaaagcgag taccagctgg tggtgaacgc cgtgcgcaag    120
ctgcaggaga gcggattcta ctggagcgcc gtgaccggcg gcgaggcgaa cctgctgctc    180
agcgccgagc ccgcgggcac ctttcttatc cgcgacagct cggaccagcg ccacttcttc    240
acgttgagcg tcaagaccca gtcggggacc aagaacctac gcatccagtg tgagggggc    300 agcttttcgc tgcagagtga ccccgaagc acgcagccag ttccccgctt cgactgtgta    360
ctcaagctgg tgcaccacta catgccgcct ccagggaccc cctcctttc tttgccaccc    420 acggaaccct cgtccgaagt tccggagcag ccacctgccc aggcactccc cgggagtacc    480
cccaagagag cttactacat ctattctggg ggcgagaaga ttccgctggt actgagccga    540
cctctctcct ccaacgtggc caccctccag catctttgtc ggaagactgt caacggccac    600
ctggactcct atgagaaagt gacccagctg cctggaccca ttcgggagtt cctggatcag    660
tatgatgctc cactttaa                                                  678

<210> SEQ ID NO 32
<211> LENGTH: 387
<212> TYPE: PRT

<213> ORGANISM: Homo sapiens

<400> SEQUENCE: 32

Met Pro Thr Thr Ile Glu Arg Glu Phe Glu Leu Asp Thr Gln Arg
1               5                   10                  15

Arg Trp Gln Pro Leu Tyr Leu Gly Ile Arg Asn Glu Ser His Asp Tyr
            20                  25                  30

Pro His Arg Val Ala Lys Phe Pro Glu Asn Arg Asn Arg Asn Arg Tyr
                35                  40                  45

Arg Asp Val Ser Pro Tyr Asp His Ser Arg Val Lys Leu Gln Asn Ala
    50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
                100                 105                 110

Asn Arg Ile Val Glu Lys Glu Ser Val Lys Cys Ala Gln Tyr Trp Pro
            115                 120                 125

Thr Asp Asp Gln Glu Met Leu Phe Lys Glu Thr Gly Phe Ser Val Lys
130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
                245                 250                 255

Gly Leu Ile Gln Thr Pro Asp Gln Leu Arg Phe Ser Tyr Met Ala Ile
            260                 265                 270

Ile Glu Gly Ala Lys Cys Ile Lys Gly Asp Ser Ser Ile Gln Lys Arg
        275                 280                 285

Trp Lys Glu Leu Ser Lys Glu Asp Leu Ser Pro Ala Phe Asp His Ser
    290                 295                 300

Pro Asn Lys Ile Met Thr Glu Lys Tyr Asn Gly Asn Arg Ile Gly Leu
305                 310                 315                 320

Glu Glu Glu Lys Leu Thr Gly Asp Arg Cys Thr Gly Leu Ser Ser Lys
                325                 330                 335

Met Gln Asp Thr Met Glu Glu Asn Ser Glu Ser Ala Leu Arg Lys Arg
            340                 345                 350

Ile Arg Glu Asp Arg Lys Ala Thr Thr Ala Gln Lys Val Gln Gln Met
        355                 360                 365

Lys Gln Arg Leu Asn Glu Asn Glu Arg Lys Arg Lys Arg Pro Arg Leu
    370                 375                 380

Thr Asp Thr
385

<210> SEQ ID NO 33
<211> LENGTH: 1721
<212> TYPE: DNA
<213> ORGANISM: Homo sapiens

<400> SEQUENCE: 33

| | | | | | |
|---|---|---|---|---|---|
| gctcgggcgc | cgagtctgcg | cgctgacgtc | cgacgctcca | ggtactttcc | ccacggccga | 60 |
| cagggcttgg | cgtgggggcg | gggcgcggcg | cgcagcgcgc | atgcgccgca | gcgccagcgc | 120 |
| tctccccgga | tcgtgcgggg | cctgagcctc | tccgccggcg | caggctctgc | tcgcgccagc | 180 |
| tcgctcccgc | agccatgccc | accaccatcg | agcgggagtt | cgaagagttg | gatactcagc | 240 |
| gtcgctggca | gccgctgtac | ttggaaattc | gaaatgagtc | ccatgactat | cctcatagag | 300 |
| tggccaagtt | tccagaaaac | agaaatcgaa | acagatacag | agatgtaagc | ccatatgatc | 360 |
| acagtcgtgt | taaactgcaa | aatgctgaga | atgattatat | taatgccagt | ttagttgaca | 420 |
| tagaagaggc | acaaaggagt | tacatcttaa | cacagggtcc | acttcctaac | acatgctgcc | 480 |
| atttctggct | tatggtttgg | cagcagaaga | ccaaagcagt | tgtcatgctg | aaccgcattg | 540 |
| tggagaaaga | atcggttaaa | tgtgcacagt | actggccaac | agatgaccaa | gagatgctgt | 600 |
| ttaaagaaac | aggattcagt | gtgaagctct | tgtcagaaga | tgtgaagtcg | tattatacag | 660 |
| tacatctact | acaattagaa | aatatcaata | gtggtgaaac | cagaacaata | tctcactttc | 720 |
| attatactac | ctggccagat | tttggagtcc | ctgaatcacc | agcttcattt | ctcaatttct | 780 |
| tgtttaaagt | gagagaatct | ggctccttga | accctgacca | tgggcctgcg | gtgatccact | 840 |
| gtagtgcagg | cattgggcgc | tctggcacct | tctctctggt | agacacttgt | cttgttttga | 900 |
| tggaaaaagg | agatgatatt | aacataaaac | aagtgttact | gaacatgaga | aaataccgaa | 960 |
| tgggtcttat | tcagacccca | gatcaactga | gattctcata | catggctata | atagaaggag | 1020 |
| caaaatgtat | aagggagat | tctagtatac | agaaacgatg | gaaagaactt | tctaaggaag | 1080 |
| acttatctcc | tgcctttgat | cattcaccaa | acaaaataat | gactgaaaaa | tacaatggga | 1140 |
| acagaatagg | tctagaagaa | gaaaaactga | caggtgaccg | atgtacagga | cttcctctta | 1200 |
| aaatgcaaga | tacaatggag | gagaacagtg | agagtgctct | acggaaacgt | attcgagagg | 1260 |
| acagaaaggc | caccacagct | cagaaggtgc | agcagatgaa | acagaggcta | aatgagaatg | 1320 |
| aacgaaaaag | aaaaaggcca | agattgacag | acacctaata | ttcatgactt | gagaatattc | 1380 |
| tgcagctata | aattttgaac | cattgatgtg | caaagcaaga | cctgaagccc | actccggaaa | 1440 |
| ctaaagtgag | gctcgctaac | cctctagatt | gcctcacagt | tgtttgttta | caaagtaaac | 1500 |
| tttacatcca | ggggatgaag | agcacccacc | agcagaagac | tttgcagaac | ctttaattgg | 1560 |
| atgtgttaag | tgtttttaat | gagtgtatga | aatgtagaaa | gatgtacaag | aaataaatta | 1620 |
| ggggagatta | ctttgtattg | tactgccatt | cctactgtat | ttttatactt | tttggcagca | 1680 |
| ttaaatattt | ttgttaaata | gtcaaaaaaa | aaaaaaaaa | a | | 1721 |

<210> SEQ ID NO 34
<211> LENGTH: 382
<212> TYPE: PRT
<213> ORGANISM: Mus musculus

<400> SEQUENCE: 34

Met Ser Ala Thr Ile Glu Arg Glu Phe Glu Glu Leu Asp Ala Gln Cys
1               5                   10                  15

Arg Trp Gln Pro Leu Tyr Leu Glu Ile Arg Asn Glu Ser His Asp Tyr
            20                  25                  30

```
Pro His Arg Val Ala Lys Phe Pro Glu Asn Arg Asn Arg Asn Arg Tyr
        35                  40                  45
Arg Asp Val Ser Pro Tyr Asp His Ser Arg Val Lys Leu Gln Ser Thr
 50                  55                  60
Glu Asn Asp Tyr Ile Asn Ala Ser Leu Val Asp Ile Glu Glu Ala Gln
 65                  70                  75                  80
Arg Ser Tyr Ile Leu Thr Gln Gly Pro Leu Pro Asn Thr Cys Cys His
                 85                  90                  95
Phe Trp Leu Met Val Trp Gln Gln Lys Thr Lys Ala Val Val Met Leu
               100                 105                 110
Asn Arg Thr Val Glu Lys Glu Ser Val Lys Cys Ala Gln Tyr Trp Pro
             115                 120                 125
Thr Asp Asp Arg Glu Met Val Phe Lys Glu Thr Gly Phe Ser Val Lys
130                 135                 140
Leu Leu Ser Glu Asp Val Lys Ser Tyr Tyr Thr Val His Leu Leu Gln
145                 150                 155                 160
Leu Glu Asn Ile Asn Thr Gly Glu Thr Arg Thr Ile Ser His Phe His
                165                 170                 175
Tyr Thr Thr Trp Pro Asp Phe Gly Val Pro Glu Ser Pro Ala Ser Phe
            180                 185                 190
Leu Asn Phe Leu Phe Lys Val Arg Glu Ser Gly Cys Leu Thr Pro Asp
            195                 200                 205
His Gly Pro Ala Val Ile His Cys Ser Ala Gly Ile Gly Arg Ser Gly
210                 215                 220
Thr Phe Ser Leu Val Asp Thr Cys Leu Val Leu Met Glu Lys Gly Glu
225                 230                 235                 240
Asp Val Asn Val Lys Gln Leu Leu Leu Asn Met Arg Lys Tyr Arg Met
                245                 250                 255
Gly Leu Ile Gln Thr Pro Asp Gln Leu Arg Phe Ser Tyr Met Ala Ile
            260                 265                 270
Ile Glu Gly Ala Lys Tyr Thr Lys Gly Asp Ser Asn Ile Gln Lys Arg
            275                 280                 285
Trp Lys Glu Leu Ser Lys Glu Asp Leu Ser Pro Ile Cys Asp His Ser
290                 295                 300
Gln Asn Arg Val Met Val Glu Lys Tyr Asn Gly Lys Arg Ile Gly Ser
305                 310                 315                 320
Glu Asp Glu Lys Leu Thr Gly Leu Pro Ser Lys Val Gln Asp Thr Val
                325                 330                 335
Glu Glu Ser Ser Glu Ser Ile Leu Arg Lys Arg Ile Arg Glu Asp Arg
            340                 345                 350
Lys Ala Thr Thr Ala Gln Lys Val Gln Gln Met Lys Gln Arg Leu Asn
            355                 360                 365
Glu Thr Glu Arg Lys Arg Lys Arg Pro Arg Leu Thr Asp Thr
370                 375                 380

<210> SEQ ID NO 35
<211> LENGTH: 1149
<212> TYPE: DNA
<213> ORGANISM: Mus musculus

<400> SEQUENCE: 35
atgagcgcca ctattgagcg ggagttcgag gaactggacg cccagtgtag atggcagccc    60
ctttatcttg agatacgcaa cgaaagtcac gattaccctc atagggtagc taaattccct   120
```

```
gagaacagaa acagaaaccg ctaccgcgat gtgtcaccct acgatcactc cagagtgaaa    180
cttcaaagta ccgaaaatga ttatataaat gccagcttgg tggacataga ggaagcccaa    240
agatcataca tacttactca agggcctctc ccaaacactt gttgccattt ctggctcatg    300
gtgtggcaac agaagaccaa ggctgtggta atgctcaatc ggactgtgga aaaagagtca    360
gtaaagtgtg ctcaatattg gccaactgat gatagggaga tggtctttaa ggaaacaggt    420
ttctccgtta agttgctcag tgaggatgtg aagtcctatt acacagtaca tcttctccaa    480
ttggagaaca tcaacaccgg tgaaacccga acaatatccc actttcatta taccacttgg    540
cctgacttcg gtgttcctga agccccgct tcttttctca atttcctgtt taaggtgcgg     600
gagtcaggct gtctcacccc agatcatggg cctgctgtaa tacattgtag cgctgggatc    660
gggcgatccg ggacattctc tttggtagac acttgcctgg tcctgatgga agggagag     720 gacgtaaacg ttaagcagtt gctcctgaat atgagaaaat atcgaatggg gttgattcag    780
actcccgatc aacttagatt ctcttatatg gctataatcg agggcgcaaa atataccaag    840
ggggactcca acattcaaaa agatggaag gagctctcta aggaagatct gtctccaatc     900
tgtgaccaca gtcagaaccg agttatggta gagaaataca acggtaaaag aattggctca    960
gaagacgaaa aactgaccgg actccccctcc aaagtgcaag atacagtcga agaatcatcc   1020
gagtcaatct tgaggaaaag aatcagggaa gatcggaagg ccactacagc ccaaaaagtg    1080
caacaaatga aacagcgact caacgaaaca gagcggaaac gaaaacggcc aagactgaca    1140
gacacctaa                                                            1149

<210> SEQ ID NO 36
<211> LENGTH: 769
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ala Gln Trp Asn Gln Leu Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175
```

```
Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590
```

```
Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ala Ala Pro Phe
690                 695                 700

Leu Lys Thr Lys Phe Ile Cys Val Thr Pro Thr Thr Cys Ser Asn Thr
705                 710                 715                 720

Ile Asp Leu Pro Met Ser Pro Arg Thr Leu Asp Ser Leu Met Gln Phe
                725                 730                 735

Gly Asn Asn Gly Glu Gly Ala Glu Pro Ser Ala Gly Gly Gln Phe Glu
            740                 745                 750

Ser Leu Thr Phe Asp Met Glu Leu Thr Ser Glu Cys Ala Thr Ser Pro
        755                 760                 765

Met
```

<210> SEQ ID NO 37
<211> LENGTH: 2310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atggcccaat ggaatcagct acagcagctt gacacacggt acctggagca gctccatcag    60
ctctacagtg acagcttccc aatggagctg cggcagtttc tggcccccttg gattgagagt   120 caagattggg catatgcggc cagcaaagaa tcacatgcca ctttggtgtt tcataatctc   180
ctgggagaga ttgaccagca gtatagccgc ttcctgcaag agtcgaatgt tctctatcag   240
cacaatctac gaagaatcaa gcagtttctt cagagcaggt atcttgagaa gccaatggag   300
attgcccgga ttgtggcccg gtgcctgtgg gaagaatcac gccttctaca gactgcagcc   360
actgcggccc agcaaggggg ccaggccaac caccccacag cagccgtggt gacggagaag   420
cagcagatgc tggagcagca ccttcaggat gtccggaaga gagtgcagga tctagaacag   480
aaaatgaaag tggtagagaa tctccaggat gactttgatt tcaactataa aaccctcaag   540
agtcaaggag acatgcaaga tctgaatgga acaaccagt cagtgaccag gcagaagatg   600
cagcagctgg aacagatgct cactgcgctg gaccagatgc ggagaagcat cgtgagtgag   660
ctggcggggc ttttgtcagc gatggagtac gtgcagaaaa ctctcacgga cgaggagctg   720
gctgactgga agaggcggca acagattgcc tgcattggag gccgcccaa catctgccta   780 gatcggctag aaaactggat aacgtcatta gcagaatctc aacttcagac ccgtcaacaa   840
attaagaaac tggaggagtt gcagcaaaaa gtttcctaca aggggaccc cattgtacag   900 caccggccga tgctggagga gagaatcgtg gagctgttta gaaacttaat gaaaagtgcc   960
tttgtggtgg agcggcagcc ctgcatgccc atgcatcctg accggcccct cgtcatcaag  1020
```

```
accggcgtcc agttcactac taaagtcagg ttgctggtca aattccctga gttgaattat  1080
cagcttaaaa ttaaagtgtg cattgacaaa gactctgggg acgttgcagc tctcagagga  1140
tcccggaaat ttaacattct gggcacaaac acaaaagtga tgaacatgga agaatccaac  1200
aacggcagcc tctctgcaga attcaaacac ttgaccctga gggagcagag atgtgggaat  1260
gggggccgag ccaattgtga tgcttccctg attgtgactg aggagctgca cctgatcacc  1320
tttgagaccg aggtgtatca ccaaggcctc aagattgacc tagagaccca ctccttgcca  1380
gttgtggtga tctccaacat ctgtcagatg ccaaatgcct gggcgtccat cctgtggtac  1440
aacatgctga ccaacaatcc caagaatgta aacttttta ccaagccccc aattggaacc  1500
tgggatcaag tggccgaggt cctgagctgg cagttctcct ccaccaccaa gcgaggactg  1560
agcatcgagc agctgactac actggcagag aaactcttgg acctggtgt gaattattca  1620 gggtgtcaga tcacatgggc taaattttgc aaagaaaaca tggctggcaa gggcttctcc  1680
ttctgggtct ggctggacaa tatcattgac cttgtgaaaa agtacatcct ggcccttttgg  1740 aacgaagggt acatcatggg ctttatcagt aaggagcggg agcgggccat cttgagcact  1800
aagcctccag gcaccttcct gctaagattc agtgaaagca gcaaagaagg aggcgtcact  1860
ttcacttggg tggagaagga catcagcggt aagacccaga tccagtccgt ggaaccatac  1920
acaaagcagc agctgaacaa catgtcattt gctgaaatca tcatgggcta taagatcatg  1980
gatgctacca atatcctggt gtctccactg gtctatctct atcctgacat tcccaaggag  2040
gaggcattcg gaaagtattg tcggccgaga gccaggagc atcctgaagc tgacccaggc  2100
gctgccccat tcctgaagac caagtttatc tgtgtgacac caacgacctg cagcaatacc  2160
attgacctgc cgatgtcccc ccgcacttta gattcattga tgcagtttgg aaataatggt  2220
gaaggtgctg aaccctcagc aggagggcag tttgagtccc tcacctttga catggagttg  2280
acctcggagt gcgctacctc ccccatgtga                                     2310
```

<210> SEQ ID NO 38
<211> LENGTH: 769
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125
```

```
Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Ala Ala Leu His Leu Ile Thr Phe Glu Thr Glu Val Tyr His Gln
        435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
530                 535                 540
```

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
            565                 570                 575

Leu Ala Leu Trp Asn Glu Gly Tyr Ile Met Gly Phe Ile Ser Lys Glu
        580                 585                 590

Arg Glu Arg Ala Ile Leu Ser Thr Lys Pro Pro Gly Thr Phe Leu Leu
    595                 600                 605

Arg Phe Ser Glu Ser Ser Lys Glu Gly Gly Val Thr Phe Thr Trp Val
610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
            645                 650                 655

Tyr Lys Ile Met Asp Ala Thr Asn Ile Leu Val Ser Pro Leu Val Tyr
        660                 665                 670

Leu Tyr Pro Asp Ile Pro Lys Glu Glu Ala Phe Gly Lys Tyr Cys Arg
    675                 680                 685

Pro Glu Ser Gln Glu His Pro Glu Ala Asp Pro Gly Ala Ala Pro Tyr
690                 695                 700

Leu Lys Thr Lys Phe Ile Cys Val Thr Pro Thr Thr Cys Ser Asn Thr
705                 710                 715                 720

Ile Asp Leu Pro Met Ser Pro Arg Thr Leu Asp Ser Leu Met Gln Phe
            725                 730                 735

Gly Asn Asn Gly Glu Gly Ala Glu Pro Ser Ala Gly Gly Gln Phe Glu
        740                 745                 750

Ser Leu Thr Phe Asp Met Glu Leu Thr Ser Glu Cys Ala Thr Ser Pro
    755                 760                 765

Met

<210> SEQ ID NO 39
<211> LENGTH: 2310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atggcccaat ggaatcagct acagcagctt gacacacggt acctggagca gctccatcag      60
ctctacagtg acagcttccc aatggagctg cggcagtttc tggccccttg gattgagagt     120
caagattggg catatgcggc cagcaaagaa tcacatgcca ctttggtgtt tcataatctc     180
ctggagagat tgaccagca gtatagccgc ttcctgcaag agtcgaatgt tctctatcag     240
cacaatctac gaagaatcaa gcagtttctt cagagcaggt atcttgagaa gccaatggag     300
attgcccgga ttgtggcccg tgcctgtggg aagaatcac gccttctaca gactgcagcc     360
actgcggccc agcaagggg ccaggccaac caccccacag cagccgtggt gacggagaag     420
cagcagatgc tggagcagca ccttcaggat gtccggaaga gagtgcagga tctagaacag     480
aaaatgaaag tggtagagaa tctccaggat gactttgatt tcaactataa acccctcaag     540
agtcaaggag acatgcaaga tctgaatgga acaaccagt cagtgaccag cagaagatg     600 cagcagctgg aacagatgct cactgcgctg accagatgc ggagaagcat cgtgagtgag     660 ctggcgggc ttttgtcagc gatggagtac gtgcagaaaa ctctcacgga cgaggagctg     720

-continued

```
gctgactgga agaggcggca acagattgcc tgcattggag gcccgcccaa catctgccta      780
gatcggctag aaaactggat aacgtcatta gcagaatctc aacttcagac ccgtcaacaa      840
attaagaaac tggaggagtt gcagcaaaaa gtttcctaca aaggggaccc cattgtacag      900
caccggccga tgctggagga gagaatcgtg gagctgttta gaaacttaat gaaaagtgcc      960
tttgtggtgg agcggcagcc ctgcatgccc atgcatcctg accggcccct cgtcatcaag     1020
accggcgtcc agttcactac taaagtcagg ttgctggtca aattccctga gttgaattat     1080
cagcttaaaa ttaaagtgtg cattgacaaa gactctgggg acgttgcagc tctcagagga     1140
tcccggaaat ttaacattct gggcacaaac acaaaagtga tgaacatgga agaatccaac     1200
aacggcagcc tctctgcaga attcaaacac ttgaccctga gggagcagag atgtgggaat     1260
gggggccgag ccaattgtga tgcttccctg attgtgactg cggcgctgca cctgatcacc     1320
tttgagaccg aggtgtatca ccaaggcctc aagattgacc tagagaccca ctccttgcca     1380
gttgtggtga tctccaacat ctgtcagatg ccaaatgcct gggcgtccat cctgtggtac     1440
aacatgctga ccaacaatcc caagaatgta aactttttta ccaagccccc aattggaacc     1500
tgggatcaag tggccgaggt cctgagctgg cagttctcct ccaccaccaa gcgaggactg     1560
agcatcgagc agctgactac actggcagag aaactcttgg acctggtgt gaattattca     1620 gggtgtcaga tcacatgggc taaattttgc aaagaaaaca tggctggcaa gggcttctcc     1680
ttctgggtct ggctggacaa tatcattgac cttgtgaaaa agtacatcct ggcccttggg     1740
aacgaagggt acatcatggg ctttatcagt aaggagcggg agcgggccat cttgagcact     1800
aagcctccag gcaccttcct gctaagattc agtgaaagca gcaaagaagg aggcgtcact     1860
ttcacttggg tggagaagga catcagcggt aagacccaga tccagtccgt ggaaccatac     1920
acaaagcagc agctgaacaa catgtcattt gctgaaatca tcatgggcta taagatcatg     1980
gatgctacca atatcctggt gtctccactg gtctatctct atcctgacat tcccaaggag     2040
gaggcattcg gaaagtattg tcggccagag agccaggagc atcctgaagc tgacccaggc     2100
gctgccccat acctgaagac caagtttatc tgtgtgacac caacgacctg cagcaatacc     2160
attgacctgc cgatgtcccc ccgcactttta gattcattga tgcagtttgg aaataatggt     2220
gaaggtgctg aaccctcagc aggagggcag tttgagtccc tcacctttga catggagttg     2280
acctcggagt gcgctacctc ccccatgtga                                      2310
```

<210> SEQ ID NO 40
<211> LENGTH: 372
<212> TYPE: DNA
<213> ORGANISM: Homo sapiens

<400> SEQUENCE: 40

```
atggaagatg gatcctggtg cccaatgaaa cccaagaagg aggcatctga ggtttgcccc       60
ccgccagggt atgggctgga tggcctccag tacagcccag tccaggggggg agatccatca     120 gagaataaga agaaggtcga agttattgac ttgacaatag aaagctcatc agatgaggag      180
gatctgcccc ctaccaagaa gcactgttct gtcacctcag ctgccatccc ggccctacct      240
ggaagcaaag gagtcctgac atctggccac cagccatcct cggtgctaag gagccctgct      300
atgggcacgt gggtgggga tttcctgtcc agtctcccac tacatgagta cccacctgcc      360
ttcccactgg ga                                                         372
```

<210> SEQ ID NO 41
<211> LENGTH: 420

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggaagatg gatcctggtg cccaatgaaa cccaagaagg aggcatctga ggtttgcccc      60
ccgccagggt atgggctgga tggcctccag tacagcccag tccagggggg agatccatca     120
gagaataaga agaaggtcga agttattgac ttgacaatag aaagctcatc agatgaggag     180
gatctgcccc ctaccaagaa gcactgttct gtcacctcag ctgccatccc ggccctacct     240
ggaagcaaag gagtcctgac atctggccac cagccatcct cggtgctaag gagccctgct     300
atgggcacgt gggtgggga tttcctgtcc agtctcccac tacatgagta cccacctgcc     360
ttcccactgg gaaggcggcg aagacgccgc aggagacggc accaccatca ccatcactaa     420
```

<210> SEQ ID NO 42
<211> LENGTH: 378
<212> TYPE: DNA
<213> ORGANISM: Mus musculus

<400> SEQUENCE: 42

```
atggaagatg gatcctggtg tccgatgaaa cccaagaagg aggcatcaga ggtttgcccc      60
ccgccagggt atgggctgga tggtctccag tacagcgcag tccaggaggg aattcagcca     120
gagagtaaga agagggtcga agtcattgac ttgaccatcg aaagctcatc agatgaggag     180
gatttgcccc ccaccaagaa gcactgccct gtcacctcag cggccattcc agcccttcct     240
ggaagcaaag gagccctgac ctctggtcac cagccatcct cggtgctgcg agccctgca     300
atgggcacac tgggcagtga cttcctgtct agtctcccgc tacatgagta cccacctgcc     360
ttcccactgg ggcgacga                                                   378
```

<210> SEQ ID NO 43
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atggaagatg gatcctggtg tccgatgaaa cccaagaagg aggcatcaga ggtttgcccc      60
ccgccagggt atgggctgga tggtctccag tacagcgcag tccaggaggg aattcagcca     120
gagagtaaga agagggtcga agtcattgac ttgaccatcg aaagctcatc agatgaggag     180
gatttgcccc ccaccaagaa gcactgccct gtcacctcag cggccattcc agcccttcct     240
ggaagcaaag gagccctgac ctctggtcac cagccatcct cggtgctgcg agccctgca     300
atgggcacac tgggcagtga cttcctgtct agtctcccgc tacatgagta cccacctgcc     360
ttcccactgg ggcgacgaag gcggcgaaga cggaggcggc atcaccatca tcaccactaa     420
```

ONCOLYTIC VIRUSES TARGETING STAT3

CROSS-REFERENCE

This application is a continuation of International Application No. PCT/US2017/042910, filed Jul. 19, 2017, which claims the benefit of U.S. Provisional Application No. 62/364,095, filed Jul. 19, 2016, both of which are incorporated by reference herein in their entireties.

GRANT INFORMATION

This disclosure was made with government support under CA178766 awarded by the National Institutes of Health. The government has certain rights in the disclosure.

INCORPORATION BY REFERENCE

All publications, patents, patent applications, and NCBI accession numbers mentioned in this specification are herein incorporated by reference to the same extent as if each individual publication, patent, or patent application was specifically and individually indicated to be incorporated by reference, and as if set forth in their entireties. In the event of a conflict between a term as used herein and the term as defined in the incorporated reference, the definition of this disclosure controls.

SEQUENCE LISTING

The specification further incorporates by reference the Sequence Listing submitted herewith via EFS on Jan. 18, 2019. Pursuant to 37 C.F.R. § 1.52(e)(5), the Sequence Listing text file, identified as 072396_0747_SL.TXT, is 71,513 bytes and was created on Jan. 17, 2019. The Sequence Listing, electronically filed herewith, does not extend beyond the scope of the specification and thus does not contain new matter.

INTRODUCTION

Embodiments herein relate to oncolytic viruses that can modulate STAT3 (signal transducer and activator of transcription 3)-mediated gene activation.

SUMMARY

Provided herein in one embodiment is an oncolytic vaccinia virus which can comprise an exogenous nucleic acid, wherein said exogenous nucleic acid can encode a protein or a fragment thereof that can modulate STAT3-mediated gene-activation. In certain embodiments, the exogenous nucleic acid can encode the protein. In certain embodiments, the exogenous nucleic acid can encode the fragment.

In certain embodiments, the protein or the fragment thereof can comprise a STAT3 recognition domain or a blocking fragment within said recognition domain. In certain embodiments, the oncolytic vaccinia virus can comprise the blocking fragment, wherein the blocking fragment can modulate STAT3-mediated gene activation.

In certain embodiments, the protein or the fragment thereof can be a PIAS3 protein or a fragment thereof. In certain embodiments, the protein or the fragment thereof can be a SOCS3 protein or a fragment thereof, a TCPTP protein or a fragment thereof, or a STAT3 protein or a fragment thereof.

In certain embodiments, the protein or the fragment thereof can be a PIAS3 protein or a fragment thereof. In certain embodiments, the exogenous nucleic acid can be codon optimized for increased expression of the PIAS3 protein or the fragment thereof, the SOCS3 protein or a fragment thereof, the TCPTP protein or the fragment thereof, or the dominant-negative mutant STAT3 protein or the fragment thereof. In certain embodiments, the exogenous nucleic acid can encode the PIAS3 protein, wherein the exogenous nucleic acid can be at least about 85%, at least about 90%, at least about 95%, at least about 96%, at least about 97%, at least about 98%, at least about 99%, or 100% homologous to a nucleic acid sequence selected from the group consisting of SEQ ID NOs: 8-10 and 40-43. In certain embodiments, the exogenous nucleic acid can encode the PIAS3 protein, wherein the exogenous nucleic acid can comprise a nucleotide sequence selected from the group consisting of SEQ ID NOs: 8-10 and 40-43. In certain embodiments, the exogenous nucleic acid coding for the PIAS3 protein, wherein the exogenous nucleic acid can be at least about 85%, at least about 90%, at least about 95%, at least about 96%, at least about 97%, at least about 98%, at least about 99%, or 100% homologous to the entire length of a nucleic acid sequence selected from the group consisting of SEQ ID NOs: 8-10 and 40-43. In certain embodiments, the exogenous nucleic acid can encode the PIAS3 protein, wherein the exogenous nucleic acid can be at least about 85%, at least about 90%, at least about 95%, at least about 96%, at least about 97%, at least about 98%, at least about 99%, or 100% homologous to a fraction of a nucleic acid sequence selected from the group consisting of SEQ ID NOs: 8-10 and 40-43. In certain embodiments, the exogenous nucleic acid can encode the PIAS3 protein fragment, wherein the exogenous nucleic acid can be at least about 85%, at least about 90%, at least about 95%, at least about 96%, at least about 97%, at least about 98%, at least about 99%, or 100% homologous to a nucleic acid fragment of a nucleotide sequence selected from the group consisting of SEQ ID NOs: 8-10 and 40-43. In certain embodiments, the exogenous nucleic acid can encode the PIAS3 protein fragment, wherein the exogenous nucleic acid comprises a nucleic acid fragment of a nucleotide sequence that can be selected from of the group consisting of SEQ ID NOs: 8-10 and 40-43. In certain embodiments, the nucleic acid fragment can comprise a contiguous stretch of nucleotides from a nucleotide sequence selected from the group consisting of SEQ ID NOs: 8-10 and 40-43. In certain embodiments, the contiguous stretch of nucleotides can have a length from 3 nucleotides to 552 nucleotides. In certain embodiments, the nucleic acid fragment can comprise a non-contiguous nucleotides from a nucleotide sequence selected from the group consisting of SEQ ID NOs: 8-10 and 40-43.

In certain embodiments, the exogenous nucleic acid coding for the PIAS3 protein, wherein the PIAS3 protein comprises an amino acid sequence that can be at least about 85%, at least about 90%, at least about 95%, at least about 96%, at least about 97%, at least about 98%, at least about 99%, or 100% homologous to an amino acid sequence selected from the group consisting of SEQ ID NOs: 1-7 and 24-27 and conservative substitutions thereof. In certain embodiments, the exogenous nucleic acid coding for the PIAS3 protein, wherein the PIAS3 protein can comprise an amino acid sequence that is at least about 85%, at least about 90%, at least about 95%, at least about 96%, at least about 97%, at least about 98%, at least about 99%, or 100% homologous to the amino acid sequence of SEQ ID NO: 1 and conservative substitutions thereof. In certain embodiments, the exogenous nucleic acid can encode the PIAS3 protein, wherein the PIAS3 protein can comprise an amino acid sequence that can be at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 1-7 and 24-27 and conservative substitutions thereof. In certain embodiments, the exogenous nucleic acid can encode the PIAS3 protein, wherein the PIAS3 protein can comprise an amino acid sequence that is at least about 85%, at least about 90%, at least about 95%, at least about 96%, at least about 97%, at least about 98%, at least about 99%, or 100% homologous to the entire length of the amino acid sequence of SEQ ID NO: 1 and conservative substitutions thereof. In certain embodiments, the exogenous nucleic acid can encode the PIAS3 protein, wherein the PIAS3 protein can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 1-7 and 24-27 and conservative substitutions thereof. In certain embodiments, the exogenous nucleic acid can encode the PIAS3 protein, wherein the PIAS3 protein can comprise an amino acid sequence that can be at least about 85%, at least about 90%, at least about 95%, at least about 96%, at least about 97%, at least about 98%, at least about 99%, or 100% homologous to a fraction of the entire length of the amino acid sequence of SEQ ID NO: 1 and conservative substitutions thereof. In certain embodiments, the exogenous nucleic acid coding for the PIAS3 protein fragment, wherein the PIAS3 protein fragment can comprise an amino acid sequence that can be at least about 85%, at least about 90%, at least about 95%, at least about 96%, at least bout 97%, at least about 98%, at least about 99%, or 100% homologous to an amino acid fragment from any one of SEQ ID NOs: 1-7 and 24-27 and conservative substitutions thereof. In certain embodiments, the exogenous nucleic acid can encode the PIAS3 protein fragment, wherein the PIAS3 protein fragment can comprise an amino acid sequence that can be at least about 85%, at least about 90%, at least about 95%, at least about 96%, at least about 97%, at least about 98%, at least about 99%, or 100% homologous to an amino acid fragment from SEQ ID NO: 1 and conservative substitutions thereof. In certain embodiments, the PIAS3 protein or a fragment thereof encoded by an exogenous nucleic acid disclosed herein can comprise amino acids 400-528 of the amino acid sequence of SEQ ID NO: 1 and conservative substitutions thereof. In certain embodiments, the PIAS3 protein or a fragment thereof encoded by an exogenous nucleic acid disclosed herein can comprise amino acids 400-523 of the amino acid sequence of SEQ ID NO: 6 and conservative substitutions thereof.

In certain embodiments, the protein or a fragment thereof that modulates STAT3 activity, e.g., modulate STAT3-mediated gene-activation, is a SOCS3 protein or a fragment thereof and conservative substitutions thereof. In certain embodiments, the SOCS3 protein or a fragment thereof can comprise a human SOCS3 protein or a fragment thereof and conservative substitutions thereof. In certain embodiments, the SOCS3 protein or the fragment thereof can comprise an amino acid sequence that can be at least about 85% homologous to an amino acid sequence selected from the group consisting of SEQ ID NOs: 28 and 30 and conservative substitutions thereof. In certain embodiments, the SOCS3 protein or the fragment thereof can comprise an amino acid sequence that can be at least about 85% homologous to the amino acid sequence of SEQ ID NO: 28 and conservative substitutions thereof. In certain embodiments, the SOCS3 protein or the fragment thereof can comprise an amino acid sequence that can be at least about 85% homologous to the entire length of an amino acid sequence selected from the group consisting of SEQ ID NOs: 28 and 30 and conservative substitutions thereof. In certain embodiments, the SOCS3 protein or the fragment thereof can comprise an amino acid sequence that can be at least about 85% homologous to a fraction of the entire length of an amino acid sequence selected from the group consisting of SEQ ID NOs: 28 and 30 and conservative substitutions thereof.

In certain embodiments, the protein or the fragment thereof that modulates STAT3 activity, e.g., modulate STAT3-mediated gene-activation, can be a TCPTP protein or a fragment thereof and conservative substitutions thereof. In certain embodiments, the TCPTP protein or the fragment thereof can be a human TCPTP protein or a fragment thereof and conservative substitutions thereof. In certain embodiments, the TCPTP protein or the fragment thereof can comprise an amino acid sequence that can be at least about 85% homologous to an amino acid sequence selected from the group consisting of SEQ ID NOs: 32 and 34 and conservative substitutions thereof. In certain embodiments, the TCPTP protein or the fragment thereof can comprise an amino acid sequence that can be at least about 85% homologous to the amino acid sequence of SEQ ID NO: 32 and conservative substitutions thereof. In certain embodiments, the TCPTP protein or the fragment thereof can comprise an amino acid sequence that can be at least about 85% homologous to the entire length of an amino acid sequence selected from the group consisting of SEQ ID NOs: 32 and 34 and conservative substitutions thereof. In certain embodiments, the TCPTP protein or portion thereof can comprise an amino acid sequence that can be at least about 85% homologous to a fraction of the entire length of an amino acid sequence selected from the group consisting of SEQ ID NOs: 32 and 34 and conservative substitutions thereof.

In certain embodiments, a protein or a fragment thereof that modulates STAT3 activity, e.g., modulate STAT3-mediated gene-activation, can be a dominant-negative mutant STAT3 protein or a fragment thereof and conservative substitutions thereof. In certain embodiments, the dominant-negative mutant STAT3 protein or the fragment thereof can be a human dominant-negative mutant STAT3 protein or a fragment thereof and conservative substitutions thereof. In certain embodiments, the dominant-negative mutant STAT3 protein or the fragment thereof can comprise an amino acid sequence that can be at least about 85% homologous to an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to the entire length of an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to a portion of the entire length of an amino acid sequence selected from the group consisting of SEQ ID NOs: 36 and 38 and conservative substitutions thereof.

In certain embodiments, the exogenous nucleic acid can be inserted into the vaccinia viral genome.

In certain embodiments, the exogenous nucleic acid can be inserted into the thymidine kinase locus of the vaccinia viral genome. In certain embodiments, the oncolytic vaccinia virus can be an extracellular enveloped virus (EEV). In certain embodiments, the oncolytic vaccinia virus can replicate within M2 macrophages in tumor cells. In certain embodiments, the oncolytic vaccinia virus can replicate within the M2 macrophages in tumor cells to produce a population of viruses that predominantly contains extracellular enveloped viruses (EEVs). In certain embodiments, the oncolytic vaccinia virus can partially avoid immunosuppression by replicating within the M2 macrophages.

The present disclosure further provides a pharmaceutical composition that can comprise an oncolytic vaccinia virus as described herein, and an excipient. In certain embodiments, the excipient can comprise one or more of a buffering agent, a stabilizer, an antioxidant, a binder, a diluent, a dispersing agent, a rate controlling agent, a lubricant, a glidant, a disintegrant, a plasticizer, a preservative, or any combination thereof. In certain embodiments, the excipient can comprise di-sodium hydrogen phosphate dihydrate, sodium dihydrogen phosphate dihydrate, sodium chloride, myo-inositol, sorbitol, or any combination thereof. In certain embodiments, the pharmaceutical compositions may not comprise a preservative. In certain embodiments, the pharmaceutical compositions can further comprise one or more of a preservative, a diluent, and a carrier. In certain embodiments, the pharmaceutical composition can further comprise an additional active ingredient or a salt thereof. In certain embodiments, the pharmaceutical compositions can comprise the additional active ingredient, wherein the additional active ingredient can be a further oncolytic vaccinia virus.

The present disclosure further provides a process for producing an oncolytic vaccinia virus as described herein, wherein the process can comprise the following steps: (i) generating a modified vaccinia virus DNA vector by operably linking a vaccinia virus base nucleic acid sequence to the exogenous nucleic acid sequence according as described above; (ii) transfecting mammalian cells with the modified vaccinia virus DNA vector; (iii) culturing the mammalian cells in conditions suitable for viral replication; and (iv) harvesting the viral particles. In certain embodiments, the mammalian cells comprise HeLa cells. 293 cells, or Vero cells. In certain embodiments, the exogenous nucleic acid in the modified vaccinia virus DNA vector can promote a population of viral particles predominantly containing extracellular enveloped viruses (EEV).

The present disclosure provides methods of treatment by administering one or more of the disclosed vaccinia viruses. In certain embodiments, a method of treating a cancer can comprise administering to a subject in need thereof a therapeutically effective amount of an oncolytic vaccinia virus according to this disclosure or a pharmaceutical composition as described herein. In some embodiment, the method can comprise the administration of a therapeutically effective amount of an oncolytic vaccinia virus according to this disclosure or a pharmaceutical composition as described herein, wherein the cancer can be a solid tumor, a leukemia, or a lymphoma.

One non-limiting embodiment provides a method of treating a tumor, wherein the method can comprise administering to a subject in need thereof a therapeutically effective amount of an oncolytic vaccinia virus according to this disclosure or a pharmaceutical composition as described herein. In certain embodiments, the method can comprise the administration of a therapeutically effective amount of an oncolytic vaccinia virus according to this disclosure or a pharmaceutical composition as described herein, wherein the tumor can be a solid tumor, a leukemia, or a lymphoma.

One non-limiting embodiment provides, a method of treating a cancer or a tumor, wherein the method can comprise administering to a subject in need thereof a therapeutically effective amount of an oncolytic vaccinia virus according to this disclosure or a pharmaceutical composition as described herein, in combination with a further therapy. In certain embodiments, the method can comprise administration of the further therapy, wherein the further therapy can comprise chemotherapy, radiation, oncolytic viral therapy with an additional virus, treatment with immunomodulatory proteins, a STAT3 inhibitor, an anti-cancer agent, or any combinations thereof. In certain embodiments, the method can comprise administration of the further therapy, wherein the further therapy can be administered concurrently or sequentially. In certain embodiments, the method can comprise sequential administration of the further therapy, wherein the further therapy can be administered prior to administering the oncolytic vaccinia virus according to this disclosure or a pharmaceutical composition as described herein. In certain embodiments, the method can comprise sequential administration of the further therapy, wherein the further therapy can be administered after administering the oncolytic vaccinia virus according to this disclosure or a pharmaceutical composition as described herein.

One non-limiting embodiment provides a method of at least partially re-sensitizing a cancer patient to a cancer therapy, wherein the method can comprise administering to a subject in need thereof a therapeutically effective amount of an oncolytic vaccinia virus according to this disclosure or a pharmaceutical composition as described herein, in combination with a drug that can enhance the replication of the vaccinia virus within tumor cells. In certain embodiments, the method can comprise the administration of the therapeutically effective amount of an oncolytic vaccinia virus according to this disclosure or a pharmaceutical composition as described herein, wherein the cancer therapy can comprise chemotherapy, radiation, viral therapy, treatment with immunomodulatory proteins, or any combinations thereof.

One non-limiting embodiment provides a method of producing a toxic effect in cancer cells, wherein the method can comprise administering to a population of cancer cells a therapeutically effective amount of an oncolytic vaccinia virus according to this disclosure or a pharmaceutical composition as described herein. In certain embodiments, the method can comprise the administration of the therapeutically effective amount of an oncolytic vaccinia virus according to this disclosure or a pharmaceutical composition as described herein, wherein not every cancer cell in the population of cancer cells can be infected with the oncolytic vaccinia virus. In certain embodiments, the growth of a non-infected cancer cell can be inhibited without direct infection One non-limiting embodiment provides, a method of determining the infectivity of an oncolytic vaccinia virus, wherein the method can comprise: (i) collecting a first biological sample from a subject and determining the level of STAT3 in the first biological sample; (ii) administering to the subject effective therapeutically effective amount of an oncolytic vaccinia virus according to this disclosure or a pharmaceutical composition as described herein, alone or in combination with a further therapy; (iii) collecting a second biological sample from the subject after about 2 hours to about 72 hours following the administration in step (ii) and detecting the level of a STAT3 protein in the second biological sample. In certain embodiments, the method can comprise administration of the further therapy, wherein the further therapy can comprise chemotherapy, radiation, oncolytic viral therapy with an additional virus, treatment with immunomodulatory proteins, a STAT3 inhibitor, an anticancer agent, or any combinations thereof. In certain embodiments, the method can comprise administration of the further therapy, wherein the further therapy can be administered concurrently or sequentially. In certain embodiments, the method can comprise sequential administration of the further therapy, wherein the further therapy can be administered prior to administering the oncolytic vaccinia virus according to this disclosure or a pharmaceutical composition as described herein. In certain embodiments, the method can comprise sequential administration of the further therapy, wherein the further therapy can be administered after administering the oncolytic vaccinia virus according to this disclosure or a pharmaceutical composition as described herein.

In certain embodiments, the method can comprise determining the level of STAT3 before (step i) and after (step iii) administration of the oncolytic vaccinia virus or the pharmaceutical composition, alone or in combination with a further therapy, wherein the oncolytic vaccinia virus can be determined to be infective when the level of STAT3 is lower in step (iii) than in step (i).

In certain embodiments, the method can comprise the administration of the oncolytic vaccinia virus according to this disclosure or a pharmaceutical composition as described herein, wherein the oncolytic vaccinia virus or the pharmaceutical composition can be administered at a dosage that can comprise about $10^6$ PFU/mL to about $10^8$ PFU/mL of the oncolytic vaccinia virus. In certain embodiments, the method can comprise the administration of the oncolytic vaccinia virus according to this disclosure or a pharmaceutical composition as described herein, wherein the oncolytic vaccinia virus or the pharmaceutical composition can be administered, independently, in an initial dose for a first period of time, an intermediate dose for a second period of time, and a high dose for a third period of time. In certain embodiments, the method can comprise administration of the initial, the intermediate, and the high dose, independently, wherein the initial dose can be lower than the intermediate dose and the intermediate dose is lower than the high dose. In certain embodiments, the first, second, and third periods of time can each be from about 1 week to about 3 weeks. In certain embodiments, the method can comprise administering the oncolytic vaccinia virus according to this disclosure or a pharmaceutical composition as described herein, wherein the oncolytic vaccinia virus and the pharmaceutical composition can independently comprise a liquid dosage form that can be administered at a volume of about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL. In certain embodiments, the method can comprise administering the oncolytic vaccinia virus according to this disclosure or a pharmaceutical composition as described herein, wherein the oncolytic vaccinia virus or the pharmaceutical composition can be administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof. In certain embodiments, the method can comprise administering the oncolytic vaccinia virus according to this disclosure or a pharmaceutical composition as described herein, wherein the oncolytic vaccinia virus or the pharmaceutical composition can be administered for a duration of about 1 week, about 2 week, about 3 weeks, about 4 weeks, about 6 weeks, about 7 weeks, about 8 weeks, about 9 weeks, about 10, weeks, or about 12 weeks. In certain embodiments, the method can comprise administering the oncolytic vaccinia virus according to this disclosure or a pharmaceutical composition as described herein, wherein the oncolytic vaccinia virus or the pharmaceutical composition can be administered once daily, twice daily, once every week, once every two weeks, or once every three weeks. In certain embodiments, the method can comprise administering the oncolytic vaccinia virus according to this disclosure or a pharmaceutical composition as described herein, wherein the oncolytic vaccinia virus or the pharmaceutical composition can be administered intravenously or by an intratumoral injection. In certain embodiments, the method can comprise administering the oncolytic vaccinia virus according to this disclosure or a pharmaceutical composition as described herein, wherein the administration of the oncolytic vaccinia virus or the pharmaceutical composition can result in a first peak viral load after about 1 hour to about 3 days and a second peak viral load after about 3 days to about 7 days from administration of a first dose. In certain embodiments, the method can comprise administration of the further therapy, wherein the further therapy can be administered for a duration of about 1 week, about 2 week, about 3 weeks, about 4 weeks, about 6 weeks, about 7 weeks, about 8 weeks, about 9 weeks, about 10, weeks, or about 12 weeks. In certain embodiments, the method can comprise administration of the further therapy, wherein the further therapy can be administered once daily, once every week, once every two weeks, or once every three weeks. In certain embodiments, the method can comprise administration of the further therapy, wherein the further therapy can be administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof. In certain embodiments, the method can comprise administration of the further therapy, wherein the further therapy can be administered orally, intravenously, by an intratumoral injection, or by radiation. In certain embodiments, the method can comprise the administration of the oncolytic vaccinia virus according to this disclosure or a pharmaceutical composition as described herein, to a subject in need thereof, wherein the subject can be human. In certain embodiments, the method can comprise collection of the first and the second biological samples from the subject, wherein the first and the second biological samples can be human tissue samples. In certain embodiments, the method can comprise collection of the first and the second biological samples from the subject, wherein the subject can be human and the first and the second biological samples can be blood or plasma from the human subject. In certain embodiments, the method can comprise the administration of the oncolytic vaccinia virus according to this disclosure, or the pharmaceutical composition as described herein, to the subject in need thereof, wherein prior to administration of the oncolytic vaccinia virus or the pharmaceutical composition the subject may have been diagnosed with a cancer or a tumor. In certain embodiments, the method can comprise the administration of the oncolytic vaccinia virus according to this disclosure or a pharmaceutical composition as described herein, to the subject in need thereof, wherein prior to administration of the oncolytic vaccinia virus or the pharmaceutical composition the subject can be diagnosed with a cancer or a tumor. In certain embodiments, the method can comprise the administration of the oncolytic vaccinia virus according to this disclosure or a pharmaceutical composition as described herein, to the subject in need thereof in combination with the further therapy, wherein prior to administration of the oncolytic vaccinia virus or the pharmaceutical composition or the further therapy the subject may have been diagnosed with a cancer or a tumor. In certain embodiments, the method comprises the administration of the oncolytic vaccinia virus according to this disclosure or a pharmaceutical composition as described herein, to the subject in need thereof in combination with the further therapy, wherein prior to administration of the oncolytic vaccinia virus or the pharmaceutical composition the subject may have been diagnosed with a cancer or a tumor.

One non-limiting embodiment provides a virus comprising an exogenous nucleic acid, wherein said exogenous nucleic acid can encode a protein or a fragment thereof that can modulate STAT3-mediated gene-activation. In certain embodiments, the virus can comprise the exogenous nucleic acid sequence, wherein said virus can be a vaccinia virus. In certain embodiments, the virus can comprise the exogenous nucleic acid, wherein the oncolytic vaccinia virus can be an oncolytic vaccinia virus. In certain embodiments, the protein or the fragment thereof can be a PIAS3 protein or a fragment thereof. In certain embodiments, the virus can comprise the exogenous nucleic acid coding for the PIAS3 protein or a fragment thereof, wherein the exogenous nucleic acid can be at least about 85%, at least about 90%, at least about 95%, at least about 96%, at least about 97%, at least about 98%, at least about 99%, or 100% homologous to a nucleic acid sequence selected from the group consisting of SEQ ID NOs: 8-10 and 40-43, or a fragment thereof. In certain embodiments, the virus can comprise the exogenous nucleic acid coding for the PIAS3 protein or a fragment thereof, wherein PIAS3 protein or the fragment thereof can comprise an amino acid sequence that can be at least about 85%, about 90%, about 95%, about 96%, about 97%, about 98%, about 99%, or 100% homologous to an amino acid fragment from any one of SEQ ID NOs: 1-7 and 24-27, or a fragment thereof.

In certain embodiments, the oncolytic vaccinia virus can comprise an exogenous nucleic acid sequence that can encode a PIAS3 protein or a fragment thereof that can comprise amino acids 400-528 of the amino acid sequence of SEQ ID NO: 1 and conservative substitutions thereof. In certain embodiments, the oncolytic vaccinia virus can comprise an exogenous nucleic acid sequence that can encode a PIAS3 protein or a fragment thereof that can comprise amino acids 400-523 of the amino acid sequence of SEQ ID NO: 6 and conservative substitutions thereof.

In certain embodiments, the protein or a fragment thereof that modulates STAT3 activity, e.g., modulate STAT3-mediated gene-activation, can be a SOCS3 protein or a fragment thereof and conservative substitutions thereof. In certain embodiments, the exogenous nucleic acid can comprise a SOCS3 protein or a fragment thereof comprises a human SOCS3 protein or a fragment thereof and conservative substitutions thereof. In certain embodiments, the SOCS3 protein or the fragment thereof can comprise an amino acid sequence that is at least about 85% homologous to an amino acid sequence selected from the group consisting of SEQ ID NOs: 28 and 30 and conservative substitutions thereof. In certain embodiments, the SOCS3 protein or the fragment thereof can comprise an amino acid sequence that can be at least about 85% homologous to the amino acid sequence of SEQ ID NO: 28 and conservative substitutions thereof. In certain embodiments, the SOCS3 protein or the fragment thereof can comprise an amino acid sequence that can be at least about 85% homologous to the entire length of an amino acid sequence selected from the group consisting of SEQ ID NOs: 28 and 30 and conservative substitutions thereof. In certain embodiments, the SOCS3 protein or the fragment thereof comprises an amino acid sequence that can be at least about 85% homologous to a fraction of the entire length of an amino acid sequence selected from the group consisting of SEQ ID NOs: 28 and 30 and conservative substitutions thereof.

In certain embodiments, the exogenous nucleic acid that can encode a protein or a fragment thereof that modulates STAT3 activity, e.g., modulate STAT3-mediated gene-activation, can be a TCPTP protein or a fragment thereof and conservative substitutions thereof. In certain embodiments, the exogenous nucleic acid can comprise a TCPTP protein or the fragment thereof, wherein the TCPTP protein or the fragment thereof is a human TCPTP protein or a fragment thereof and conservative substitutions thereof. In certain embodiments, the TCPTP protein or the fragment thereof can comprise an amino acid sequence that can be at least about 85% homologous to an amino acid sequence selected from the group consisting of SEQ ID NOs: 32 and 34 and conservative substitutions thereof. In certain embodiments, the TCPTP protein or the fragment thereof can comprise an amino acid sequence that can be at least about 85% homologous to the amino acid sequence of SEQ ID NO: 32 and conservative substitutions thereof. In certain embodiments, the TCPTP protein or the fragment thereof can comprise an amino acid sequence that can be at least about 85% homologous to the entire length of an amino acid sequence selected from the group consisting of SEQ ID NOs: 32 and 34 and conservative substitutions thereof. In certain embodiments, the TCPTP protein or the fragment thereof can comprise an amino acid sequence that can be at least about 85% homologous to a fraction of the entire length of an amino acid sequence selected from the group consisting of SEQ ID NOs: 32 and 34 and conservative substitutions thereof.

In certain embodiments, the protein or a fragment thereof that modulates STAT3 activity, e.g., modulate STAT3-mediated gene-activation, can be a dominant-negative mutant STAT3 protein or a fragment thereof and conservative substitutions thereof. In certain embodiments, the dominant-negative mutant STAT3 protein or the fragment thereof can be a human dominant-negative mutant STAT3 protein or a fragment thereof and conservative substitutions thereof. In certain embodiments, the dominant-negative mutant STAT3 protein or the fragment thereof can comprise an amino acid sequence that can be at least about 85% homologous to an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to the entire length of an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to a fraction of the entire length of an amino acid sequence selected from the group consisting of SEQ ID NOs: 36 and 38 and conservative substitutions thereof.

In certain embodiments, the exogenous nucleic acid can further encode a cell-penetrating protein, wherein the cell-penetrating protein comprises a TAT protein of HIV-1 or a fragment thereof, YopM, transportan, penetratin, poly-arginine, or any combinations thereof. In certain embodiments, the exogenous nucleic acid can further encode the cell-penetrating protein, wherein the exogenous nucleic acid further comprises a sequence that can be at least about 85%, at least about at least 90%, at least about 95%, at least about 96%, at least about 97%, at least about 98%, at least about 99%, or 100% homologous to SEQ ID NO: 12, 13, 115, 17, 19, 21 and 23, or fragments thereof. In certain embodiments, the nucleic acid can further encode a cell-penetrating protein, wherein the exogenous nucleic acid can further comprise a sequence that can be at least about 85%, at least about 90%, at least about 95%, at least about 96%, at least about 97%, at least about 98%, at least about 99%, or 100% homologous to the entire length of SEQ ID NO: 12, 13, 115, 17, 19, 21 and 23. In certain embodiments, the exogenous nucleic acid can further encode the cell-penetrating protein, wherein the exogenous nucleic acid can further comprises a sequence that can be at least about 85%, at least about 90%, at least about 95%, at least about 96%, at least about 97%, at least about 98%, at least about 99%, or 100% homologous to a fraction of the length of SEQ ID NO: 12, 13, 115, 17, 19, 21 and 23. In certain embodiments, the exogenous nucleic acid can encode the cell-penetrating peptide or the fragment thereof, wherein the cell-penetrating peptide or the fragment thereof can comprise a sequence that is at least about 85%, at least about 90%, at least about 95%, at least about 96%, at least about 97%, at least about 98%, at least about 99%, or 100% identical to SEQ ID NO: 11, 14, 16, 18, 20 and 22 and conservative substitutions thereof, or a fragment thereof and conservative substitutions thereof. In certain embodiments, the protein or the fragment thereof that modulates STAT3 activity can be conjugated to a cell-penetrating peptide having an amino acid that can be at least about 85% homologous to the amino acid sequence of SEQ ID NO: 11.

In certain embodiments, the protein or the fragment thereof that modulates STAT3 activity can be conjugated to a cell-penetrating peptide comprising the amino acid sequence of SEQ ID NO: 11. In certain embodiments, the protein or the fragment thereof can comprise the blocking fragment, wherein the blocking fragment can comprise amino acids 126-176 of SEQ ID NO: 1. In certain embodiments, the protein or the fragment thereof can comprise the PIAS3 protein or the fragment thereof, wherein the PIAS3 protein or the fragment thereof can comprise amino acids 129-316, 133-316, 132-177, 126-176 or 400-528 of SEQ ID NO: 1.

In certain embodiments, the protein or a fragment thereof that can modulate STAT3-mediated gene-activation can be a STAT3 inhibitor.

In certain non-limiting methods of the present disclosure, the subject can be administered a ketogenic diet prior to, concurrently, or following administration of the oncolytic vaccinia virus according to this disclosure, or the pharmaceutical composition as described herein.

In certain embodiments, the oncolytic vaccinia virus comprises an exogenous nucleic acid, wherein the exogenous nucleic acid can comprise a nucleic acid fragment that can comprise a non-contiguous stretch of nucleotides from a nucleotide sequence that can be selected from the group consisting of from a nucleotide sequence selected from the group consisting of SEQ ID NOs: 8-10, 29, 31, 33, 35, 37 and 39-43. In certain embodiments, the oncolytic vaccinia virus comprises an exogenous nucleic acid, wherein the exogenous nucleic acid can comprise the nucleotide sequence of SEQ ID NO: 8. In certain embodiments, the oncolytic vaccinia virus can comprise an exogenous nucleic acid, wherein the exogenous nucleic acid can comprise the nucleotide sequence of SEQ ID NO: 9. In certain embodiments, the oncolytic vaccinia virus comprises an exogenous nucleic acid, wherein the exogenous nucleic acid can comprise the nucleotide sequence of SEQ ID NO: 10. In certain embodiments, the oncolytic vaccinia virus comprises an exogenous nucleic acid, wherein the exogenous nucleic acid can comprise the nucleotide sequence of SEQ ID NO: 29. In certain embodiments, the oncolytic vaccinia virus can comprise an exogenous nucleic acid, wherein the exogenous nucleic acid can comprise the nucleotide sequence of SEQ ID NO: 31. In certain embodiments, the oncolytic vaccinia virus comprises an exogenous nucleic acid, wherein the exogenous nucleic acid can comprise the nucleotide sequence of SEQ ID NO: 33. In certain embodiments, the oncolytic vaccinia virus comprises an exogenous nucleic acid, wherein the exogenous nucleic acid can comprise the nucleotide sequence of SEQ ID NO: 35. In certain embodiments, the oncolytic vaccinia virus comprises an exogenous nucleic acid, wherein the exogenous nucleic acid can comprise the nucleotide sequence of SEQ ID NO: 37. In certain embodiments, the oncolytic vaccinia virus comprises an exogenous nucleic acid, wherein the exogenous nucleic acid can comprise the nucleotide sequence of SEQ ID NO: 39. In certain embodiments, the oncolytic vaccinia virus comprises an exogenous nucleic acid, wherein the exogenous nucleic acid can comprise the nucleotide sequence of SEQ ID NO: 40. In certain embodiments, the oncolytic vaccinia virus comprises an exogenous nucleic acid, wherein the exogenous nucleic acid can comprise the nucleotide sequence of SEQ ID NO: 41. In certain embodiments, the oncolytic vaccinia virus comprises an exogenous nucleic acid, wherein the exogenous nucleic acid can comprise the nucleotide sequence of SEQ ID NO: 42. In certain embodiments, the oncolytic vaccinia virus comprises an exogenous nucleic acid, wherein the exogenous nucleic acid can comprise the nucleotide sequence of SEQ ID NO: 43.

DETAILED DESCRIPTION

Figure 1:
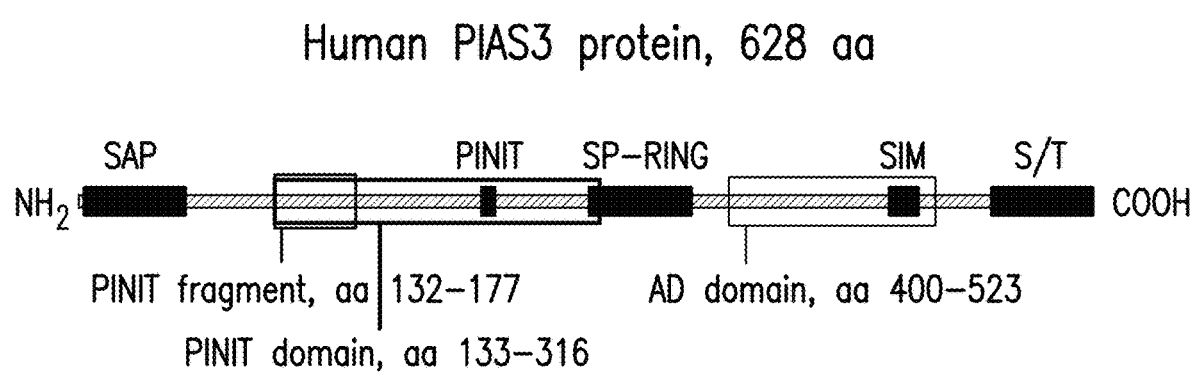
FIG. 1 shows the structural domains of PIAS3.

While preferred embodiments of this disclosure have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments of this disclosure described herein may be employed in practicing the disclosure. It is intended that the following claims define the scope of the disclosure and that methods and structures within the scope of these claims and their equivalents be covered thereby.

Certain Definitions

The terminology used herein is for the purpose of describing particular cases only and is not intended to be limiting.

As used herein, the singular forms "a", "an" and "the" can include the plural forms as well, unless the context clearly indicates otherwise. Furthermore, to the extent that the terms "contains," "containing," "including", "includes," "having," "has", "with", or variants thereof are used in either the detailed description and/or the claims, such terms are intended to be inclusive in a manner similar to the term "comprising."

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value, such as +10% of the value modified by the term "about".

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker). In certain embodiments, patients, subjects, or individuals can be under the supervision of a health care worker.

The terms "heterologous nucleic acid sequence," or "exogenous nucleic acid sequence," as used herein, in relation to a specific virus can refer to a nucleic acid sequence that originates from a source other than the specified virus.

The term "mutation," as used herein, can refer to a deletion, an insertion of a heterologous nucleic acid, an inversion or a substitution, including an open reading frame ablating mutations as commonly understood in the art.

The term "gene," as used herein, can refer to a segment of nucleic acid that encodes an individual protein or RNA (also referred to as a "coding sequence" or "coding region"), optionally together with associated regulatory regions such as promoters, operators, terminators and the like, which may be located upstream or downstream of the coding sequence.

The terms "mutant virus" and "modified virus," as used interchangeably herein, can refer to a virus comprising one or more mutations in its genome, including but not limited to deletions, insertions of heterologous nucleic acids, inversions, substitutions or combinations thereof.

The term "naturally-occurring," as used herein with reference to a virus, can indicate that the virus can be found in nature, i.e., it can be isolated from a source in nature and has not been intentionally modified.

The terms "inhibiting," "reducing" or "prevention," or any variation of these terms, referred to herein, can include any measurable decrease or complete inhibition to achieve a desired result.

A "promoter," as used herein, can be a control sequence that is a region of a nucleic acid sequence at which initiation and rate of transcription are controlled. In certain embodiments, a promoter may contain genetic elements at which regulatory proteins and molecules may bind such as RNA polymerase and other transcription factors. The terms "operatively positioned," "operatively linked," "under control" and "under transcriptional control" can mean that a promoter is in a correct functional location and/or orientation in relation to a nucleic acid sequence to control transcriptional initiation and/or expression of that sequence. In certain embodiments, a promoter may or may not be used in conjunction with an "enhancer," which refers to a cis-acting regulatory sequence involved in the transcriptional activation of a nucleic acid sequence.

The term "homology," as used herein, may be to calculations of "homology" or "percent homology" between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In certain embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search may determine homology between two sequences. The two sequences can be genes, nucleotides sequences, protein sequences, peptide sequences, amino acid sequences, or fragments thereof. The actual comparison of the two sequences can be accomplished by well-known methods, for example, but not by way of limitation, using a mathematical algorithm. A non-limiting example of such a mathematical algorithm is described in Karlin, S. and Altschul, S., Proc. Natl. Acad. Sci. USA, 90-5873-5877 (1993). Such an algorithm may be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another non-limiting embodiment, the percent identity between two amino acid sequences can be accomplished using, for example, the GAP program in the GCG software package (Accelrys, Cambridge, UK).

The term "subject" can refer to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" can be meant to include alleviating or abrogating a disorder, disease, or condition; or one or more of the symptoms associated with the disorder, disease, or condition; or alleviating or eradicating the cause(s) of the disorder, disease, or condition itself. In certain embodiments, treatment can be performed either for prophylaxis or during the course of clinical pathology. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The terms "therapeutically effective amount" or "effective amount," as used interchangeably herein, can refer to the amount of a compound that, when administered, can be sufficient to prevent development of, or alleviate to some extent, one or more of the symptoms of the disorder, disease, or condition being treated. The term "therapeutically effective amount" can also refer to the amount of a compound that is sufficient to elicit the biological or medical response of a cell, tissue, system, animal, or human that is being sought by a researcher, veterinarian, medical doctor, or clinician.

The terms "pharmaceutically acceptable carrier," "pharmaceutically acceptable excipient," "physiologically acceptable carrier," or "physiologically acceptable excipient" can refer to a pharmaceutically-acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; s, 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "pharmaceutical composition," as used herein, can refer to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

An "anti-cancer agent," as used herein, can refer to an agent or therapy that is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Non-limiting examples of anti-cancer agents can include biological agents (biotherapy), chemotherapy agents, and radiotherapy agents.

The term "oncolytic," as used herein, can refer to killing of cancer or tumor cells by an agent, such as an oncolytic vaccinia virus, e.g., through the direct lysis of said cells, by stimulating immune response towards said cells, apoptosis, expression of toxic proteins, autophagy and shut-down of protein synthesis, induction of anti-tumoral immunity, or any combinations thereof. The direct lysis of the cancer or tumor cells infected by the agent, such as an oncolytic vaccinia virus, can be a result of replication of the virus within said cells. In certain examples, the term "oncolytic," refers to killing of cancer or tumor cells without lysis of said cells.

The term "dominant-negative mutation," as used herein, can refer to a mutation in an amino acid sequence of a protein or a nucleotide sequence that encodes the protein that results in a mutated form of the protein that acts antagonistically to the wild-type form of the protein.

Modified Viruses

In certain embodiments, modified viruses, e.g., oncolytic vaccinia viruses, containing an exogenous nucleic acid sequence that encodes a modulator of STAT3 activity, e.g., STAT-3 mediated gene-activation, are provided. STAT3 can indirectly regulate several target genes by mediating expression of other transcription factors or physical association with other transcription factors to enhance or suppress their function in gene regulation. Examples of STAT3-regulated genes include, but are not limited to, p53 (NG_017013.2), Fas (NG_009089.2), Hsp70 (NC_000005.10), Cyclin-D1 (NG_007375.1), IL-10 (NG_012088.1), etc. See, e.g., Carpenter and Lo, Cancers, 2014, 6, 897-925, which is incorporated by reference herein.

In certain embodiments, viruses described herein comprise one or more exogenous nucleic acid sequences, alternatively referred to as transgenes, which can generate mRNAs coding for an agent that can modulate the activity of STAT3 and as a result can also modulate the activation of genes regulated by STAT3. Thus, certain examples provided herein provide oncolytic vaccinia viruses containing exogenous nucleic acid sequences that can encode an agent that can modulate STAT-3 mediated gene-activation. The phrase "modulates STAT3-mediated gene activation," as used herein, can refer to a process wherein STAT3 activity is modulated and as a consequence the activation of one or more genes that are regulated by STAT3 is also modulated.

In certain embodiments, the agent that can modulate STAT3-mediated gene activation is a protein or a fragment thereof. In certain embodiments, the protein or the fragment thereof can inhibit, reduce, or minimize STAT3 activity and STAT3-mediated gene activation. A protein or a fragment thereof that inhibits, reduces and/or minimizes STAT3 activity and STAT3-mediated gene activation can, for example, block the binding of STAT3 to a DNA binding sequence in the promoter regions of STAT3 responsive genes. In additional examples, the protein or a fragment thereof that inhibits, reduces, or minimizes STAT3 activity and STAT3-mediated gene activation can directly bind the STAT3 protein, for example, at the SH2 domain. In certain embodiments, a protein that inhibits, reduces and/or minimizes STAT3 activity blocks, prevents, reduces and/or minimizes the phosphorylation of STAT3 and/or dephosphorylates STAT3. In certain non-limiting embodiments, the proteins that modulate STAT3 activity can include phosphotyrosine phosphatases (PTPs), protein inhibitor of activated STAT (PIAS) and suppressor of cytokine signaling (SOCS) proteins.

In certain embodiments, the protein or the fragment thereof that inhibits, reduces, or minimizes STAT3 activity and STAT3-mediated gene activation can be a PIAS3 protein or a fragment thereof. For example, and not by way of limitation, a modified virus, e.g., an oncolytic vaccinia virus, of this disclosure can express a PIAS3 protein or a fragment thereof. In certain embodiments, the modified virus can express a human PIAS3 protein, e.g., that can comprise an amino acid sequence that is at least about 85%, about 90%, about 95%, about 96%, about 97%, about 98%, about 99% or 100% homologous to the amino acid sequence of SEQ ID NO: 1, or a fragment thereof and conservative substitutions thereof.

In certain embodiments, the modified viruses can express a mouse PIAS3 protein or a fragment thereof, e.g., that can comprise an amino acid sequence that is at least about 85%, about 90%, about 95%, about 96%, about 97%, about 98%, about 99% or 100% homologous to the amino acid sequence of SEQ ID NO: 6, or a fragment thereof and conservative substitutions thereof.

In certain embodiments, the virus can express a rat PIAS3 protein or a fragment thereof, e.g., that can comprise an amino acid sequence that is at least about 85%, about 90%, about 95%, about 96%, about 97%, about 98%, about 99% or 100% homologous to the amino acid sequence of SEQ ID NO: 7, or a fragment thereof and conservative substitutions thereof.

In certain embodiments, this disclosure provides a modified virus, e.g., an oncolytic vaccinia virus, that can express a PINIT (proline, isoleucine, asparagine, isoleucine, threonine) fragment of a PIAS3 protein. In certain embodiments, the PINIT fragment can comprise amino acids 126-176 of SEQ ID NO: 1 and conservative substitutions thereof. For example, and not by way of limitation, the PINIT fragment can comprise the amino acid sequence set forth in SEQ ID NO: 4 and conservative substitutions thereof. In certain embodiments, the PINIT fragment can comprise amino acids 132-177 of SEQ ID NO: 1 and conservative substitutions thereof. In certain embodiments, the PINIT fragment can comprise the amino acid sequence set forth in SEQ ID NO: 3 and conservative substitutions thereof.

In certain embodiments, this disclosure provides a modified virus, e.g., an oncolytic vaccinia virus, that can express the PINIT domain of a PIAS3 protein. In certain embodiments, the PINIT domain can comprise amino acids 129-316 of SEQ ID NO: 1 or conservative substitutions thereof. For example, and not by way of limitation, the PINIT domain can comprise the amino acid sequence set forth in SEQ ID NO: 5 and conservative substitutions thereof. In certain embodiments, the PINIT domain can comprise amino acids 133-316 of SEQ ID NO: 1 or conservative substitutions thereof. In certain embodiments, the PINIT domain can comprise the amino acid sequence set forth in SEQ ID NO: 2 and conservative substitutions thereof.

In certain embodiments, the present invention provides a virus, e.g., vaccinia virus, expressing the acidic domain of a human PIAS3 protein. In certain embodiments, the acidic domain comprises amino acids 400-528 of SEQ ID NO: 1 and conservative substitutions thereof. For example, and not by way of limitation, the acidic domain comprises the amino acid sequence set forth in SEQ ID NO: 24 and conservative substitutions thereof. In certain embodiments, the acidic domain of a mouse PIAS3 protein comprises amino acids 400-523 of SEQ ID NO: 6 and conservative substitutions thereof. For example, and not by way of limitation, the acidic domain comprises the amino acid sequence set forth in SEQ ID NO: 26 and conservative substitutions thereof.

In certain embodiments, this disclosure provides a modified virus, e.g., an oncolytic vaccinia virus, that can express a PIAS3 protein or a fragment thereof that can comprise an amino acid sequence that is at least about 85%, about 90%, about 95%, about 96%, about 97%, about 98%, about 99% or 100% homologous to an amino acid sequence selected from the group consisting of SEQ ID NOs: 1-7 and 24-27, or a fragment thereof and conservative substitutions thereof. In certain embodiments, the PIAS3 protein or the fragment thereof can comprise an amino acid sequence that is at least about 85%, about 90%, about 95%, about 96%, about 97%, about 98%, about 99%, or 100% homologous to the entire length of an amino acid sequence selected from the group consisting of SEQ ID NOs: 1-7 and 24-27. In certain embodiments, the PIAS3 protein or the fragment thereof can comprise an amino acid sequence that is at least about 85%, about 90%, about 95%, about 96%, about 97%, about 98%, about 99%, or 100% homologous to a fraction of the entire length of an amino acid sequence selected from the group consisting of SEQ ID NOs: 1-7 and 24-27. In additional examples, the PIAS3 protein or the fragment thereof can comprise an amino acid sequence that is at least about 85%, about 90%, about 95%, about 96%, about 97%, about 98%, about 99%, or 100% homologous to the entire length of the amino acid sequence of SEQ ID NO: 1. In yet other examples, the PIAS3 protein or the fragment thereof can comprise an amino acid sequence that is at least about 85%, about 90%, about 95%, about 96%, about 97%, about 98%, about 99%, or 100% homologous to a fraction of the entire length of the amino acid sequence of SEQ ID NO: 1. In certain embodiments, the PIAS3 protein can be further conjugated to a cell penetrating peptide, as disclosed herein, and the exogenous nucleic acid can further encode a cell penetrating peptide.

In certain embodiments, this disclosure provides a modified virus, e.g., an oncolytic vaccinia virus, that can be modified to comprise one or more heterologous nucleic acids, e.g., genes, encoding a protein or a fragment thereof that can inhibit, reduce, or minimize STAT3 activity and STAT3-mediated gene activation, as described above. In certain embodiments, this disclosure provides modified viruses, e.g., oncolytic vaccinia viruses having a nucleic acid encoding a protein that can inhibit, reduce, or minimize STAT3 activity. For example, and not by way of limitation, this disclosure provides a modified virus, e.g., an oncolytic vaccinia virus having one or more nucleic acids that can encode a PIAS3 protein or a fragment thereof (e.g., a PINIT domain or a PINIT fragment of a PIAS3 protein) as disclosed herein. In certain embodiments, the nucleic acid that can encode a PIAS3 protein can comprise a nucleotide sequence selected from the group consisting of SEQ ID NO: 8-10 and 40-43, or a fragment thereof. In certain embodiments, the nucleic acid that can encode a PIAS3 protein can comprise a nucleotide sequence that is at least about 85%, about 90%, about 95%, about 96%, about 97%, about 98%, about 99%, or 100% homologous to the entire length of a nucleic acid sequence selected from the group consisting of SEQ ID NOs: 8-10 and 40-43. In certain embodiments, the nucleic acid that can encode a PIAS3 protein can be at least about 85%, about 90%, about 95%, about 96%, about 97%, about 98%, about 99%, or 100% homologous to a fraction of a nucleic acid sequence selected from the group consisting of SEQ ID NOs: 8-10 and 40-43. In certain embodiments, the nucleic acid that can encode a PIAS3 protein can comprise the nucleotide sequence of SEQ ID NO: 8. In certain embodiments, the nucleic acid that can encode a PIAS3 protein can comprise the nucleotide sequence of SEQ ID NO: 9. In certain embodiments, the nucleic acid that can encode a PIAS3 protein can comprise the nucleotide sequence of SEQ ID NO: 10. In certain non-limiting embodiments, the nucleic acid that encodes a PIAS3 protein comprises the nucleotide sequence of SEQ ID NO: 40. In certain non-limiting embodiments, the nucleic acid that encodes a PIAS3 protein comprises the nucleotide sequence of SEQ ID NO: 41. In certain non-limiting embodiments, the nucleic acid that encodes a PIAS3 protein comprises the nucleotide sequence of SEQ ID NO: 42. In certain non-limiting embodiments, the nucleic acid that encodes a PIAS3 protein comprises the nucleotide sequence of SEQ ID NO: 43. In certain embodiments, the fragment can have a length of about 3 to about 6 nucleotides, about 6 to about 9 nucleotides, about 9 to about 12 nucleotides, about 12 to about 15 nucleotides, about 15 to about 18 nucleotides, about 18 to about 21 nucleotides, about 21 to about 24 nucleotides, about 24 to about 99 nucleotides, about 99 to about 120 nucleotides, about 120 to about 150 nucleotides, about 150 to about 153 nucleotides, about 156 nucleotides to about 573 nucleotides, about 576 nucleotides to about 600 nucleotides, or more, from a nucleotide sequence selected from the group consisting of SEQ ID NOs: 8-10 and 40-43. In certain embodiments, the fragment can comprise a contiguous stretch of nucleotides from a nucleotide sequence selected from SEQ ID NOs: 8-10 and 40-43. In certain embodiments, the fragment can comprise non-contiguous nucleotides from a nucleotide sequence selected from SEQ ID NOs: 8-10 and 40-43.

In certain embodiments, the protein or the fragment thereof that inhibits, reduces, or minimizes STAT3 activity and STAT3-mediated gene activation can be a SOCS3 protein or a fragment thereof. For example, and not by way of limitation, a modified virus, e.g., an oncolytic vaccinia virus, of this disclosure can express a SOCS3 protein or a fragment thereof. In certain embodiments, the modified virus can express a human SOCS3 protein, e.g., that can comprise an amino acid sequence that is at least about 85%, at least about 90%, at least about 95%, at least about 96%, at least about 97%, at least about 98%, at least about 99% or 100% homologous to the amino acid sequence of SEQ ID NO: 28 or 30, or a fragment thereof and conservative substitutions thereof. In certain embodiments, the modified viruses can comprise an exogenous nucleic acid that can express a SOCS3 protein or a fragment thereof, wherein said nucleic acid can comprise a nucleotide sequence that is at least about 85%, about 90%, about 95%, about 96%, about 97%, about 98%, about 99% or 100% homologous to the amino acid sequence of SEQ ID NO: 29 or 31, or a fragment thereof. In certain embodiments, the SOCS3 protein or the fragment thereof can comprise an amino acid sequence that is at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 28 and 30. In certain embodiments, the SOCS3 protein or the fragment thereof can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 28 and 30. In certain embodiments, the SOCS3 protein can be further conjugated to a cell penetrating peptide, as disclosed herein, and the exogenous nucleic acid can further encode a cell penetrating peptide.

In certain embodiments, the protein or the fragment thereof that inhibits, reduces, or minimizes STAT3 activity and STAT3-mediated gene activation can be a TCPTP protein or a fragment thereof. For example, and not by way of limitation, a modified virus, e.g., an oncolytic vaccinia virus, of this disclosure can express a TCPTP protein or a fragment thereof. In certain embodiments, the modified virus can express a human TCPTP protein, e.g., that can comprise an amino acid sequence that is at least about 85%, at least about 90%, at least about 95%, at least about 96%, at least about 97%, at least about 98%, at least about 99% or 100% homologous to the amino acid sequence of SEQ ID NO: 32 or 34, or a fragment thereof, and conservative substitutions thereof. In certain embodiments, the modified viruses can comprise an exogenous nucleic acid that can express a TCPTP protein or a fragment thereof, wherein said nucleic acid can comprise a nucleotide sequence that is at least about 85%, at least about 90%, at least about 95%, at least about 96%, at least about 97%, at least about 98%, at least about 99% or 100% homologous to the amino acid sequence of SEQ ID NO: 33 or 35, or a fragment thereof. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 32 and 34. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 32 and 34. In certain embodiments, the TCPTP protein can be further conjugated to a cell penetrating peptide, as disclosed herein, and the exogenous nucleic acid can further encode a cell penetrating peptide.

In certain embodiments, the protein or the fragment thereof that inhibits, reduces, or minimizes STAT3 activity and STAT3-mediated gene activation can be a STAT3 protein. For example, and not by way of limitation, a modified virus, e.g., an oncolytic vaccinia virus, of this disclosure can express a STAT3 protein or a fragment thereof. In certain embodiments, the modified virus can express a human STAT3 protein, e.g., that can comprise an amino acid sequence that is at least about 85%, at least about 90%, at least about 95%, at least about 96%, at least about 97%, at least about 98%, at least about 99% or 100% homologous to the amino acid sequence of SEQ ID NO: 36 or 38, or a fragment thereof and conservative substitutions thereof. In certain embodiments, the modified viruses can comprise an exogenous nucleic acid that can express a STAT3 protein or a fragment thereof, wherein said nucleic acid can comprise a nucleotide sequence that is at least about 85%, at least about 90%, at least about 95%, at least about 96%, at least about 97%, at least about 98%, at least about 99% or 100% homologous to the amino acid sequence of SEQ ID NO: 37 or 39, or a fragment thereof. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 36 and 38. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 36 and 38. In certain embodiments, the STAT3 protein can be further conjugated to a cell penetrating peptide, as disclosed herein, and the exogenous nucleic acid can further encode a cell penetrating peptide.

In certain embodiments, the nucleic acid can be operably linked to a promoter element, such as a promoter element endogenous to the virus or, alternatively, an introduced exogenous promoter. In certain embodiments, the promoter is a high-expression viral promoter including, but not limited to, the synthetic vaccinia virus promoter "P11 late" derived from the vSC8 vaccinia strain or the "synthetic early/late promoter" derived from the vSC56 vaccinia strain. In certain embodiments, the promoter can be a low-expression viral promoter including, but not limited to, the "P7.5 early/late" promoter derived from the vGK vaccinia strain.

In certain embodiments, the exogenous nucleic acid that can encode a protein or fragment thereof that can modulate STAT3 activity and STAT3-mediated gene activation can independently be inserted at any location of the viral genome, for example in a non-essential locus. Insertion into the oncolytic virus can be performed by routine molecular biology, e.g., as described in Sambrook et al. (2001, Molecular Cloning-A Laboratory Manual, Cold Spring Harbor Laboratory). Insertion into an adenoviral vector or a poxviral vector can be performed through homologous recombination as described respectively in Chartier et al. (1996, J. Virol. 70: 4805-10) and Paul et al. (2002, Cancer gene Ther. 9: 470-7). For example, TK, RR and F2L genes as well as intergenic regions are exemplary loci appropriate for insertion in oncolytic vaccinia virus and E3 and E4 regions for insertion in an oncolytic virus. In certain embodiments, the nucleic acid is inserted at the J2R locus which encodes the thymidine kinase (TK) enzyme resulting in the disruption of the TK locus.

Some non-limiting embodiments of this disclosure provides a modified vaccinia virus that can comprise a nucleic acid that can encode a PIAS3 protein or a fragment thereof, a SOCS3 protein or a fragment thereof, a TCPTP protein or a fragment thereof, or a STAT3 protein comprising one or more dominant-negative mutations, where the nucleic acid can be inserted in the TK gene, resulting in thymidine kinase inactivation. Alternatively, the nucleic acid can be inserted within any non-essential gene within the viral genome or within any intragenic region within the virus genome.

In certain embodiments, the exogenous nucleic acid encoding a PIAS3 protein or a fragment thereof can further encode a cell-penetrating peptide. For example, and not by way of limitation, the cell-penetrating peptide can be derived from the HIV-1 tat gene. In certain embodiments, the cell-penetrating peptide can include $TAT_{47-57}$ of NCBI/UniProtKB Accession No. NP 057853.1, which has the amino acid sequence YGRKKRRQRRR (SEQ ID NO: 11), e.g., derived from nucleotide residues 5515-5547 of the HIV-1 genome (set forth in NCB1/UniProtKB Accession No. NC 001802.1), which has the nucleotide sequence TATGGCAGGAAGAAGCGGAGACAGCGACGAAGA (SEQ ID NO: 12). In certain embodiments, the nucleic acid that encodes a TAT protein can comprise a nucleotide sequence that can be at least about 85%, about 90%, about 95%, about 96%, about 97%, about 98%, about 99%, or 100% homologous to the entire length of SEQ ID NO: 12. In certain embodiments, the nucleic acid that can encode a TAT protein is at least about 85%, about 90%, about 95%, about 96%, about 97%, about 98%, about 99%, or 100% homologous to a fraction of the entire length of SEQ ID NO: 12. In certain embodiments, the amino sequence of SEQ ID NO: 11 is encoded by the nucleotide sequence TATGGACGAAAAAAACGACGACAACGACGACGA (SEQ ID NO: 13). In certain embodiments, the cell-penetrating peptide can include can be derived from the HIV-1 tat gene and have the nucleotide sequence CGACAACGACGAAAGAAGCGAGGT (SEQ ID NO: 14), which encodes a peptide having the amino acid sequence RQRRKKRG (SEQ ID NO: 15).

In certain embodiments, the cell-penetrating peptide can be an N-terminal domain (NTD) of the *Yersinia pestis* virulence effector YopM having the amino acid sequence KSKTEYYNAWSEWERNAPPGNGEQREMAVSRLRD-CLDRQA (SEQ ID NO: 16). In certain embodiments, the YopM NTD cell-penetrating peptide has the nucleotide sequence

```
                                    (SEQ ID NO: 17)
AAGAGTAAGACGGAGTATTACAATGCTTGGTCAGAGTGGGAGCGAAACGC

CCCTCCAGGCAATGGGGAGCAGCGAGAGATGGCGGTGAGTCGGTTGAGGG

ACTGTCTCGACAGGCAGGCA.
```

In certain embodiments, the cell-penetrating peptide can be transportan having the amino acid sequence GWTLN-SAGYLLGKINLKALAALAKKIL (SEQ ID NO: 18). In certain embodiments, the transportan cell-penetrating peptide is encoded by the nucleotide sequence

```
                                    (SEQ ID NO: 19)
GGCTGGACACTTAACAGCGCAGGATATTTGCTTGGCAAAATCAATTTGAA

GGCCTTGGCTGCGCTTGCAAAAAAATTCTC.
```

In certain embodiments, the cell-penetrating peptide can be penetratin having the amino acid sequence RQIKIWFQNRRMKWKK (SEQ ID NO: 20). In certain embodiments, the penetratin cell-penetrating peptide is encoded by the nucleotide sequence

```
                                    (SEQ ID NO: 21)
CGGCAGATAAAAATCTGGTTCCAGAATCGGCGCATGAAATGGAAGAAA.
```

In certain embodiments, the cell-penetrating peptide can be poly-arginine having the amino acid sequence RRRRRRRRRHHHHHH (SEQ ID NO: 22), e.g., see SEQ ID NOs: 25 and 27. In certain embodiments, the polyarginine cell-penetrating peptide is encoded by the nucleotide sequence (SEQ ID NO: 23)
AGGCGGCGAAGACGCCGCAGGAGACGGCACCACCATCACCATCAC.

In certain embodiments, the cell-penetrating peptide can be conjugated to the PIAS3 protein or a fragment thereof placed either directly at or in close proximity to the N- or C-terminal of a PIAS3 gene construct. In certain embodiments, the cell-penetrating peptide can be conjugated to the SOCS3 protein or a fragment thereof placed either directly at or in close proximity to the N- or C-terminal of a SOCS3 gene construct. In certain embodiments, the cell-penetrating peptide can be conjugated to the TCPTP protein or a fragment thereof placed either directly at or in close proximity to the N- or C-terminal of a TCPTP gene construct. In certain embodiments, the cell-penetrating peptide can be conjugated to the TCPTP protein or a fragment thereof placed either directly at or in close proximity to the N- or C-terminal of a dominant-negative STAT3 nucleic acid construct.

In certain embodiments, the above-described modifications may be produced in any virus that is known in the art. For instance, a vaccinia virus that is known in the art can be modified as described above to be used in this disclosure. Non-limiting examples include the Western Reserve (WR) strain, Copenhagen strain, Wyeth (NYCBOH) strain, Tian Tian strain or USSR strain. In certain embodiments, the above-described modifications may be produced in a virus such as, but not limited to, other poxviruses, HSV, Adenovirus, Reovirus, Newcastle Disease Virus, Measles virus, Maraba virus, Vesicular Stomatitis Virus, AAV and retroviruses. In certain embodiments, the modified vaccinia viruses disclosed herein are of the WR strain. The base vaccinia virus strain modified as set forth herein can itself comprise one or more mutations relative to its parent strain, for example, but not limited to, one or more of the following: deletion in TK; deletion in VGF; SPI-1 deletion; and SPI-2 deletion. In alternative embodiments, the oncolytic virus of the present disclosure can be a vaccinia virus comprising defective TK and Ribonucleotide reductase (RR) activities, where the RR defect results from inactivating mutations in the I4L and/or F4L gene(s) carried by the viral genome. In another non-limiting embodiment, the oncolytic virus of the present disclosure can be a vaccinia virus defective for dUTPase resulting from inactivating mutations in the F2L gene of the viral genome, alone or in combination with disruption of at least one of TK and RR activities or both. In certain embodiments, the vaccinia virus strain can also include a mutation and/or deletion in B8R (IFN gamma binding protein; e.g., see Symons et al., 1995, Cell. 81(4): 551-60); B18R (type I IFN binding protein; e.g., see Colamonici et al., 1995, J. Biol. Chem. 270(27):15974-8); B15R (IL-1β binding protein; e.g., see Alcami et al., 1992, Cell. 71(1):153-67); IL-18BP (e.g., a C12L deletion); B5R (e.g., B5R deletion); and/or C16 (e.g., C16L deletion; see Fahy et al., 2008, J. Gen. Virol. 89:2377-2387). See, also, WO 2015/027163, which is hereby incorporated by reference in its entirety.

Vaccinia viruses usually produce four virion forms, including the single-enveloped intracellular mature virion (IMV), triple-enveloped intracellular enveloped virion (IEV), and the double enveloped cell-associated enveloped virion (CEV) and extracellular enveloped virion (EEV). The EEV form can be associated with long-range virus dissemination. In certain embodiments of this disclosure, a population of oncolytic viruses as describe herein can predominantly comprise the EEV form. In certain embodiments, the disclosed modified vaccinia viruses replicate within M2 macrophages in tumor cells. For example, and not by way of limitation, the vaccinia virus replicates within the M2 macrophages in tumor cells to produce a population of viruses that predominantly contains extracellular enveloped viruses (EEVs). In certain embodiments, the vaccinia virus partially avoids immunosuppression by replicating within the M2 macrophages.

PIAS3 (Protein Inhibitor of Activated STAT3; Denoted PIAS3 Herein)

In certain embodiments, a PIAS3 protein may be a human PIAS3 protein having an amino acid sequence as set forth in NCBI/UniProtKB Accession No. NP 006090.2 or an amino acid sequence at least about 95 percent or at least about 98 percent homologous thereto.

In certain embodiments, a PIAS3 protein can comprise an amino acid sequence that has the sequence of SEQ ID NO: 1, set forth below:
MAELGELKHMVMSFRVSELQVLLGFAGRNKS-GRKHELLAKALHLLKSSCAPSVQM KIKELYRRRF-PRKTLGPSDLSLLSLPPGTSPVGSPGPLAPIPPTL-LAPGTLLGPKREVD MHPPLPQPVHPDVTMKPLPFYEVYGELIRPTTLAST-SSQRFEEAHFTFALTPQQVQQI LTSREVLPGAKCDY-TIQVQLRFCL-CETSCPQEDYFPPNLFVKVNGKLCPLPGYLPPTK NGAEPKRPSRPINITPLARLSATVPNTIV-VNWSSEFGRNYSLSVYLVRQLTAGTLLQK LRAK-GIRNPDHSRALIKEKLTADPDSEVATT-SLRVSLMCPLGKMRLTVPCRALTCAH LQSFDAALYLQMNEKKPTWTCPVCDKKAPYESLI-IDGLFMEILSSCSDCDEIQFMED GSWCPMKPKKEAS-EVCPPPGYGLDGLQYSPVQGGDPSENKKKVEVI-DLTIESSSDEE DLPPTKKHCSVTSAAIPALPGSKGVLTSGHQPSSVLR-SPAMGTLGGDFLSSLPLHEYP PAFPLGADIQGLDLF-SFLQTESQHYGPSVITSLDEQDALGHFFQYRGTP-SHFLGPLAPT LGSSHCSATPAPPPGRVSSIVAPGGALREGHGG-PLPSGPSLTGCRSDIISLD (SEQ ID NO: 1) or an amino acid sequence at least about 95 percent or at least about 98 percent homologous thereto.

In certain embodiments, a PIAS3 protein of this disclosure can have an amino acid sequence that is a consecutive a fragment of SEQ ID NO: 1, which is at least 20, or at least 30, or at least 40, or at least 50, or at least 60, or at least 70, or at least 80, or at least 90 or at least 100 or at least 200 amino acids or more in length, or an amino acid sequence at least about 95 percent or at least about 98 percent homologous thereto.

In certain embodiments, a PIAS3 protein can comprise amino acids 133-316 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 2, as set forth below:
PFYEVYGELIRPTTLASTSSQRFEEAHFTFAL-TPQQVQQILTSREVLPGAKCDYTIQVQ LRFCL-CETSCPQEDYFPPNLFVKVNGKLCPLPGYLPPTKN-GAEPKRPSRPINITPLARLS ATVPNTIVVNWSSEFGRNYSLSVYLVRQLT-AGTLLQKLRAKGIRNPDHSRALIKEKLT ADPDSEV (SEQ ID NO: 2) or an amino acid sequence at least about 95 percent or at least about 98 percent homologous thereto.

In certain embodiments, a PIAS3 protein can comprise amino acids 132-177 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 3, as set forth below:
LPFYEVYGELIRPTTLASTSSQRFEEAHFTFAL-TPQQVQQILTSRE (SEQ ID NO: 3) or an amino acid sequence at least about 95 percent or at least about 98 percent homologous thereto.

In certain embodiments, a PIAS3 protein can comprise amino acids 126-176 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 4, as set forth below:
DVTMKPLPFYEVYGELIRPTTLASTSSQRFEEAHFT-FALTPQQVQQILTSR (SEQ ID NO: 4) or an amino acid sequence at least about 95 percent or at least about 98 percent homologous thereto.

In certain embodiments, a PIAS3 protein can comprise amino acids 129-316 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 5, as set forth below:
MKPLPFYEVYGELIRPTTLASTSSQRFEEAHFTFAL-TPQQVQQILTSREVLPGAKCDYT IQVQLRFCL-CETSCPQEDYFPPNLFVKVNGKLCPLPGYLPPTKN-GAEPKRPSRPINITPL ARLSATVPNTIVVNWSSEFGRNYSLSVYLVRQLT-AGTLLQKLRAKGIRNPDHSRALIK EKLTADPDSEV (SEQ ID NO: 5) or an amino acid sequence at least about 95 percent or at least about 98 percent homologous thereto.

In certain embodiments, a PIAS3 protein comprises amino acids 400-528 of SEQ ID NO: 1 or an amino acid sequence at least about 95 percent or at least about 98 percent homologous thereto. For example, and not by way of limitation, the PIAS3 protein comprises the amino acid sequence of SEQ ID NO: 24, as set forth below:
MEDGSWCPMKPKKEASEVCPPPGYGLDG-LQYSPVQGGDPSENKKKVEVIDLTIESSS DEEDLPPTKKHCSVTSAAIPALPGSKGVLT-SGHQPSSVLRSPAMGTLGGDFLSSLPLHE YPPAFPLG (SEQ ID NO: 24) or an amino acid sequence at least about 95 percent or at least about 98 percent homologous thereto. In certain embodiment, the C-terminus of a PIAS3 protein can be modified to include a poly-arginine cell-penetrating peptide comprising the amino acid sequence RRRRRRRR-RHHHHHH (SEQ ID NO: 22). For example, and not by way of limitation, a PIAS3 protein conjugated to a poly-arginine cell-penetrating peptide comprises the amino acid sequence of SEQ ID NO: 25, as set forth below:
MEDGSWCPMKPKKEASEVCPPPGYGLDG-LQYSPVQGGDPSENKKKVEVIDLTIESSS DEEDLPPTKKHCSVTSAAIPALPGSKGVLT-SGHQPSSVLRSPAMGTLGGDFLSSLPLHE YPPAFPL-GRRRRRRRRRHHHHHH (SEQ ID NO: 25) or an amino acid sequence at least about 95 percent or at least about 98 percent homologous thereto.

In certain embodiments, a PIAS3 protein may be a mouse PIAS3 protein having an amino acid sequence as set forth in NCBI/UniProtKB Accession No. NP_001159421.1 or an amino acid sequence at least about 95 percent or at least about 98 percent homologous thereto. For example, and not by way of limitation, the mouse PIAS3 protein comprises the amino acid sequence of SEQ ID NO: 6, as set forth below:
MAELGELKHMVMSFRVSELQVLLGFAGRNKS-GRKHELLAKALHLLKSSCAPSVQM KIKELYRRRF-PRKTLGPSDLSLLSLPPGTSPVGSPG-PLAPIPPTLLTPGTLLGPKREVDM HPPLPQPVHPDVTMKPLPFYEVYGELIRPTTLAST-SSQRFEEAHFTFALTPQQLQQILTS REVLPGAKCDY-TIQVQLRFCL-CETSCPQEDYFPPNLFVKVNGKLCPLPGYLPPTKNGA EPKRPSRPINITPLARLSATVPNTIVVNWSSEFGRNYS-LSVYLVRQLTAGTLLQKLRAK GIRNPDHSRA-LIKEKLTADPDSEVATT-SLRVSLMCPLGKMRLTVPCRALTCAHLQSFD AALYLQMNEKKPTWTCPVCDKKAPYESLIIDG-LFMEILNSCSDCDEIQFMEDGSWCP MKPKKEAS-EVCPPPGYGLDGLQYSAVQEGIQPESKKRVEVI-DLTIESSSDEEDLPPTKK HCPVTSAAIPALPGSKGALTSGHQPSSVLRS-PAMGTLGSDFLSSLPLHEYPPAFPLGAD IQGLDLF-SFLQTESQHYGPSVITSLDEQDTLGHFFQYRGTP-SHFLGPLAPTLGSSHRSST PAPPPGRVSSIVAPGSSLREGHGGPLPSGPSLTGCRSD-VISLD (SEQ ID NO: 6) or an amino acid sequence at least about 95 percent or at least about 98 percent homologous thereto.

In non-limiting embodiments, a PIAS3 protein of the present invention can have an amino acid sequence that is a consecutive portion of SEQ ID NO: 6, which is at least 20, or at least 30, or at least 40, or at least 50, or at least 60, or at least 70, or at least 80, or at least 90 or at least 100 or at least 200 amino acids or more in length, or an amino acid sequence at least about 95 percent or at least about 98 percent homologous thereto.

In certain embodiments, a mouse PIAS3 protein comprises amino acids 400-523 of SEQ ID NO: 6 or an amino acid sequence at least about 95 percent or at least about 98 percent homologous thereto. For example, and not by way of limitation, the PIAS3 protein comprises the amino acid sequence of SEQ ID NO: 26, as set forth below:
MEDGSWCPMKPKKEASEVCPPPGYGLDG-LQYSAVQEGIQPESKKRVEVIDLTIESSSD EEDLPPTKKHCPVTSAAIPALPGSKGALT-SGHQPSSVLRSPAMGTLGSDFLSSLPLHEY PPAFPLG (SEQ ID NO: 26) or an amino acid sequence at least about 95 percent or at least about 98 percent homologous thereto. In certain embodiment, the C-terminus of the PIAS3 protein having the amino acid sequence of SEQ ID NO: 26 can be modified to include poly-arginine. For example, and not by way of limitation, the PIAS3 protein comprises the amino acid sequence of SEQ ID NO: 27, as set forth below:
MEDGSWCPMKPKKEASEVCPPPGYGLDG-LQYSAVQEGIQPESKKRVEVIDLTIESSSD EEDLPPTKKHCPVTSAAIPALPGSKGALT-SGHQPSSVLRSPAMGTLGSDFLSSLPLHEY PPAFPL-GRRRRRRRRRHHHHHH (SEQ ID NO: 27) or an amino acid sequence at least about 95 percent or at least about 98 percent homologous thereto.

In certain embodiments, a PIAS3 protein may be a rat PIAS3 protein having an amino acid sequence as set forth in NCBI/UniProtKB Accession No. NP_113972.2 or an amino acid sequence at least about 95 percent or at least about 98 percent homologous thereto. For example, and not by way of limitation, the rat PIAS3 protein comprises the amino acid sequence of SEQ ID NO: 7, as set forth below:

MAELGELKHMVMSFRVSELQVLLGFAGRNKS-GRKHELLAKALHLLKSSCAP SVQMKIKELYRRRF-PRKTLGPSDLSLLSLPPGTSPVGSPSPLA-SIPPTLLTPGTLLGPKR EVDMHPPLPQPVHPDVTMKPLPFYEVYGELIRPT-TLASTSSQRFEEAHFTFALTPQQL QQILTSREVLP-GAKCDYTIQVQLRFCL-CETSCPQEDYFPPNLFVKVNGKLCPLPGYLPP TKNGAEPKRPSRPINITPLARLSATVPNTIV-VNWSSEFGRNYSLSVYLVRQLTAGTLLQ KLRAK-GIRNPDHSRALIKEKLTADPDSEVATT-SLRVSLMCPLGKMRLTVPCRALTCA HLQSFDAALYLQMNEKKPTWTCPVCDKKAPYESLI-IDGLFMEILNSCSDCDEIQFMED GSWCPMKPKKEAS-EVCPPPGYGLDGLQYSPVQEGNQSENKKRVEVI-DLTIESSSDEE DLPPTKKHCPVTSAAIPALPGSKGALTSGHQPSSVLR-SPAMGTLGSDFLSSLPHEYPP AFPLGADIQGLDLF-SFLQTESQHYSPSVITSLDEQDTLGHFFQFRGTP-PHFLGPLAPTLG SSHRSATPAPAPGRVSSIVAPGSSLREGHGG-PLPSGPSLTGCRSDVISLD (SEQ ID NO: 7) or an amino acid sequence at least about 95 percent or at least about 98 percent homologous thereto.

In non-limiting embodiments, a PIAS3 protein of the present invention can have an amino acid sequence that is a consecutive portion of SEQ ID NO: 7, which is at least 20, or at least 30, or at least 40, or at least 50, or at least 60, or at least 70, or at least 80, or at least 90 or at least 100 or at least 200 amino acids or more in length, or an amino acid sequence at least about 95 percent or at least about 98 percent homologous thereto.

In certain embodiments, a PIAS3 protein of this disclosure can have an amino acid sequence comprising the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27. In certain embodiments, a P1AS3 protein can have an amino acid sequence that is at least about 95 percent homologous to the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27. In certain embodiments, a P1AS3 protein can have an amino acid sequence that is at least about 98 percent homologous to the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27.

In certain embodiments, a nucleic acid encoding a human PIAS3 protein can comprise a nucleic acid sequence as set forth in GenBank Accession No. CR457090.1 or a nucleic acid sequence at least about 95 percent or at least about 98 percent homologous thereto. For example, and not by way of limitation, the nucleic acid comprises the nucleotide sequence of SEQ ID NO: 8, as set forth below:
ATGGCGGAGCTGGGCGAATTAAAGCACATGGTGAT-GAGTTTCCGGGTGTCTGAGC TCCAGGTGCTTCTTGGCTTTGCTGGCCG-GAACAAGAGTGGACGGAAGCACGAGCT CCTGGC-CAAGGCTCTGCACCTCCT-GAAGTCCAGCTGTGCCCCTAGTGTCCAGATG AAGATCAAAGAGCTT-TACCGACGACGCTTTCCCCGGAA-GACCCTGGGGCCCTCTG ATCTCTCCCTTCTCTCTTTGCCCCCTGGCACCTCTC CTGTAGGCTCCCCTGGTCCTC TAGCTCCCAT-TCCCC-CAACGCTGTTGGCCCCTGGCACCCTGCTGGGCCC-CAAGCG TGAGGTGGA-CATGCACCCCCCTCTGCCCCAGCCTGTGCACCCT-GATGTCACCATG AAACCATTGCCCTTCTAT-GAAGTCTATGGGGAGCTCATCCGGCCCACCACCCT TG CATCCACTTCTAGCCAGCGGTTTGAG-GAAGCGCACTTTACCTTTGCCCTCACACCC CAGCAAGTGCAGCAGATTCTTA-CATCCAGAGAGGTTCTGCCAGGAGCCAAATGTG ATTATACCATA-CAGGTGCAGCTAAGGTTCTGTCTCTGTGA-GACCAGCTGCCCCCA GGAAGATTATTTTCCCCC-CAACCTCTTTGTCAAGGTCAATGGGAAACTGTGCC CC CTGCCGGGTTACCTTCCCCCAAC-CAAGAATGGGGCCGAGCCCAAGAGGCCCAGC CGCCCCATCAACAT-CACACCCCTGGCTCGACTCTCAGCCACTGTTCC-CAACACCA TTGTGGTCAATTGGTCATCT-GAGTTCGGACGGAATTACTCCTTGTCTGTGTACCTG GTGAGGCAGTTGACTGCAGGAACCCTTCTA-CAAAAACTCAGAGCAAAGGGTATC CGGAACCCA-GACCACTCGCGGGCACTGATCAAGGAGAAAT-TGACTGCTGACCCT GACAGTGAGGTGGCCACTACAAGTCTCCGGGTGT-CACTCATGTGCCCGCTAGGGA AGATGCGCCTGACTGTCCCTTGTCGTGCCCT-CACCTGCGCCCACCTGCAGAGCTTC GATGCTGCCCTTTATCTACAGATGAAT-GAGAAGAAGCCTACATGGACATGTCCTG TGTGTGACAAGAAGGCTCCCTATGAATCTCTTAT-CATTGATGGTTTATTTATGGAG ATTCT-TAGTTCCTGTTCAGATTGTGATGAGATCCAATT-CATGGAAGATGGATCCTG GTGCCCAATGAAACCCAAGAAGGAGGCATCT-GAGGTTTGCCCCCCGCCAGGGTA TGGGCTG-GATGGCCTCCAGTACAGCCCAGTCCAGGGGG-GAGATCCATCAGAGAA TAAGAAGAAGGTCGAAGTTAT-TGACTTGACAATAGAAAGCTCATCAGATGAGGA GGATCTGCCCCCTACCAAGAAGCACTGTTCTGT-CACCTCAGCTGCCATCCCGGCC CTACCTG-GAAGCAAAGGAGTCCTGACATCTGGCCACCAGC-CATCCTCGGTGCTAA GGAGCCCTGCTATGGGCACGTTGGGTGGGGAT-TTCCTGTCCAGTCTCCCACTACA TGAGTACC-CACCTGCCTTCCCACTGGGAGCCGACATC-CAAGGTTTAGATTTATTTT CATTTCTTCAGACAGAGAGTCAGCAC-TATGGCCCCTCTGTCATCACCTCACTAGAT GAACAGGATGCCCTTGGC-CACTTCTTCCAGTACCGAGGGACCCCTTCT-CACTTTCT GGGCCCACTGGCCCCACGCTGGG-GAGCTCCCACTGCAGCGCCACTCCGGCGCCC CCTCCTGGCCGTGTCAGCAGCAT-TGTGGCCCCTGGGGGGGCCTTGAGGGAGGGGC ATG-GAGGACCCCTGCCCTCAGGTCCCTCTTTGACTGGC TGTCGGTCAGACATCATT TCCCTGGACTGA (SEQ ID NO: 8) or a nucleic acid sequence at least about 95 percent or at least about 98 percent homologous thereto.

In certain embodiments, a nucleic acid encoding a PIAS3 protein may comprise a nucleic acid sequence of SEQ ID NO: 9, as set forth below:
CCCTTCTATGAAGTCTATGGGGAGCTCATCCGGCC-CACCACCCTTGCATCCACTTC TAGCCAGCGGTTT-GAGGAAGCGCACTTTACCTTTGCCCT-CACACCCCAGCAAGTG CAGCAGATTCTTACATCCAGAGAGGTTCTGCCAG-GAGCCAAATGTGATTATACCA TACAGGTGCAGCTAAGGTTCTGTCTCTGTGA-GACCAGCTGCCCCAGGAAGATTA TTTTCCCCC-CAACCTCTTTGTCAAGGTCAATGG-GAAACTGTGCCCCCTGCCGGGTT ACCTTCCCCCAACCAAGAATGGGGCCGAGCC-CAAGAGGCCCAGCCGCCCCATCA ACAT-CACACCCCTGGCTCGACTCTCAGCCACTGTTCC-CAACACCATTGTGGTCAAT TGGTCATCTGAGTTCGGACGGAAT-TACTCCTTGTCTGTGTACCTGGTGAGGCAGTT GACTGCAGGAACCCTTCTA-CAAAAACTCAGAGCAAAGGGTATCCG-GAACCCAGA CCACTCGCGGGCACTGAT-CAAGGAGAAATTGACTGCTGACCCTGACAGTGAG GT G (SEQ ID NO: 9) or a nucleic acid sequence at least about 95 percent or at least about 98 percent homologous thereto.

In certain embodiments, a nucleic acid encoding a PIAS3 protein may comprise a nucleic acid sequence of SEQ ID NO: 10, as set forth below:
TTGCCCTTCTATGAAGTCTATGGGGAGCT-CATCCGGCCCACCACCCTTGCATCCAC TTCTAGCCAGCGGTTTGAGGAAGCGCACTT-TACCTTTGCCCTCACACCCCAGCAA GTGCAGCA-GATTCTTACATCCAGAGAG (SEQ ID NO: 10) or a nucleic acid sequence at least about 95 percent or at least about 98 percent homologous thereto.

In certain embodiments, a nucleic acid encoding a fragment of a human PIAS3 protein that comprises amino acids 400-528 of SEQ ID NO: 1 may comprise the nucleotide sequence of SEQ ID NO: 40, as set forth below:

```
                                        (SEQ ID NO: 40)
ATGGAAGATGGATCCTGGTGCCCAATGAAACCCAAGAAGGAGGCATCTGA

GGTTTGCCCCCCGCCAGGGTATGGGCTGGATGGCCTCCAGTACAGCCCAG

TCCAGGGGGAGATCCATCAGAGAATAAGAAGAAGGTCGAAGTTATTGAC

TTGACAATAGAAAGCTCATCAGATGAGGAGGATCTGCCCCCTACCAAGAA

GCACTGTTCTGTCACCTCAGCTGCCATCCCGGCCCTACCTGGAAGCAAAG

GAGTCCTGACATCTGGCCACCAGCCATCCTCGGTGCTAAGGAGCCCTGCT

ATGGGCACGTTGGGTGGGGATTTCCTGTCCAGTCTCCCACTACATGAGTA

CCCACCTGCCTTCCCACTGGGA
``` or a nucleotide sequence at least about 95 percent or at least about 98 percent homologous thereto.

In certain embodiments, a nucleic acid encoding a fragment of a human PIAS3 protein that comprises amino acids 400-528 of SEQ ID NO: 1 and a poly-arginine cell penetrating peptide may comprise the nucleotide sequence of SEQ ID NO: 41, as set forth below:
ATGGAAGATGGATCCTGGTGCCCAATGAAACC-CAAGAAGGAGGCATCTGAGGTT TGCCCCCCGCCAGGGTATGGGCTG-GATGGCCTCCAGTACAGCCCAGTCCAGGGGG GAGATCCATCAGAGAATAAGAAGAAGGTCGAAGT-TATTGACTTGACAATAGAAA GCTCATCAGATGAG-GAGGATCTGCCCCCTACCAAGAAGCACTGTTCTGT-CACCTC AGCTGCCATCCCGGCCCTACCTG-GAAGCAAAGGAGTCCTGACATCTGGCCACCAG CCATCCTCGGTGCTAAGGAGCCCTGC-TATGGGCACGTTGGGTGGGGATTTCCTGT CCAGTCTCCCACTACATGAGTACC-CACCTGCCTTCCCACTGGGAAGGCGGCGAAG ACGCCGCAGGAGACGGCACCACCATCACCAT-CACTAA (SEQ ID NO: 41) or a nucleotide sequence at least about 95 percent or at least about 98 percent homologous thereto.

In certain embodiments, a nucleic acid encoding a fragment of a mouse PIAS3 protein that comprises amino acids 400-523 of SEQ ID NO: 1 may comprise the nucleotide sequence of SEQ ID NO: 42, as set forth below:
ATGGAAGATGGATCCTGGTGTCCGATGAAACC-CAAGAAGGAGGCATCAGAGGTT TGCCCCCCGCCAGGGTATGGGCTG-GATGGTCTCCAGTACAGCGCAGTCCAGGAGG GAATTCAGCCAGAGAGTAAGAAGAGGGTCGAAGT-CATTGACTTGACCATCGAAA GCTCATCAGATGAG-GAGGATTTGCCCCCCAC-CAAGAAGCACTGCCCTGTCACCTC AGCGGCCATTCCAGCCCTTCCTG-GAAGCAAAGGAGCCCTGACCTCTGGTCACCAG CCATCCTCGGTGCTGCG-GAGCCCTGCAACAATGGGCAGTGACTTCCTGTG CTAGTCTCCCGCTACATGAGTACC-CACCTGCCTTCCCACTGGGGCGACGA (SEQ ID NO: 42) or a nucleotide sequence at least about 95 percent or at least about 98 percent homologous thereto.

In certain embodiments, a nucleic acid encoding a fragment of a mouse PIAS3 protein that comprises amino acids 400-523 of SEQ ID NO: 1 and a poly-arginine cell penetrating peptide may comprise the nucleotide sequence of SEQ ID NO: 43, as set forth below:
ATGGAAGATGGATCCTGGTGTCCGATGAAACC-CAAGAAGGAGGCATCAGAGGTT TGCCCCCCGCCAGGGTATGGGCTG-GATGGTCTCCAGTACAGCGCAGTCCAGGAGG GAATTCAGCCAGAGAGTAAGAAGAGGGTCGAAGT-CATTGACTTGACCATCGAAA GCTCATCAGATGAG-GAGGATTTGCCCCCCAC-CAAGAAGCACTGCCCTGTCACCTC AGCGGCCATTCCAGCCCTTCCTG-GAAGCAAAGGAGCCCTGACCTCTGGTCACCAG CCATCCTCGGTGCTGCG-GAGCCCTGCAACAATGGGCAGTGACTTCCTGTG CTAGTCTCCCGCTACATGAGTACC-CACCTGCCTTCCCACTGGGGCGACGAAGGCG GCGAAGACGGAGGCGGCATCACCATCATCAC-CACTAA (SEQ ID NO: 43) or a nucleotide sequence at least about 95 percent or at least about 98 percent homologous thereto.

In certain embodiments, a nucleic acid for use in the present invention encodes a PIAS3 protein comprising the amino acid sequence of SEQ ID NO: 1 or a fragment thereof. For example, and not by way of limitation, a nucleic acid for use in the present invention can encode a PIAS protein that comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27 or an amino acid sequence that is at least about 95 percent or at least about 98 percent homologous thereto. In certain embodiments, a nucleic acid for use in the present invention can encode a PIAS protein that comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27 or an amino acid sequence that is at least about 95 percent homologous thereto. In certain embodiments, a nucleic acid for use in the present invention can encode a PIAS protein that comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27 or an amino acid sequence that is at least about 98 percent homologous thereto. For example, and not by way of limitation, a nucleic acid for use in the present invention can comprise the nucleotide sequence set forth in SEQ ID NOs: 8-10 and 40-43.

In certain embodiments, the PIAS3 protein or a fragment thereof can be associated with enhanced tumor specific activity of a modified virus as described herein, e.g. an oncolytic vaccinia virus.

SOCS3 (Suppressor of Cytokine Signaling 3; Denoted SOCS3 Herein)

In certain embodiments, the modulator of STAT3 activity can be a SOCS3 protein, or a fragment thereof.

In certain embodiments, a SOCS3 protein can be a human SOCS3 protein having an amino acid sequence as set forth in GenBank Accession No. CAG46495.1 or an amino acid sequence at least about 95 percent or at least about 98 percent homologous thereto. In certain embodiments, a human SOCS3 protein that can comprise an amino acid sequence that has the sequence of SEQ ID NO: 28, set forth below:
MVTHSKFPAAGMSRPLDTSLRLKTFSSKSEYQLVV-NAVRKLQESGFYWSAVTGGEA NLLLSAEPAGTF-LIRDSSDQRHFFTLSVKTQSGTKNL-RIQCEGGSFSLQSDPRSTQPVP RFDCVLKLVHHYMPPPGAPSFPSPPTEPSSEVPEQP-SAQPLPGSPPRRAYYIYSGGEKIP LVLSRPLSSN-VATLQHLCRKTVNGHLDSYEKVTQLPGPIRE-FLDQYDAPL (SEQ ID NO: 28) or an amino acid sequence at least about 95 percent or at least about 98 percent homologous thereto.

In certain embodiments, a nucleic acid encoding a human SOCS3 protein can comprise a nucleic acid sequence as set forth in GenBank Accession No. CR541694.1 or a nucleic acid sequence at least about 95 percent or at least about 98 percent homologous thereto. In certain embodiments, a nucleic acid encoding a human SOCS3 protein comprises the nucleotide sequence of SEQ ID NO: 29, as set forth below:
ATGGTCACCCACAGCAAGTTTCCCGCCGCCGGGAT-GAGCCGCCCCCTGGACACCA GCCTGCGCCTCAA-GACCTTCAGCTC-CAAGAGCGAGTACCAGCTGGTGGTGAACGC AGTGCGCAAGCTGCAGGAGAGCGGCTTCTACTG-GAGCGCAGTGACCGGCGGCGA GGCGAACCTGCTGCTCAGTGCCGAGCCCGCCGGC ACCTTTCTGATCCGCGACAGC TCGGACCAGCGC-CACTTCTTCACGCTCAGCGTCAA-GACCCAGTCTGGGACCAAGA ACCTGCG-CATCCAGTGTGAGGGGGGCAGCTTCTCTCTGCAGA GCGATCCCCGGAG CACGCAGCCCGTGCCCCGCTTCGACTGCGTGCT-CAAGCTGGTGCACCACTACATG CCGCCCCCTG-GAGCCCCCTCCTTCCCCTCGCCACCTACT-GAACCCTCCTCCGAGGT GCCCGAGCAGCCGTCTGCCCAGCCACTCCCTGG-GAGTCCCCCCAGAAGAGCCTAT TACATC-TACTCCGGGGGCGAGAAGATCCCCCTGGTGTT-GAGCCGGCCCCTCTCCT CCAACGTGGCCACTCTTCAGCATCTCTGTCGGAA-GACCGTCAACGGCCACCTGGA CTCCTAT-GAGAAAGTCACCCAGCTGCCGGGGCCCATTCGG-GAGTTCCTGGACCAG TACGATGCCCCGCTT (SEQ ID NO: 29) or a nucleic acid sequence at least about 95 percent or at least about 98 percent homologous thereto.

In certain embodiments, a SOCS3 protein can be a mouse SOCS3 protein that can comprise an amino acid sequence that has the sequence of SEQ ID NO: 30, set forth below:
MVTHSKFPAAGMSRPLDTSLRLKTFSSKSEYQLVV-NAVRKLQESGFYWSAVTGGEA NLLLSAEPAGTF-LIRDSSDQRHFFTLSVKTQSGTKNL-RIQCEGGSFSLQSDPRSTQPVP RFDCVLKLVHHYMPPPGTPSFSLPPTEPSSEVPEQP-PAQALPGSTPKRAYYIYSGGEKI PLVLSRPLSSN-VATLQHLCRKTVNGHLDSYEKVTQLPGPIRE-FLDQYDAPL (SEQ ID NO: 30) or an amino acid sequence at least about 95 percent or at least about 98 percent homologous thereto.

In certain embodiments, a nucleic acid encoding a mouse SOCS3 protein comprises the nucleotide sequence of SEQ ID NO: 31, as set forth below:
ATGGTCACCCACAGCAAGTTTCCCGCCGCCGGGAT-GAGCCGCCCCCTGGACACCA GCCTGCGCCTCAA-GACCTTCAGCTC-CAAAAGCGAGTACCAGCTGGTGGTGAACGC CGTGCGCAAGCTGCAGGAGAGCGGATTCTACTG-GAGCGCCGTGACCGGCGGCGA GGCGAACCTGCTGCTCAGCGCCGAGCCCGCGGGC ACCTTTCTTATCCGCGACAGC TCGGACCAGCGC-CACTTCTTCACGTTGAGCGTCAA-GACCCAGTCGGGGACCAAGA ACCTACG-CATCCAGTGTGAGGGGGGCAGCTTTTCGCTGCAGA GTGACCCCCGAAG CACGCAGCCAGTTCCCCGCTTCGACTGTGTACT-CAAGCTGGTGCACCACTACATG CCGCCTCCAGGGACCCCCTCCTTTTCTTTGCCACC-CACGGAACCCTCGTCCGAAGT TCCGGAGCAGC-CACCTGCCCAGGCACTCCCCGGGAGTACCCC-CAAGAGAGCTTAC TACATCTATTCTGGGGGCGAGAAGAT-TCCGCTGGTACTGAGCCGACCTCTCTCCT CCAACGTGGCCACCCTCCAGCATCTTTGTCGGAA-GACTGTCAACGGCCACCTGGA CTCCTAT-GAGAAAGTGACCCAGCTGCCTGGACCCATTCGG-GAGTTCCTGGATCAG TATGATGCTCCACTTTAA (SEQ ID NO: 31) or a nucleic acid sequence at least about 95 percent or at least about 98 percent homologous thereto.

In non-limiting embodiments, a SOCS3 protein of this disclosure can have an amino acid sequence that can be a consecutive portion of SEQ ID NO: 28 or 30, which is at least 20, or at least 30, or at least 40, or at least 50, or at least 60, or at least 70, or at least 80, or at least 90 or at least 100 and up to 200 amino acids in length, or an amino acid sequence at least about 95 percent or at least about 98 percent homologous thereto. In certain embodiments, a SOCS3 protein can have an amino acid sequence that is at least about 95 percent homologous to the sequence of SEQ ID NO: 28 or 30. In certain embodiments, a SOCS3 protein can have an amino acid sequence that is at least about 98 percent homologous to the sequence of 28 or 30.

In certain embodiments, a nucleic acid for use in this disclosure encodes a SOCS3 protein or a fragment thereof.

For example, and not by way of limitation, a nucleic acid for use in this disclosure can encode a SOCS3 protein that comprises the amino acid sequence of SEQ ID NO: 28 or SEQ ID NO: 30 or an amino acid sequence that is at least about 95 percent or at least about 98 percent homologous thereto. For example, and not by way of limitation, a nucleic acid for use in this disclosure can comprise the nucleotide sequence set forth in SEQ ID NOs: 29 and 31, or a nucleotide sequence at least about 95 percent or at least about 98 percent homologous thereto. In certain embodiments, a nucleic acid for use in this disclosure can comprise the nucleotide sequence set forth in SEQ ID NOs: 29 and 31, or a nucleotide sequence at least about 95 percent homologous thereto. In certain embodiments, a nucleic acid for use in this disclosure can comprise the nucleotide sequence set forth in SEQ ID NOs: 29 and 31, or a nucleotide sequence at least about 98 percent homologous thereto.

TCPTP (T-Cell Protein Tyrosine Phosphatase; Denoted as TCPTP Herein)

In certain embodiments, the modulator of STAT3 activity can be a TCPTP protein.

In certain embodiments, a TCPTP protein can be a human TCPTP isoform 2 protein having an amino acid sequence as set forth in NCBI/UniProtKB Accession No. NP_536347.1 or an amino acid sequence at least about 95 percent or at least about 98 percent homologous thereto. In certain embodiments, a human TCPTP isoform 2 protein can comprise an amino acid sequence that has the sequence of SEQ ID NO: 32, set forth below:
MPTTIEREFEELDTQRRWQPLYLEIRNESHDYPHRVAKFPENRNRNRYRDVSPYDHS RVKLQNAENDYINASLVDIEEAQRSYILTQGPLPNTCCHFWLMVWQQKTKAVVMLN RIVEKESVKCAQYWPTDDQEMLFKETGFSVKLLSEDVKSYYTVH LLQLENINSGETR TISHFHYTTWPDFGVPESPASFLNFLFKVRESGSLNPDHGPAVIHCSAGIGRSGTFSLV DTCLVLMEKGDDINIKQVLLNMRKYRMGLIQTPDQLRFSYMAIIEGAKCIKGDSSIQK RWKELSKEDLSPAFDHSPNKIMTEKYNGNRIGLEEEKLTGDRCTGLSSKMQDTME EN SESALRKRIREDRKATTAQKVQQMKQRLNENERKRKRPRLTDT (SEQ ID NO: 32) or an amino acid sequence at least about 95 percent or at least about 98 percent homologous thereto.

In certain embodiments, a nucleic acid encoding a human TCPTP isoform 2 protein can comprise a nucleic acid sequence as set forth in NCBI/UniProtKB Accession No. NM_080422.2 or a nucleic acid sequence at least about 95 percent or at least about 98 percent homologous thereto. In certain embodiments, a nucleic acid encoding a human TCPTP isoform 2 protein can comprise the nucleotide sequence of SEQ ID NO: 33, as set forth below:
GCTCGGGCGCCGAGTCTGCGCGCTGACGTCCGAC GCTCCAGGTACTTTCCCCACG GCCGACAGGGCTTGGCGTGGGGGCGGGCGCGCGC GCGCGCATGCGCCGC AGCGCCAGCGCTCTCCCCGGATCGTGCGGGGCCTGAGCCTCTCCGCCGGCGCAGG CTCTGCTCGCGCCAGCTCGCTCCCGCAGCCATGCCCACCACCATCGAGCGGGAGT TCGAAGAGTTGGATACTCAGCGTCGCTGGCAGCCGCTGTACTTGGAAATTCGAAA TGAGTCCCATGACTATCCTCATAGAGTGGCCAAGTTTCCAGAAAACAGAAATCGA AACAGATACAGAGATGTAAGCCCATATGATCACAGTCGTGTTAAACTGCAAAAT GCTGAGAATGATTATATTAATGCCAGTTTAGTTGACATAGAAGAGGCACAAAGG AGTTACATCTTAACACAGGGTCCACTTCCTAACATGCTGCCATTTCTGGCTTAT GGTTTGGCAGCAGAAGACCAAAGCAGTTGTCATGCTGAACCGCATTGTGGAGAA AGAATCGGTTAAATGTGCACAGTACTGGCCAACAGATGACCAAGAGATGCTGTTT AAAGAAACAGGATTCAGTGTGAAGCTCTTGTCAGAAGATGTGAAGTCGTATTATA CAGTACATCTACTACAATTAGAAAATATCAATAGTGGTGAAACCAGAACAATATC TCACTTTCATTATACTACCTGGCCAGATTTTGGAGTCCCTGAATCACCAGCTTCAT TTCTCAATTTCTTGTTTAAAGTGAGAGAATCTGGCTCCTTGAACCCTGACCATGGG CCTGCGGTGATCCACTGTAGTGCAGGCATTGGGCGGGCCTCTGGT AGACACTTGTCTTGTTTTGATGGAAAAAGGAGATGATATTAACATAAAACAAGTG TTACTGAACATGAGAAAATACCGAATGGGTCTTATTCAGACCCCAGATCAACTGA GATTCTCATACATGGCTATAATAGAAGGAGCAAAATGTATAAAGGGAGATTCTA GTATACAGAAACGATGGAAAGAACTTTCTAAGGAAGACTTATCTCCTGCCTTTGA TCATTCACCAAACAAAATAATGACTGAAAAATACAATGGGAAC AGAATAGGTCT AGAAGAAGAAAAACTGACAGGTGACCGATGTACAGGACTTTCCTCTAAAATGCA AGATACAATGGAGGAGAACAGTGAGAGTGCTCTACGGAAACGTATTCGAGAGGA CAGAAAGGCCACCACAGCTCAGAAGGTGCAGCAGATGAAACAGAGGCTAAATGA GAATGAACGAAAAAGAAAAAGGCCAAGATTGACAGACACCTAATATTCATGACT TGAGAATATTCTGCAGCTATAAATTTTGAACCATTGATGTGCAAAGCAAGACCTG AAGCCCACTCCGGAAACTAAAGTGAGGCTCGCTAACCCTCTAGATTGCCTCACAG TTGTTTGTTTACAAAGTAAACTTTACATCCAGGGGATGAAGACACCCACCAGCA GAAGACTTTGCAGAACCTTTAATTGGATGTGTTAAGTGTTTTTAATGAGTGTATGA AATGTAGAAAGATGTACAAGAAATAAATTAGGGAGATTACTTTGTATTGTACTG CCATTCCTACTGTATTTTTATACTTTTTGGCAGCATTAAATATTTTTGTTAAATAGT CAAAAAAAAAAAAAAAAA (SEQ ID NO: 33) or a nucleic acid sequence at least about 95 percent or at least about 98 percent homologous thereto.

In certain embodiments, a mouse TCPTP isoform 2 protein can comprise an amino acid sequence that has the sequence of SEQ ID NO: 34, set forth below:
MSATIEREFEELDAQCRWQPLYLEIRNESHDYPHRVAKFPENRNRNRYRDVSPYDHS RVKLQSTENDYINASLVDIEEAQRSYILTQGPLPNTCCHFWLMVWQQKTKAVVMLN RTVEKESVKCAQYWPTDDREMVFKETGFSVKLLSEDVKSYYTVHLLQLENINTGETR TISHFHYTTWPDFGVPESPASFLNFLFKVRESGCLTPDHGPAVIHCSAGIGRSGTFSLV DTCLVLMEKGEDVNVKQLLLNMRKYRMGLIQTPDQLRFSYMAIIEGAKYTKGDSNI QKRWKELSKEDLSPICDHSQNRVMVEKYNGKRIGSEDEKLTGLPSKVQ DTVEESSESI LRKRIREDRKATTAQKVQQMKQRLNETERKRKR-PRLTDT (SEQ ID NO: 34) or an amino acid sequence at least about 95 percent or at least about 98 percent homologous thereto.

In certain embodiments, a nucleic acid encoding a mouse TCPTP isoform 2 protein can comprises the nucleotide sequence of SEQ ID NO: 35, as set forth below:
ATGAGCGCCACTATTGAGCGGGAGTTCGAG-GAACTGGACGCCCAGTGTAGATGG CAGCCCCTT-TATCTTGAGATACGCAACGAAAGTCACGAT-TACCCTCATAGGGTAG CTAAATTCCCTGAGAACAGAAACAGAAACCGC-TACCGCGATGTGTCACCCTACGA TCACTCCAGAGT-GAAACTTCAAAGTACCGAAAATGAT-TATATAAATGCCAGCTTG GTGGACATAGAGGAAGCCCAAAGATCATACATACT-TACTCAAGGGCCTCTCCCAA ACACTTGTTGCCAT-TTCTGGCTCATGGTGTGGCAACAGAAGAC-CAAGGCTGTGGT AATGCTCAATCGGACTGTG-GAAAAAGAGTCAGTAAAGTGTGCTCAATAT-TGGCCA ACTGATGATAGGGAGATGGTCTT-TAAGGAAACAGGTTTCTCCGTTAAGTTGCTCA GTGAGGATGTGAAGTCCTATTACACAGTA-CATCTTCTCCAATTGGAGAACATCAA CACCGGT-GAAACCCGAACAATATCCCACTTTCATTATAC-CACTTGGCCTGACTTC GGTGTTCCTGAAAGCCCCGCTTCTTTTCTCAAT-TTCCTGTTTAAGGTGCGGGAGTC AGGCTGTCT-CACCCCAGATCATGGGCCTGCTGTAATACAT-TGTAGCGCTGGGATC GGGCGATCCGGGACATTCTCTTTGGTA-GACACTTGCCTGGTCCTGATGGAGAAGG GAGAGGACGTAAACGTTAAGCAGTTGCTCCT-GAATATGAGAAAATATCGAATGG GGTTGATTCA-GACTCCCGATCAACTTAGATTCTCTTATATGGC-TATAATCGAGGGC GCAAAATATACCAAGGGGGACTCCAACATT-CAAAAAAGATGGAAGGAGCTCTCT AAGGAA-GATCTGTCTCCAATCTGTGAC-CACAGTCAGAACCGAGTTATGGTAGAGA AATACAACGGTAAAAGAATTGGCTCAGAA-GACGAAACTGACCGGACTCCCCT CCAAAGTGCAA-GATACAGTCGAAGAATCATCCGAGTCAATCTTGAG-GAAAAGAA TCAGGGAAGATCGGAAGGCCACTACAGCC-CAAAAAGTGCAACAAATGAAACAGC GACT-CAACGAAACAGAGCGGAAACGAAAACGGCCAA-GACTGACAGACACCTAA (SEQ ID NO: 35) or a nucleic acid sequence at least about 95 percent or at least about 98 percent homologous thereto.

In certain embodiments, a TCPTP protein of this disclosure can have an amino acid sequence that can be a consecutive portion of SEQ ID NO: 32 or 34, which is at least 20, or at least 30, or at least 40, or at least 50, or at least 60, or at least 70, or at least 80, or at least 90 or at least 100 and up to 200 amino acids in length, or an amino acid sequence at least about 95 percent or at least about 98 percent homologous thereto. In certain embodiments, a TCPTP protein can have an amino acid sequence that is at least about 95 percent homologous to the sequence of SEQ ID NO: 32 or 34. In certain embodiments, a TCPTP protein can have an amino acid sequence that is at least about 98 percent homologous to the sequence of 32 or 34.

In certain embodiments, a nucleic acid for use in the present invention encodes a TCPTP protein. For example, and not by way of limitation, a nucleic acid for use in the present invention can encode a TCPTP protein, i.e., TCPTP isoform 2 protein, that comprises the amino acid sequence of SEQ ID NO: 32 or SEQ ID NO: 34 or an amino acid sequence that is at least about 95 percent or at least about 98 percent homologous thereto. In certain embodiments, a nucleic acid for use in this disclosure can comprise the nucleotide sequence set forth in SEQ ID NOs: 33 and 35, or a nucleotide sequence at least about 95 percent homologous thereto. In certain embodiments, a nucleic acid for use in this disclosure can comprise the nucleotide sequence set forth in SEQ ID NOs: 33 and 35, or a nucleotide sequence at least about 98 percent homologous thereto. For example, and not by way of limitation, a nucleic acid for use in the present invention can comprise the nucleotide sequence set forth in SEQ ID NOs: 33 and 35.

STAT3 Containing Dominant-Negative Mutations

In certain embodiments, the modulator of STAT3 activity can be a STAT3 protein with one or more dominant-negative mutations. In certain embodiments, the dominant-negative mutant STAT3 protein can be a dominant-negative mutant human STAT3 protein.

In certain embodiments, a dominant-negative mutant human STAT3 protein can have a mutation at amino acid 705, e.g., Y705F. For example, and not by way of limitation, a dominant-negative mutant STAT3 protein can comprise an amino acid sequence that has the sequence of SEQ ID NO: 36, set forth below:
MAQWNQLQQLDTRYLEQLHQLYSDSFPMELRQ-FLAPWIESQDWAYAASKESHATL VFHNLLGEIDQQYSRFLQESNVLYQHNLR-RIKQFLQSRYLEKPMEIARIVARCLWEES RLLQTAATAAQQGGQANHPTAAVVTEKQQM-LEQHLQDVRKRVQDLEQKMKVVEN LQDDFDFNYKTLKSQGDMQDLNG-NNQSVTRQKMQQLEQMLTALDQMRRSIVSELA GLL-SAMEYVQKTLTDEELADWKRRQQIACIGGPPNICL-DRLENWITSLAESQLQTRQ QIKKLEELQQKVSYKGDPIVQHRPMLEERIVEL-FRNLMKSAFVVERQPCMPMHPDRP LVIKTGVQFTTKVRLLVKFPELNYQLKIKV-CIDKDSGDVAALRGSRKFNILGTNTKV MNMEESNNGSLSAEFKHLTLREQRCGNGGRANC-DASLIVTEELHLITFETEVYHQGL KIDLETHSLPVV-VISNICQMPNAWASILWYNMLTNNPKNVNFFTKP-PIGTWDQVAEV LSWQFSSTTKRGLSIEQLTTLAEKLLGPGV-NYSGCQITWAKFCKENMAGKGFSFWV WLDNI-IDLVKKYILALWNEGYIMGFISKERERAILSTKPPGT-FLLRFSESSKEGGVTFT WVEKDISGKTQIQSVEPYTKQQLNNMSFAEIIMGY-KIMDATNILVSPLVYLYPDIPKEE AFGKYCRPESQEHPEADPGAAPFLKTK-FICVTPTTCSNTIDLPMSPRTLDSLMQFGNN GEGAEP-SAGGQFESLTFDMELTSECATSPM (SEQ ID NO: 36) or an amino acid sequence at least about 95 percent or at least about 98 percent homologous thereto.

In certain embodiments, SEQ ID NO: 36 can be encoded by the nucleotide sequence of SEQ ID NO: 37, as set forth below:
ATGGCCCAATGGAATCAGCTA-CAGCAGCTTGACACGGTACCTGGAGCAGCTCC ATCAGCTCTACAGTGACAGCTTCCCAATG-GAGCTGCGGCAGTTTCTGGCCCCTTG GATT-GAGAGTCAAGATTGGG-CATATGCGGCCAGCAAAGAATCACATGCCACTTTG GTGTTTCATAATCTCCTGGGAGAGAT-TGACCAGCAGTATAGCCGCTTCCTGCAAG AGTCGAATGTTCTCTATCAGCACAATC-
TACGAAGAATCAAGCAGTTTCTTCAGAG
CAGGTATCTTGAGAAGCCAATGGAGATTGCCCG-
GATTGTGGCCCGGTGCCTGTGG GAAGAAT-
CACGCCTTCTACAGACTGCAGC-
CACTGCGGCCCAGCAAGGGGGCCAG
GCCAACCACCCCACAGCAGCCGTGGTGACG-
GAGAAGCAGCAGATGCTGGAGCAG CACCTTCAG-
GATGTCCGGAAGAGAGTGCAG-
GATCTAGAACAGAAAATGAAAGTG
GTAGAGAATCTCCAGGATGACTTTGATTTCAAC-
TATAAAACCCTCAAGAGTCAAG GAGACATGCAA-
GATCTGAATG-
GAAACAACCAGTCAGTGACCAGGCAGAAGATGC
AGCAGCTGGAACAGATGCTCACTGCGCTGGACCA-
GATGCGGAGAAGCATCGTGA
GTGAGCTGGCGGGGCTTTTGTCAGCGATG-
GAGTACGTGCAGAAAACTCTCACGGA CGAG-
GAGCTGGCTGACTGGAAGAGGCGGCAACAGAT-
TGCCTGCATTGGAGGCCC
GCCCAACATCTGCCTAGATCGGCTAGAAAACTG-
GATAACGTCATTAGCAGAATCT CAACTTCA-
GACCCGTCAACAAATTAAGAAACTGGAG-
GAGTTGCAGCAAAAAGTT
TCCTACAAAGGGGACCCCATTGTA-
CAGCACCGGCCGATGCTGGAGGAGAGAATC GTG-
GAGCTGTTTAGAAACTTAAT-
GAAAAGTGCCTTTGTGGTGGAGCGGCAGCCCT
GCATGCCCATGCATCCTGACCGGCCCCTCGTCAT-
CAAGACCGGCGTCCAGTTCAC
TACTAAAGTCAGGTTGCTGGTCAAATTCCCT-
GAGTTGAATTATCAGCTTAAAATT AAAGTGTGCAT-
TGACAAA-
GACTCTGGGGACGTTGCAGCTCTCAGAGGATCCCG
G AAATTTAACATTCTGGGCACAAACACAAAAGT-
GATGAACATGGAAGAATCCAAC
AACGGCAGCCTCTCTGCAGAATT-
CAAACACTTGACCCTGAGGGAGCAGAGATGT
GGGAATGGGGGCCGAGCCAATTGTGATGCTTCCCT-
GATTGTGACTGAGGAGCTGC ACCTGATCACCTTT-
GAGACCGAGGTGTATCACCAAGGCCTCAAGAT-
TGACCTAGA
GACCCACTCCTTGCCAGTTGTGGTGATCTCCAA-
CATCTGTCAGATGCCAAATGCCT GGGCGTC-
CATCCTGTGGTACAACATGCTGACCAACAATCC-
CAAGAATGTAAACTT
TTTTACCAAGCCCCCAATTGGAACCTGGGAT-
CAAGTGGCCGAGGTCCTGAGCTGG
CAGTTCTCCTCCACCACCAAGCGAGGACTGAG-
CATCGAGCAGCTGACTACACTGG
CAGAGAAACTCTTGGGACCTGGTGTGAATTAT-
TCAGGGTGTCAGATCACATGGGC TAAAT-
TTTGCAAAGAAAA-
CATGGCTGGCAAGGGCTTCTCCTTCTGGGTCTGGC
TG GACAATATCATTGACCTTGTGAAAAAGTA-
CATCCTGGCCCTTTGGAACGAAGGGT ACAT-
CATGGGCTTTATCAGTAAGGAGCGGGAGCGGGC-
CATCTTGAGCACTAAGCC
TCCAGGCACCTTCCTGCTAAGATTCAGT-
GAAAGCAGCAAAGAAGGAGGCGTCAC TTT-
CACTTGGGTGGAGAAGGACATCAGCGGTAA-
GACCCAGATCCAGTCCGTGGA
ACCATACACAAAGCAGCAGCTGAACAACATGTCAT-
TGCTGAAATCATCATGGGC TATAAGATCATG-
GATGCTACCAATATCCTGGTGTCTCCACTGGTC-
TATCTCTATCC
TGACATTCCCAAGGAGGAGGCATTCGGAAAGTAT-
TGTCGGCCAGAGAGCCAGGA GCATCCT-
GAAGCTGACCCAGGCGCTGCCCCATTCCTGAA-
GACCAAGTTTATCTGT
GTGACACCAACGACCTGCAGCAATACCAT-
TGACCTGCCGATGTCCCCCCGCACTT TAGATTCAT-
TGATGCAGTTTGGAAATAATGGTGAAGGTGCT-
GAACCCTCAGCAGG
AGGGCAGTTTGAGTCCCTCACCTTTGACATG-
GAGTTGACCTCGGAGTGCGCTACC TCCCC-
CATGTGA (SEQ ID NO: 37) or a nucleic acid sequence at least about 95 percent or at least about 98 percent homologous thereto.

In certain embodiments, a dominant-negative mutant STAT3 protein can have one or more mutations at amino acids 434 and/or 435, e.g., E434A and E435A. For example, and not by way of limitation, a dominant-negative mutant human STAT3 protein comprises an amino acid sequence that has the sequence of SEQ ID NO: 38, set forth below:
MAQWNQLQQLDTRYLEQLHQLYSDSFPMELRQ-
FLAPWIESQDWAYAASKESHATL
VFHNLLGEIDQQYSRFLQESNVLYQHNLR-
RIKQFLQSRYLEKPMEIARIVARCLWEES
RLLQTAATAAQQGGQANHPTAAVVTEKQQM-
LEQHLQDVRKRVQDLEQKMKVVEN
LQDDFDFNYKTLKSQGDMQDLNG-
NNQSVTRQKMQQLEQMLTALDQMRRSIVSELA GLL-
SAMEYVQKTLTDEELADWKRRQQIACIGGPPNICL-
DRLENWITSLAESQLQTRQ
QIKKLEELQQKVSYKGDPIVQHRPMLEERIVEL-
FRNLMKSAFVVERQPCMPMHPDRP
LVIKTGVQFTTKVRLLVKFPELNYQLKIKV-
CIDKDSGDVAALRGSRKFNILGTNTKV
MNMEESNNGSLSAEFKHLTLREQRCGNGGRANC-
DASLIVTAALHLITFETEVYHQGL KIDLETHSLPVV-
VISNICQMPNAWASILWYNMLTNNPKNVNFFTKP-
PIGTWDQVAEV
LSWQFSSTTKRGLSIEQLTTLAEKLLGPGV-
NYSGCQITWAKFCKENMAGKGFSFWV WLDNI-
IDLVKKYILALWNEGYIMGFISKERERAILSTKPPGT-
FLLRFSESSKEGGVTFT
WVEKDISGKTQIQSVEPYTKQQLNNMSFAEIIMGY-
KIMDATNILVSPLVYLYPDIPKEE
AFGKYCRPESQEHPEADPGAAPYLKTK-
FICVTPTTCSNTIDLPMSPRTLDSLMQFGNN GEGAEP-
SAGGQFESLTFDMELTSECATSPM (SEQ ID NO: 38) or an amino acid sequence at least about 95 percent or at least about 98 percent homologous thereto.

In certain embodiments, SEQ ID NO: 38 can be encoded by the nucleotide sequence of SEQ ID NO: 39, as set forth below:
ATGGCCCAATGGAATCAGCTA-
CAGCAGCTTGACACGGTACCTGGAGCAGCTCC
ATCAGCTCTACAGTGACAGCTTCCCAATG-
GAGCTGCGGCAGTTTCTGGCCCCTTG GATT-
GAGAGTCAAGATTGGG-
CATATGCGGCCAGCAAAGAATCACATGCCACTTTG
GTGTTTCATAATCTCCTGGGAGAGAT-
TGACCAGCAGTATAGCCGCTTCCTGCAAG
AGTCGAATGTTCTCTATCAGCACAATC-
TACGAAGAATCAAGCAGTTTCTTCAGAG
CAGGTATCTTGAGAAGCCAATGGAGATTGCCCG-
GATTGTGGCCCGGTGCCTGTGG GAAGAAT-
CACGCCTTCTACAGACTGCAGC-
CACTGCGGCCCAGCAAGGGGGCCAG
GCCAACCACCCCACAGCAGCCGTGGTGACG-
GAGAAGCAGCAGATGCTGGAGCAG CACCTTCAG-
GATGTCCGGAAGAGAGTGCAG- GATCTAGAACAGAAAATGAAAGTG GTAGAGAATCTCCAGGATGACTTTGATTTCAAC-TATAAAACCCTCAAGAGTCAAG GAGACATGCAA-GATCTGAATG-GAAACAACCAGTCAGTGACCAGGCAGAAGATGC AGCAGCTGGAACAGATGCTCACTGCGCTGGACCA-GATGCGGAGAAGCATCGTGA GTGAGCTGGCGGGGCTTTTGTCAGCGATG-GAGTACGTGCAGAAAACTCTCACGGA CGAG-GAGCTGGCTGACTGGAAGAGGCGGCAACAGAT-TGCCTGCATTGGAGGCCC GCCCAACATCTGCCTAGATCGGCTAGAAAACTG-GATAACGTCATTAGCAGAATCT CAACTTCA-GACCCGTCAACAAATTAAGAAACTGGAG-GAGTTGCAGCAAAAAGTT TCCTACAAAGGGGACCCCATTGTA-CAGCACCGGCCGATGCTGGAGGAGAGAATC GTG-GAGCTGTTTAGAAACTTAAT-GAAAAGTGCCTTTGTGGTGGAGCGGCAGCCCT GCATGCCCATGCATCCTGACCGGCCCCTCGTCAT-CAAGACCGGCGTCCAGTTCAC TACTAAAGTCAGGTTGCTGGTCAAATTCCCT-GAGTTGAATTATCAGCTTAAAATT AAAGTGTGCAT-TGACAAA-GACTCTGGGGACGTTGCAGCTCTCAGAGGATCCCG G AAATTTAACATTCTGGGCACAAACACAAAAGT-GATGAACATGGAAGAATCCAAC AACGGCAGCCTCTCTGCAGAATT-CAAACACTTGACCCTGAGGGAGCAGAGATGT GGGAATGGGGGCCGAGCCAATTGTGATGCTTCCCT-GATTGTGACTGCGGCGCTGC ACCTGATCACCTTT-GAGACCGAGGTGTATCACCAAGGCCTCAAGAT-TGACCTAGA GACCCACTCCTTGCCAGTTGTGGTGATCTCCAA-CATCTGTCAGATGCCAAATGCCT GGGCGTC-CATCCTGTGGTACAACATGCTGACCAACAATCC-CAAGAATGTAAACTT TTTTACCAAGCCCCCAATTGGAACCTGGGAT-CAAGTGGCCGAGGTCCTGAGCTGG CAGTTCTCCTCCACCACCAAGCGAGGACTGAG-CATCGAGCAGCTGACTACACTGG CAGAGAAACTCTTGGGACCTGGTGTGAATTAT-TCAGGGTGTCAGATCACATGGGC TAAAT-TTTGCAAAGAAAA-CATGGCTGGCAAGGGCTTCTCCTTCTGGGTCTGGC TG GACAATATCATTGACCTTGTGAAAAAGTA-CATCCTGGCCCTTTGGAACGAAGGGT ACAT-CATGGGCTTTATCAGTAAGGAGCGGGAGCGGGC-CATCTTGAGCACTAAGCC TCCAGGCACCTTCCTGCTAAGATTCAGT-GAAAGCAGCAAAGAAGGAGGCGTCAC TTT-CACTTGGGTGGAGAAGGACATCAGCGGTAA-GACCCAGATCCAGTCCGTGGA ACCATACACAAAGCAGCAGCTGAACAACATGTCAT-TTGCTGAAATCATCATGGGC TATAAGATCATG-GATGCTACCAATATCCTGGTGTCTCCACTGGTC-TATCTCTATCC TGACATTCCCAAGGAGGAGGCATTCGGAAAGTAT-TGTCGGCCAGAGAGCCAGGA GCATCCT-GAAGCTGACCCAGGCGCTGCCCCATACCTGAA-GACCAAGTTTATCTGT GTGACACCAACGACCTGCAGCAATACCAT-TGACCTGCCGATGTCCCCCCGCACTT TAGATTCAT-TGATGCAGTTTGGAAATAATGGTGAAGGTGCT-GAACCCTCAGCAGG AGGGCAGTTTGAGTCCCTCACCTTTGACATG-GAGTTGACCTCGGAGTGCGCTACC TCCCC-CATGTGA (SEQ ID NO: 39) or a nucleotide sequence at least about 95 percent or at least about 98 percent homologous thereto.

In certain embodiments, a nucleic acid for use in this disclosure can encode a dominant-negative mutant STAT3 protein. For example, and not by way of limitation, a nucleic acid for use in this disclosure can encode a dominant-negative mutant STAT3 protein that comprises the amino acid sequence of SEQ ID NO: 36 or SEQ ID NO: 38 or an amino acid sequence that is at least about 95 percent or at least about 98 percent homologous thereto. In certain embodiments, a dominant-negative mutant STAT3 protein can have an amino acid sequence that is at least about 95 percent homologous to the sequence of SEQ ID NO: 36 or 38. In certain embodiments, a dominant-negative mutant STAT3 protein can have an amino acid sequence that is at least about 98 percent homologous to the sequence of 36 or 38. In certain embodiments, a nucleic acid for use in this disclosure can comprise the nucleotide sequence set forth in SEQ ID NOs: 37 and 39, or a nucleotide sequence at least about 95 percent homologous thereto. In certain embodiments, a nucleic acid for use in this disclosure can comprise the nucleotide sequence set forth in SEQ ID NOs: 37 and 39, or a nucleotide sequence at least about 98 percent homologous thereto.

In certain embodiments, an oncolytic virus can comprise an amino acid sequence that is 95% homologous to the amino acid sequence of any one of SEQ ID NOs: 1-7, 11, 14, 16, 18, 20, 22, 24-28, 30, 32, 34, 36 and 38. In certain embodiments, an oncolytic virus can comprise an amino acid sequence that is 98% homologous to the amino acid sequence of any one of SEQ ID NOs: 1-7, 11, 14, 16, 18, 20, 22, 24-28, 30, 32, 34, 36 and 38.

In certain embodiments, an oncolytic virus can comprise a nucleotide sequence that is 95% homologous to the nucleotide sequence of any one of SEQ ID NOs: 8-10, 12-13, 15, 17, 19, 21, 23, 29, 31, 33, 35, 37 and 39-43. In certain embodiments, an oncolytic virus can comprise a nucleotide sequence that is 98% homologous to the nucleotide sequence of any one of SEQ ID NOs: 8-10, 12-13, 15, 17, 19, 21, 23, 29, 31, 33, 35, 37 and 39-43.

In certain embodiments, changes to the amino acid sequence of the PIAS3, SOCS3, or TCPTP proteins set forth above can be made where the resulting protein maintains the ability to function as modulator of STAT3. In certain embodiments, such changes are referred to as conservative substitutions. As used herein, the terms "conservative substitutions" and "conservative modifications" refer to amino acid modifications that do not significantly affect or alter the binding characteristics of the presently disclosed STAT3 modulator proteins comprising the amino acid sequence. Such conservative modifications include amino acid substitutions, additions and deletions. Modifications can be introduced into the STAT3 modulator proteins of this disclosure by standard techniques known in the art, such as site-directed mutagenesis and PCR-mediated mutagenesis. Amino acids can be classified into groups according to their physicochemical properties such as charge and polarity.

Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within the disclosed STAT3 modulators can be replaced with other amino acid residues from the same group and the altered STAT3 modulator protein can be tested for retained function using the functional assays described herein. In certain embodiments, no more than one, no more than two, no more than three, no more than four, no more than five residues within a specified sequence are altered. Exemplary conservative amino acid substitutions are shown in Table 1.

TABLE 1

| Original Residue | Exemplary Conservative Amino Acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Cancer Targets

In certain embodiments of this disclosure, a method of treatment for a hyperproliferative disease, such as a cancer or a tumor, by the delivery of a modified virus, such as an oncolytic vaccinia virus as described herein, is contemplated. Cancers that can be treated by a modified virus, e.g., a modified vaccinia virus that can comprise an exogenous nucleic acid coding for a modulator of STAT3-mediated gene-activation of this disclosure can include, but are not limited to, melanoma, hepatocellular carcinoma, breast cancer, lung cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiforme, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, and sarcoma.

Cancer cells that can be treated by the methods of this disclosure include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In various examples, the modulator of STAT3-mediated gene-activation of, for use in a modified virus of this disclosure, such as an oncolytic vaccinia virus, that can be used to treat cancer targets disclosed herein, can be a PIAS3 protein or a fragment thereof, a SOCS3 protein or a fragment thereof, a TCPTP protein or a fragment thereof, a STAT3 protein or a fragment thereof, e.g., a STAT3 protein that can comprise a dominant-negative mutation.

This disclosure also contemplates methods for inhibiting or preventing local invasiveness or metastasis, or both, of any type of primary cancer. For example, the primary cancer can be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments, the primary cancer can be lung cancer. For example, and not by way of limitation, the lung cancer can be non-small cell lung carcinoma. Moreover, this disclosure can be used to prevent cancer or to treat pre-cancers or premalignant cells, including metaplasias, dysplasias, and hyperplasias. It can also be used to inhibit undesirable but benign cells, such as squamous metaplasia, dysplasia, benign prostate hyperplasia cells, hyperplastic lesions, and the like. In certain embodiments, the progression to cancer or to a more severe form of cancer can be halted, disrupted, or delayed by methods of this disclosure involving STAT3 modulating agents that can be encoded by a modified virus, such as an oncolytic vaccinia virus, as discussed herein. In various examples, the modulator of STAT3-mediated gene-activation of, for use in a modified virus of this disclosure, such as an oncolytic vaccinia virus, that can be used for inhibiting or preventing local invasiveness or metastasis, or both, of any type of primary cancer, can be a PIAS3 protein or a fragment thereof, a SOCS3 protein or a fragment thereof, a TCPTP protein or a fragment thereof, a STAT3 protein or a fragment thereof, e.g., a STAT3 protein that can comprise a dominant-negative mutation.

Methods of Treatment and Assaying the Efficacy and Pharmacokinetics

The present disclosure provides methods for treating a subject by administration of one or more modified viruses, as disclosed herein. An "individual" or "subject," as used interchangeably herein, refers to a human or a non-human subject. Non-limiting examples of non-human subjects include non-human primates, dogs, cats, mice, rats, guinea pigs, rabbits, pigs, fowl, horses, cows, goats, sheep, cetaceans, etc. In certain embodiments, the subject is human.

The present disclosure provides methods of producing a toxic effect in a cancer cell comprising administering, to the cancer cell, a therapeutically effective amount of a modified virus, such as an oncolytic vaccinia virus, as described above, or a pharmaceutical composition containing the same. This disclosure further provides a method of inhibiting at inhibiting the growth and/or proliferation of a second cancer cell comprising administering, to a first cancer cell, a modified virus as described above such that the first cancer cell is infected with said virus. Thus, in certain embodiments of the methods disclosed here, it is contemplated that not every cancer or tumor cell is infected upon administering a therapeutically effective amount of an oncolytic vaccinia virus, as described herein, or a pharmaceutical composition containing the same, and growth of non-infected cells can be inhibited without direct infection.

In certain embodiments, to induce oncolysis, kill cells, inhibit growth, inhibit metastases, decrease tumor size and otherwise reverse or reduce the malignant phenotype of tumor cells, using the methods and compositions of the present disclosure, a cancer cell or a tumor can be contacted with a therapeutically effective dose of an exemplary oncolytic vaccinia virus as described herein or a pharmaceutical composition containing the same. In certain embodiments, an effective amount of a modified virus of the present disclosure, such as an oncolytic vaccinia virus as described herein or a pharmaceutical composition thereof, can include an amount sufficient to induce oncolysis, the disruption or lysis of a cancer cell or the inhibition or reduction in the growth or size of a cancer cell. Reducing the growth of a cancer cell may be manifested, for example, by cell death or a slower replication rate or reduced growth rate of a tumor comprising the cell or a prolonged survival of a subject containing the cancer cell.

The present disclosure further provides a method of at least partially re-sensitizing a cancer patient to a cancer therapy, comprising administering to a subject in need thereof a therapeutically effective amount of an oncolytic vaccinia virus disclosed herein or a pharmaceutical composition disclosed herein, in combination with a drug that enhances the replication of the vaccinia virus within tumor cells.

Provided, in certain embodiments, is a method of treating a subject having a cancer or a tumor, comprising administering, to the subject, an effective amount of a modified virus, as described above. An effective amount in such method can include an amount that reduces growth rate or spread of the cancer or that prolongs survival in the subject. This disclosure provides a method of reducing the growth of a tumor, which method can comprise administering, to the tumor, an effective amount of a modified virus as described above. In certain embodiments, an effective amount of a modified virus, or a pharmaceutical composition thereof, can include an amount sufficient to induce the slowing, inhibition or reduction in the growth or size of a tumor and can include the eradication of the tumor. Reducing the growth of a tumor may be manifested, for example, by reduced growth rate or a prolonged survival of a subject containing the tumor.

This disclosure also provides a method of determining the infectivity or anti-tumor activity of an oncolytic vaccinia virus as described herein, which method can comprise (i) collecting a first biological sample from a subject and determining the level of STAT3 in the first biological sample; (ii) administering to the subject a therapeutically effective amount of an oncolytic vaccinia virus or a pharmaceutical composition according to the present disclosure, alone or in combination with a further therapy; (iii) collecting a second biological sample from the subject after about 15 mins to about 72 hours following the administration in step (ii) and (iii) detecting the level of a STAT3 protein in the second biological sample, wherein the oncolytic vaccinia virus is determined to be infective or demonstrate anti-tumor activity if the level of STAT3 is lower in step (iii) than in step (i). In certain embodiments, the method disclosed above can further comprise, detecting in steps (i) and (iii), the level of one or more proteins regulated by STAT3, such Asp53 (Uniprot Accession No. P04637-1), Fas (Uniprot Accession No. P25445), Hsp70 (Uniprot Accession No. P0DMV8), Cyclin-D1 (Uniprot Accession No. P24385), IL-10 (Uniprot Accession No. P22301.1), etc. See, e.g., Carpenter and Lo, Cancers 2014, 6, 897-925.

In certain embodiments, anti-tumor efficacy is determined by assaying cytokine levels, e.g., IL-2, IL-7, IL-8, IL-10, IFN-γ, GM-CSF, TNF-α, IL-6, IL-4, IL-5, and IL-13, in plasma samples collected from a subject after administering to said subject a therapeutically effective amount of a modified virus of the present disclosure, such as an oncolytic vaccinia virus as described herein or a pharmaceutical composition comprising the same.

Further provided herein is a method of monitoring the pharmacokinetics following administration of a therapeutically effective amount of modified viruses according to the present disclosure, such as oncolytic vaccinia virus or a pharmaceutical composition containing the vaccinia virus, as described herein. An exemplary method for monitoring the pharmacokinetics can comprise the following steps: (i) administering to the subject a therapeutically effective amount of an oncolytic vaccinia virus or a pharmaceutical composition comprising the same, alone or in combination with a further therapy; (ii) collecting biological samples from the subject at one or more time points selected from about 15 minutes, about 30 minutes, about 45 mins, about 60 mins, about 75 mins, about 90 mins, about 120 mins, about 180 mins, and about 240 mins following the administration in step (ii) and (iii) detecting the quantity of the viral genome in the biological samples collected at the above mentioned time points. In certain embodiments, viral genome copies/mL can be highest in the sample collected at the 15 mins time point and further the sample collected at the 240 mins time point may not contain a detectable quantity of the viral genome. Therefore, in certain embodiments, a viral peak can be observed at about 15 mins following administration and majority of the viruses can be cleared from the subject's system after about 240 mins (or 4 hours). In certain embodiments, a first viral peak can be observed after about 15 mins following administration and a second viral peak can be observed in the biological samples collected in the subsequent time points, e.g., at about 30 mins, about 45 mins, about 60 mins, or about 90 mins. The biological sample can be, in certain embodiments, blood, and the quantity of viral genome/mL can be determined by quantitative PCR or other appropriate techniques. In certain embodiments, a first viral peak can be observed after about 15 mins following administration and a second viral peak can be observed after about 3 hours to about 72 hours following administration of a modified virus of the present disclosure, such as an oncolytic vaccinia virus as described herein.

Delivery of Modified Viruses

In certain embodiments, amount of a modified virus of this disclosure, such as an oncolytic vaccinia virus, administered to a subject can be between about $10^3$ and $10^{12}$ infectious viral particles or plaque forming units (PFU), or between about $10^5$ and $10^{10}$ PFU, or between about $10^5$ and $10^8$ PFU, or between about $10^8$ and $10^{10}$ PFU. See also Thorne and Kim, 2009, Nat Rev Cancer 9: 64-71. In certain embodiments, the amount of a modified virus of this disclosure, such as an oncolytic vaccinia virus administered to a subject can be between about $10^3$ and $10^{12}$ viral particles or PFU, or between about $10^5$ and $10^{10}$ PFU, or between about $10^5$ and $10^8$ PFU, or between about $10^8$ and $10^{10}$ PFU. In certain embodiments, a modified virus of this disclosure, such as an oncolytic vaccinia virus, can be administered at a dose that can comprise about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In certain embodiments, a modified virus of this disclosure, such as an oncolytic vaccinia virus, can be administered at a dose that can comprise about $10^3$ viral particles/dose to about $10^4$ viral particles/dose, about $10^4$ viral particles/dose to about $10^5$ viral particles/dose, about $10^5$ viral particles/dose to about $10^6$ viral particles/dose, about $10^7$ viral particles/dose to about $10^8$ viral particles/dose, about $10^9$ viral particles/dose to about $10^{10}$ viral particles/dose, about $10^{10}$ viral particles/dose to about $10^{11}$ viral particles/dose, about $10^{11}$ viral particles/dose to about $10^{12}$ viral particles/dose, about $10^{12}$ viral particles/dose to about $10^{13}$ viral particles/dose, about $10^{13}$ viral particles/dose to about $10^{14}$ viral particles/dose, or about $10^{14}$ viral particles/dose to about $10^{15}$ viral particles/dose.

In certain embodiments, a modified virus of this disclosure can be administered at a dose that can comprise about $10^3$ PFU/kg to about $10^4$ PFU/kg, about $10^4$ PFU/kg to about $10^5$ PFU/kg, about $10^5$ PFU/kg to about $10^6$ PFU/kg, about $10^7$ PFU/kg to about $10^8$ PFU/kg, about $10^9$ PFU/kg to about $10^{10}$ PFU/kg, about $10^{10}$ PFU/kg to about $10^{11}$ PFU/kg, about $10^{11}$ PFU/kg to about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In certain embodiments, a modified virus of this disclosure can be administered at a dose that can comprise about $10^3$ viral particles/kg to about $10^4$ viral particles/kg, about $10^4$ viral particles/kg to about $10^5$ viral particles/kg, about $10^5$ viral particles/kg to about $10^6$ viral particles/kg, about $10^7$ viral particles/kg to about $10^8$ viral particles/kg, about $10^9$ viral particles/kg to about $10^{10}$ viral particles/kg, about $10^{10}$ viral particles/kg to about $10^{11}$ viral particles/kg, about $10^{11}$ viral particles/kg to about $10^{12}$ viral particles/kg, about $10^{12}$ viral particles/kg to about $10^{13}$ viral particles/kg, about $10^{13}$ viral particles/kg to about $10^{14}$ viral particles/kg, or about $10^{14}$ viral particles/kg to about $10^{15}$ viral particles/kg.

A liquid dosage form of an oncolytic vaccinia virus as described herein can comprise, in certain embodiments, a viral dose of about $10^3$ PFU/mL to about $10^4$ PFU/mL, about $10^4$ PFU/mL to about $10^5$ PFU/mL, about $10^5$ PFU/mL to about $10^6$ PFU/mL, about $10^7$ PFU/mL to about $10^8$ PFU/mL, about $10^9$ PFU/mL to about $10^{10}$ PFU/mL, about $10^{10}$ PFU/mL to about $10^{11}$ PFU/mL, about $10^{11}$ PFU/mL to about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In certain embodiments, where the modified virus is administered by an injection, the dosage can comprise about $10^3$ viral particles per injection, $10^4$ viral particles per injection, $10^5$ viral particles per injection, $10^6$ viral particles per injection, $10^7$ viral particles per injection, $10^8$ viral particles per injection, $10^9$ viral particles per injection, $10^{10}$ viral particles per injection, $10^{11}$ viral particles per injection, $10^{12}$ viral particles per injection, $2\times10^{12}$ viral particles per injection, $10^{13}$ viral particles per injection, $10^{14}$ viral particles per injection, or $10^{15}$ viral particles per injection. In further instances, where the modified virus is administered by an injection, the dosage can comprise about $10^3$ infectious viral particles per injection, $10^4$ infectious viral particles per injection, $10^5$ infectious viral particles per injection, $10^6$ infectious viral particles per injection, $10^7$ infectious viral particles per injection, $10^8$ infectious viral particles per injection, $10^9$ infectious viral particles per injection, $10^{10}$ infectious viral particles per injection, $10^{11}$ infectious viral particles per injection, $10^{12}$ infectious viral particles per injection, $2 \times 10^{12}$ infectious viral particles per injection, $10^{13}$ infectious viral particles per injection, $10^{14}$ infectious viral particles per injection, or $10^{15}$ infectious viral particles per injection. In additional embodiments, a modified virus of this disclosure can be administered at a dose that can be about $10^3$ Tissue Culture Inhibitor Dose 50% ($TCID_{50}$)/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $3 \times 10^8$ $TCID_{50}$/kg, $4 \times 10^8$ $TCID_{50}$/kg, $5 \times 10^8$ $TCID_{50}$/kg, $3 \times 10^9$ $TCID_{50}$/kg, $4 \times 10^9$ $TCID_{50}$/kg, $5 \times 10^9$ $TCID_{50}$/kg, $3 \times 10^{10}$ $TCID_{50}$/kg, $4 \times 10^{10}$ $TCID_{50}$/kg, or $4 \times 10^{10}$ $TCID_{50}$/kg. Note that herein $10^x$ is alternatively expressed as 1 eX. In certain embodiments, the modified virus can be administered in one or more doses. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor. In certain embodiments, a single dose of virus can refer to the amount administered to a subject or a tumor over a 1, 2, 5, 10, 15, 20 or 24 hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified virus can be administered to the subject over a period of 1, 2, 3, 4, 5, 6, 7 or more days or weeks. In certain embodiments, the oncolytic vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the oncolytic vaccinia virus or the pharmaceutical composition as described herein can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain embodiments of the methods disclosed herein, the oncolytic vaccinia virus or the pharmaceutical composition can be administered, independently, in an initial dose for a first period of time, an intermediate dose for a second period of time, and a high dose for a third period of time. In certain embodiments, the initial dose is lower than the intermediate dose and the intermediate dose is lower than the high dose. In certain embodiments, the first, second, and third periods of time are, independently, about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer.

In certain embodiments, the subject can be put on a reduced carbohydrate diet, e.g., a ketogenic diet prior to, concurrent with, and following administration of the modified viruses, such as the oncolytic vaccinia viruses or the pharmaceutical composition comprising the same, as described herein, according to any of the methods of treatment described herein. In certain embodiments, the subject is put on a diet that can comprise consuming less than 500 grams of carbohydrates per day, less than 450 grams of carbohydrates per day, less than 450 grams of carbohydrates per day, less than 400 grams of carbohydrates per day, less than 350 grams of carbohydrates per day, less than 300 grams of carbohydrates per day, less than 250 grams of carbohydrates per day, less than 200 grams of carbohydrates per day, less than 150 grams of carbohydrates per day, less than 100 grams of carbohydrates per day, less than 90 grams of carbohydrates per day, less than 80 grams of carbohydrates per day, less than 70 grams of carbohydrates per day, less than 60 grams of carbohydrates per day, less than 50 grams of carbohydrates per day, less than 40 grams of carbohydrates per day, less than 30 grams of carbohydrates per day, less than 20 grams of carbohydrates per day, less or than 10 grams of carbohydrates per day.

An exemplary method for the delivery of a modified virus of the present disclosure, such as an oncolytic vaccinia virus as described herein or a pharmaceutical composition comprising the same, to cancer or tumor cells can be via intratumoral injection. However, alternate methods of administration can also be used, e.g., intravenous, via infusion, parenteral, intravenous, intradermal, intramuscular, transdermal, rectal, intraurethral, intravaginal, intranasal, intrathecal, or intraperitoneal. The routes of administration can vary with the location and nature of the tumor. In certain embodiments, the route of administration can be intradental, transdermal, parenteral, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. In certain embodiments, the modified virus can be administered to the patient from a source implanted in the patient. In certain embodiments, administration of the modified virus can occur by continuous infusion over a selected period of time. In certain embodiments, an oncolytic vaccinia virus as described herein, or a pharmaceutical composition containing the same can be administered at a therapeutically effective dose by infusion over a period of about 15 mins, about 30 mins, about 45 mins, about 50 mins, about 55 mins, about 60 minutes, about 75 mins, about 90 mins, about 100 mins, or about 120 mins or longer. The oncolytic vaccinia virus or the pharmaceutical composition of the present disclosure can be administered as a liquid dosage, wherein the total volume of administration is about 1 ml to about 5 ml, about 5 ml to 10 ml, about 15 ml to about 20 ml, about 25 ml to about 30 ml, about 30 ml to about 50 ml, about 50 ml to about 100 ml, about 100 ml to 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to 500 ml, about 500 ml to 750 ml or about 750 ml to 1000 ml.

Pharmaceutical Compositions

The present disclosure further provides pharmaceutical compositions comprising the modified viruses disclosed herein. In certain embodiments, the pharmaceutical compositions containing a modified virus, such as an oncolytic vaccinia virus, as described herein, can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof. Pharmaceutical compositions are formulated relative to the particular administration route. For example, and not by way of limitation, pharmaceutical compositions that can be administered parenterally, intravenously, intradermally, intramuscularly, transdermally or intraperitoneally are described in U.S. Pat. Nos. 5,543,158, 5,641,515 and 5,399,363, the contents of which are incorporated by reference herein in their entireties.

In certain embodiments, a pharmaceutical composition as described herein can comprise an excipient. An excipient can be an excipient described in the Handbook of Pharmaceutical Excipients, American Pharmaceutical Association (1986). Non-limiting examples of suitable excipients can include a buffering agent, a preservative, a stabilizer, a binder, a compaction agent, a lubricant, a chelator, a dispersion enhancer, a disintegration agent, a flavoring agent, a sweetener, a coloring agent.

In certain embodiments, an excipient can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof can be used in a pharmaceutical formulation.

In certain embodiments, an excipient can comprise a preservative. Non-limiting examples of suitable preservatives can include antioxidants, such as alpha-tocopherol and ascorbate, and antimicrobials, such as parabens, chlorobutanol, and phenol. Antioxidants can further include but not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In certain embodiments a preservatives can include validamycin A, TL-3, sodium ortho vanadate, sodium fluoride, N-a-tosyl-Phe-chloromethylketone, N-a-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In certain embodiments, a pharmaceutical composition as described herein can comprise a binder as an excipient. Non-limiting examples of suitable binders can include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof. The binders that can be used in a pharmaceutical formulation can be selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or a combination thereof.

In certain embodiments, a pharmaceutical composition as described herein can comprise a lubricant as an excipient. Non-limiting examples of suitable lubricants can include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that can be used in a pharmaceutical formulation can be selected from metallic stearates (such as magnesium stearate, calcium stearate, aluminium stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In certain embodiments, a pharmaceutical formulation can comprise a dispersion enhancer as an excipient. Non-limiting examples of suitable dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In certain embodiments, a pharmaceutical composition as described herein can comprise a disintegrant as an excipient. In certain embodiments a disintegrant can be a non-effervescent disintegrant. Non-limiting examples of suitable non-effervescent disintegrants can include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In certain embodiments a disintegrant can be an effervescent disintegrant. Non-limiting examples of suitable effervescent disintegrants can include sodium bicarbonate in combination with citric acid, and sodium bicarbonate in combination with tartaric acid.

In certain embodiments an excipient can comprise a flavoring agent. Flavoring agents incorporated into an outer layer can be chosen from synthetic flavor oils and flavoring aromatics; natural oils; extracts from plants, leaves, flowers, and fruits; and combinations thereof. In certain embodiments a flavoring agent can be selected from the group consisting of cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In certain embodiments, an excipient can comprise a sweetener. Non-limiting examples of suitable sweeteners can include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like.

In certain embodiments, a pharmaceutical composition as described herein can comprise a coloring agent. Non-limiting examples of suitable color agents can include food, drug and cosmetic colors (FD&C), drug and cosmetic colors (D&C), and external drug and cosmetic colors (Ext. D&C). A coloring agents can be used as dyes or their corresponding lakes.

In certain embodiments, a pharmaceutical composition as described herein can comprise a chelator. In some cases, a chelator can be a fungicidal chelator. Examples can include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraacetic acid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11] pentatriacontane hexahydrobromide; or triethylenetetramine-N,N,N',N'',N''',N'''-hexaacetic acid.

Also contemplated are combination products that include one or more modified viruses disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nysatin, amorolfine, butenafine, naftifine, terbinafine, and other topical agents. In certain embodiments, a pharmaceutical composition can comprise an additional agent. In some cases, an additional agent can be present in a therapeutically effective amount in a pharmaceutical composition.

Under ordinary conditions of storage and use, the pharmaceutical compositions as described herein can comprise a preservative to prevent the growth of microorganisms. In certain examples, the pharmaceutical compositions as described herein may not comprise a preservative. The pharmaceutical forms suitable for injectable use can include sterile aqueous solutions or dispersions and sterile powders for the extemporaneous preparation of sterile injectable solutions or dispersions. The pharmaceutical compositions can comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the liquid dosage form can be suitably buffered if necessary and the liquid diluent rendered isotonic with sufficient saline or glucose. The liquid dosage forms are especially suitable for intravenous, intramuscular, subcutaneous, intratumoral, and intraperitoneal administration. In this connection, sterile aqueous media that can be employed will be known to those of skill in the art in light of the present disclosure. For example, one dosage may be dissolved in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions can be prepared by incorporating a modified virus according to the present disclosure, such as oncolytic vaccinia viruses as described herein or a pharmaceutical composition containing the same, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions can be administered in a manner compatible with the dosage formulation and in such amount as is therapeutically effective.

In certain embodiments, a pharmaceutical composition of this disclosure can comprise an effective amount of a modified virus, disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the modified virus or any other suitable vehicle, delivery or dispensing means or material. Such carriers can be formulated by conventional methods and can be administered to the subject at an effective amount.

Methods of Production

The modified viruses of this disclosure can be produced by methods known to one of skill in the art. In certain embodiments, the modified virus can be propagated in suitable host cells, isolated from host cells and stored in conditions that promote stability and integrity of the virus, such that loss of infectivity over time is minimized. Non-limiting examples of host cells include HeLa cells, HEK293 cells and Vero cells. In certain exemplary methods, the modified viruses are propagated in host cells using cell stacks, roller bottles, or perfusion bioreactors. In certain embodiments, downstream methods for purification of the modified viruses can comprise filtration (e.g., depth filtration, tangential flow filtration, or a combination thereof), ultracentrifugation, or chromatographic capture. The modified virus can be stored, e.g., by freezing or drying, such as by lyophilization. In certain embodiments, prior to administration, the stored modified virus can be reconstituted (if dried for storage) and diluted in a pharmaceutically acceptable carrier for administration.

Combination Therapies

In certain embodiments, the methods of this disclosure comprise administering a modified virus as disclosed herein or a pharmaceutical composition containing the same, followed by, and preceded by or in combination with one or more further therapy. Examples of the further therapy can include, but are not limited to, chemotherapy, radiation, oncolytic viral therapy with an additional virus, treatment with immunomodulatory proteins, a STAT3 inhibitor, an anti-cancer agent, or any combinations thereof. The further therapy can be administered concurrently or sequentially with respect to administration of the modified virus, such as oncolytic vaccinia virus. In certain embodiments, the methods of this disclosure can comprise administering a modified virus as disclosed herein, followed by, preceded by, or in combination with one or more anti-cancer agents or cancer therapies. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof. In certain embodiments, the methods of this disclosure can include administering a modified virus, disclosed herein, followed by, preceded by or in combination with one or more STAT3 inhibitors. Non-limiting examples of STAT3 inhibitors include compounds, molecules, chemicals, polypeptides and proteins that inhibit and/or reduce the expression and/or activity of STAT3. In certain embodiments, the STAT3 inhibitor can include peptide aptamers designed to block STAT3 dimerization or DNA binding; the mammalian proteins SOCS3 and GRIM-19; small molecules such as, but not limited to, S3I-201, S31-2001, STA-21, 1S3-295, witha-cnistin, galiellalactone, niclosamide, stattic and cucurbitacins (e.g., cucurbitacin I); or combinations thereof. Additional non-limiting examples of STAT3 inhibitors are disclosed in Yue et al., Expert Opin. Investig. Drugs 18(1): 45-56 (2009), Siveen et al., Biochimica et Biophysica Acta 1845:136-154 (2014), Bu et al., Gene 512(2):198-205 (2013) and Furtek et al. ACS Chem. Biol. 11(2):308-318 (2016), the contents of which are incorporated by reference herein in their entireties. In certain embodiments, the STAT3 inhibitor can be an antibody or antibody fragment that can partially or completely block STAT3 signaling and/or activity. Further non-limiting examples of STAT3 inhibitors can include ribozyines, antisense oligonucleotides, decoy oligonucleotides blocking the STAT3 DNA-binding site by mimicking STAT3 response elements, shRNA molecules and siRNA molecules that specifically inhibit and/or reduce the expression or activity of STAT3. One non-limiting example of a STAT3 inhibitor can comprise an antisense, shRNA or siRNA nucleic acid sequence homologous to at least a portion of a STAT3 nucleic acid sequence, wherein the homology of the portion relative to the STAT3 sequence can at least be about 75 or at least be about 80 or at least be about 85 or at least be about 90 or at least be about 95 or at least be about 98 percent, where percent homology can be determined by, for example, BLAST or FASTA software. In certain embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA or siRNA molecules may comprise DNA or atypical or non-naturally occurring residues, for example, but not limited to, phosphorothioate residues. The RNA molecules can be expressed from a vector or produced chemically or synthetically. Methods for selecting an appropriate dsRNA or dsRNA-encoding vector are well known in the art for genes whose sequence is known (e.g., see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and PCT Patent Application Nos. WO 2001/036646, WO 1999/032619 and WO 2001/068836).

In certain embodiments, treatment using a modified virus can be used alone or in combination with one or immunomodulatory agents. An immunomodulatory agent can include any compound, molecule or substance capable of suppressing antiviral immunity associated with a tumor or cancer. In certain embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and 1FNy, and chemokines, such as MIP-1, MCP-1 and IL-8. In certain embodiments, the immunomodulatory agent includes immune checkpoint inhibitors such as, but not limited to, anti-CTLA4, anti-PD-1, anti-PDL1 and TLR agonists (e.g., Poly 1:C).

In certain examples, where the further therapy is radiation exemplary doses can be 5,000 Rads (50 Gy) to 100,000 Rads (1000 Gy), or 50,000 Rads (500 Gy), or other appropriate doses within the recited ranges. Alternatively, the radiation dose can be about 30 to 60 Gy, about 40 to about 50 Gy, about 40 to 48 Gy, or about 44 Gy, or other appropriate doses within the recited ranges, with the dose determined, example, by means of a dosimetry study as described above.

"Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents can include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamtin®), vinblastine (Velban®), vincristine (Oncovin®), and vinorelbine (Navelbine®), Ibrutinib, idelalisib, and brentuximab vedotin.

Exemplary alkylating agents can include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids can include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

"In combination with," as used herein, means that the modified virus, such as an oncolytic vaccinia virus as described herein or a pharmaceutical composition comprising the same, and the further therapy, such as a further therapy comprising one or more agents are administered to a subject as part of a treatment regimen or plan. In certain embodiments, being used in combination does not require that the modified virus and the one or more agents are physically combined prior to administration or that they be administered over the same time frame. For example, and not by way of limitation, the modified virus and the one or more agents can be administered concurrently to the subject being treated, or can be administered at the same time or sequentially in any order or at different points in time.

The further therapy can be administered, in various embodiments, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain embodiments, the further therapy is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the further therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months).

In certain embodiments, a method of treating a subject having a cancer includes administering, to the subject, an effective amount of a modified virus, e.g., vaccinia virus, comprising one or more exogenous nucleic acid(s) that encode a protein that modulates the activity of STAT3. For example, and not by way of limitation, a method of treating a subject having a cancer includes administering, to the subject, an effective amount of a modified virus, e.g., vaccinia virus, comprising one or more exogenous nucleic acid(s) that encode a protein that inhibits, reduces and/or minimizes STAT3 activity. In certain embodiments, the vaccinia virus for use in the discloses methods comprises a exogenous nucleic acid that encodes a PIAS3 protein or fragment thereof, a SOCS3 protein or fragment thereof, a TCPTP protein or fragment thereof and/or a dominant-negative mutant STAT3 protein. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a PIAS3 protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 1-7 and 24-27 and conservative substitutions thereof, e.g., SEQ ID NO: 1 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 8-10 and 40-43. In certain embodiments, the PIAS3 protein can be further conjugated to a cell penetrating peptide, as disclosed herein, and the exogenous nucleic acid can further encode a cell penetrating peptide. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a SOCS3 protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 28 and 30 and conservative substitutions thereof, e.g., SEQ ID NO: 28 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 29 and 31. In certain embodiments, the SOCS3 protein can be further conjugated to a cell penetrating peptide, as disclosed herein, and the exogenous nucleic acid can further encode a cell penetrating peptide. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a TCPTP protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 32 and 34 and conservative substitutions thereof, e.g., SEQ ID NO: 32 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 33 and 35. In certain embodiments, the TCPTP protein can be further conjugated to a cell penetrating peptide, as disclosed herein, and the exogenous nucleic acid can further encode a cell penetrating peptide. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a dominant-negative mutant STAT3 protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 36 and 38 and conservative substitutions thereof, e.g., SEQ ID NO: 36 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 37 and 39. In certain embodiments, the dominant-negative mutant STAT3 protein can be further conjugated to a cell penetrating peptide, as disclosed herein, and the exogenous nucleic acid can further encode a cell penetrating peptide.

Kits

The present disclosure further provides kits that comprise one or more of the disclosed oncolytic viruses described herein. In embodiments, this disclosure provides for a kit for administering a modified virus as described herein. In certain embodiments, a kit of this disclosure can include a modified virus or a pharmaceutical composition comprising a modified virus as described above. In certain embodiments, a kit of this disclosure can further include one or more components such as instructions for use, devices and additional reagents, and components, such as tubes, containers and syringes for performing the methods disclosed above. In certain embodiments, a kit of this disclosure can further include one or more agents, e.g., anti-cancer agents, STAT3 inhibitors and/or immunomodulatory agents, that can be administered in combination with a modified virus.

In certain embodiments, a kit of this disclosure can comprise one or more containers containing a modified virus, disclosed herein. For example, and not by way of limitation, a kit of this disclosure can comprise one or more containers that contain a modified vaccinia virus expressing one or more of a PIAS3 protein or a fragment thereof, a SOCS3 protein or a fragment thereof, a TCPTP protein or a fragment thereof, a dominant-negative mutant STAT3 protein or fragment thereof or any combinations thereof. In certain embodiments, the protein that modulates STAT3 activity can be conjugated to a cell penetrating peptide.

In certain embodiments, a kit of this disclosure can include an effective amount of a modified vaccinia virus comprising one or more nucleic acids that encode a PIAS3 protein that can comprise an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 1-7 and 24-27 and conservative substitutions thereof. In certain embodiments, a kit of this disclosure can include a modified vaccinia virus comprising one or more nucleic acids that encode a PIAS3 protein having the amino acid sequence of SEQ ID NO: 1 or a fragment thereof, e.g., amino acids of 133-316, 129-316, 126-176, 132-177 or 400-528 of SEQ ID NO: 1.

In certain embodiments, a kit of this disclosure can include an effective amount of a modified vaccinia virus comprising one or more nucleic acids that can encode a SOCS3 protein comprising an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 28 and 30 and conservative substitutions thereof. In certain embodiments, a kit of this disclosure can include a modified vaccinia virus comprising one or more nucleic acids that encode a SOCS3 protein having the amino acid sequence of SEQ ID NO: 28 or a fragment thereof.

In certain embodiments, a kit of this disclosure can include an effective amount of a modified vaccinia virus comprising one or more nucleic acids that encode a TCPTP protein, e.g., a TCPTP isoform 2 protein, comprising an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 32 and 34 and conservative substitutions thereof. In certain embodiments, a kit of this disclosure can include a modified vaccinia virus comprising one or more nucleic acids that can encode a TCPTP protein having the amino acid sequence of SEQ ID NO: 32 or a fragment thereof.

In certain embodiments, a kit of this disclosure can include an effective amount of a modified vaccinia virus comprising one or more nucleic acids that can encode a dominant-negative mutant STAT3 protein comprising an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 36 and 38 and conservative substitutions thereof. In certain embodiments, a kit of this disclosure can include a modified vaccinia virus comprising one or more nucleic acids that can encode a dominant-negative mutant STAT3 protein having the amino acid sequence of SEQ ID NO: 36 or a fragment thereof.

In certain embodiments, a kit of this disclosure can include instructions for use, a device for administering the modified virus to a subject, or a device for administering an additional agent or compound to a subject. For example, and not by way of limitation, the instructions can include a description of the modified virus and, optionally, other components included in the kit, and methods for administration, including methods for determining the proper state of the subject, the proper dosage amount and the proper administration method for administering the modified virus. Instructions can also include guidance for monitoring the subject over duration of the treatment time.

In certain embodiments, a kit of this disclosure can include a device for administering the modified virus to a subject. Any of a variety of devices known in the art for administering medications and pharmaceutical compositions can be included in the kits provided herein. For example, and not by way of limitation, such devices include, a hypodermic needle, an intravenous needle, a catheter, a needle-less injection device, an inhaler and a liquid dispenser, such as an eyedropper. In certain embodiments, a modified virus to be delivered systemically, for example, by intravenous injection, can be included in a kit with a hypodermic needle and syringe.

EXAMPLES

The examples below further illustrate the described embodiments without limiting the scope of this disclosure.

Example 1: PIAS3 Blocks STAT3 Function

As shown in FIG. 1, human PIAS3 is a 628 amino acid protein that includes a PINIT domain, which includes amino acids 133-316. The PINIT domain includes a PINIT fragment that includes amino acids 132-177.

An exemplary oncolytic virus expressing a PIAS3 protein or a fragment thereof was prepared as follows: human PIAS3 DNA was obtained by reverse transcription PCR on mRNA derived from a buccal cell swab. Full-length PIAS3, segment 133-316, or segment 132-177 was cloned into a vector containing a luciferase reporter and flanking regions with segments of the vaccinia virus TK gene. Vectors varied by the type of PIAS3 construct, the viral promoter, and the inclusion or exclusion of an HIV TAT-derived or other cell-penetrating peptide sequence linked to the PIAS3 sequence. The different PIAS3 constructs were as follows: full-length PIAS3 gene, $PIAS3_{133-316}$+TAT with P11 promoter (DCP), $PIAS3_{133-316}$+TAT with P7.5 promoter (DC7), $PIAS3_{133-316}$ with P11 promoter (DNP), $PIAS3_{133-316}$ with P7.5 promoter (DN7), PIAS3$_{132-177}$+TAT with P11 promoter (FCP), PIAS3$_{132-177}$+TAT with P7.5 promoter (FC7), PIAS3$_{132-177}$ with P11 promoter (FNP) and PIAS3$_{132-177}$ with P7.5 promoter (FN7). Vectors were then transfected into the green monkey kidney epithelial cell line CV-1, which were simultaneously infected with the Western Reserve strain of wildtype vaccinia virus. Transfection and infection of these cells resulted in non-homologous recombination between the TK sites in the vector which replaced the TK gene in the vaccinia genome with one of the PIAS3 constructs and luciferase reporter. PIAS3-expressing vaccinia virus was selected by six rounds of luciferase-positive viral plaque purification and verified by DNA sequencing.

Figure 2:
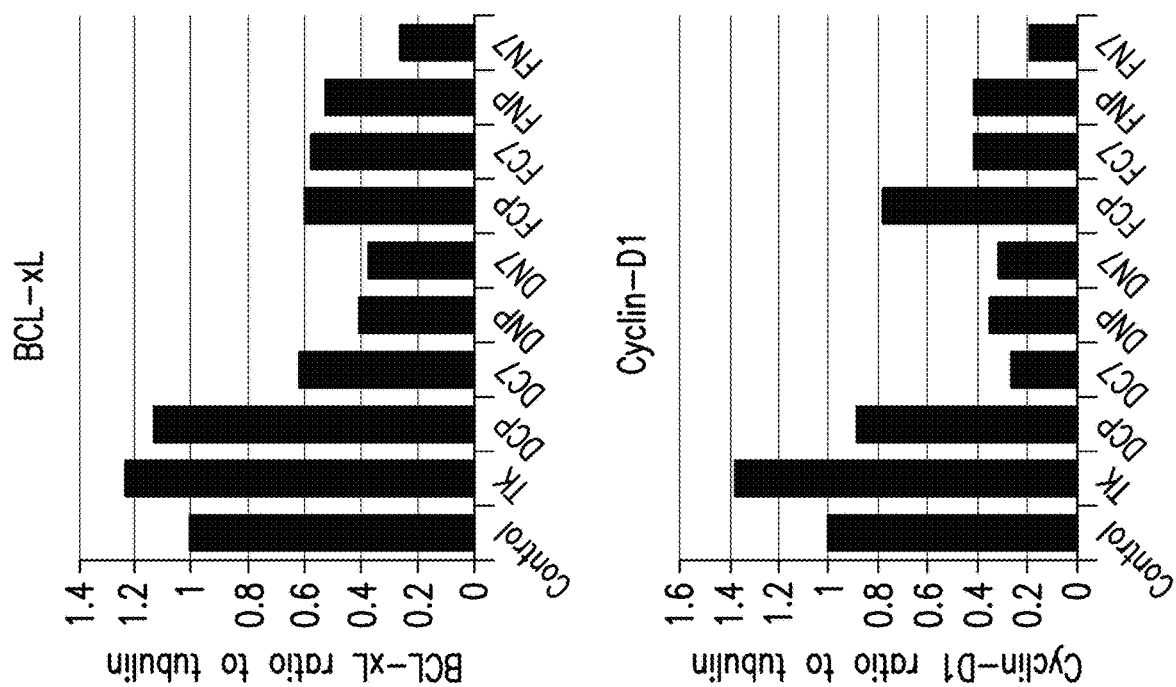
FIG. 2 shows that STAT3 blocking function of different vaccinia virus constructs expressing PIAS3.
Figure 2:
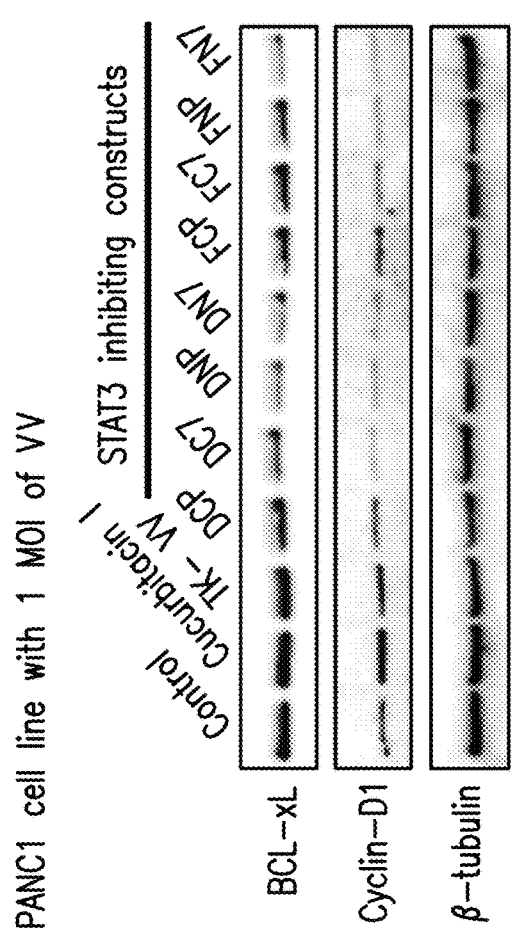
Figure 2:
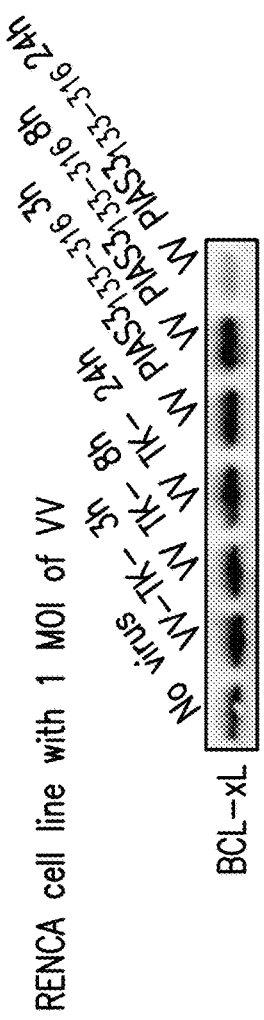

The ability of vaccinia viruses expressing PIAS3, the PINIT domain or the PINIT fragment to block STAT3 activity were analyzed in the human epithelioid carcinoma cell line, PANC1, and the mouse renal cortical adenocarcinoma cell line, RENCA, by determining the expression levels of STAT3 regulated proteins. The Western Reserve vaccinia strain was obtained from BEI Resources (Manassas, Va.), and all recombinant vaccinia viruses used or constructed were based on this strain. The expression levels of STAT3 regulated proteins, BCL-xL and Cyclin-D1, were analyzed upon treatment with the STAT3 inhibiting constructs or vaccinia virus expressing amino acids 133-316 of human PIAS3. As shown in FIG. 2, the STAT3 inhibiting constructs and the vaccinia virus expressing amino acids 133-316 of human PIAS3 reduced the expression of BCL-xL and Cyclin-D1 as compared to the TK-vaccinia virus control, which did not express PIAS3 constructs.

Example 2: Expression of PIAS3 Enhances Cell Death of Cancer Cells

To test the effect the expression of PIAS3 has on human tumor cell lines, the renal cell carcinoma cell line, RCC4, the pancreatic adenocarcinoma epithelial cell line, PL45, the pancreatic epithelioid carcinoma cell line, PANC1, and the renal cortical adenocarcinoma cell line, RENCA, were infected with vaccinia virus expressing PIAS3 or PIAS3 domains and the viability of such cells were monitored over time. To measure cell viability, an MTS assay (CELLTITER 96® AQueous Non-Radioactive Cell Proliferation Assay, Promega) was performed on cells each day for 1 week post-infection.

Figure 3:
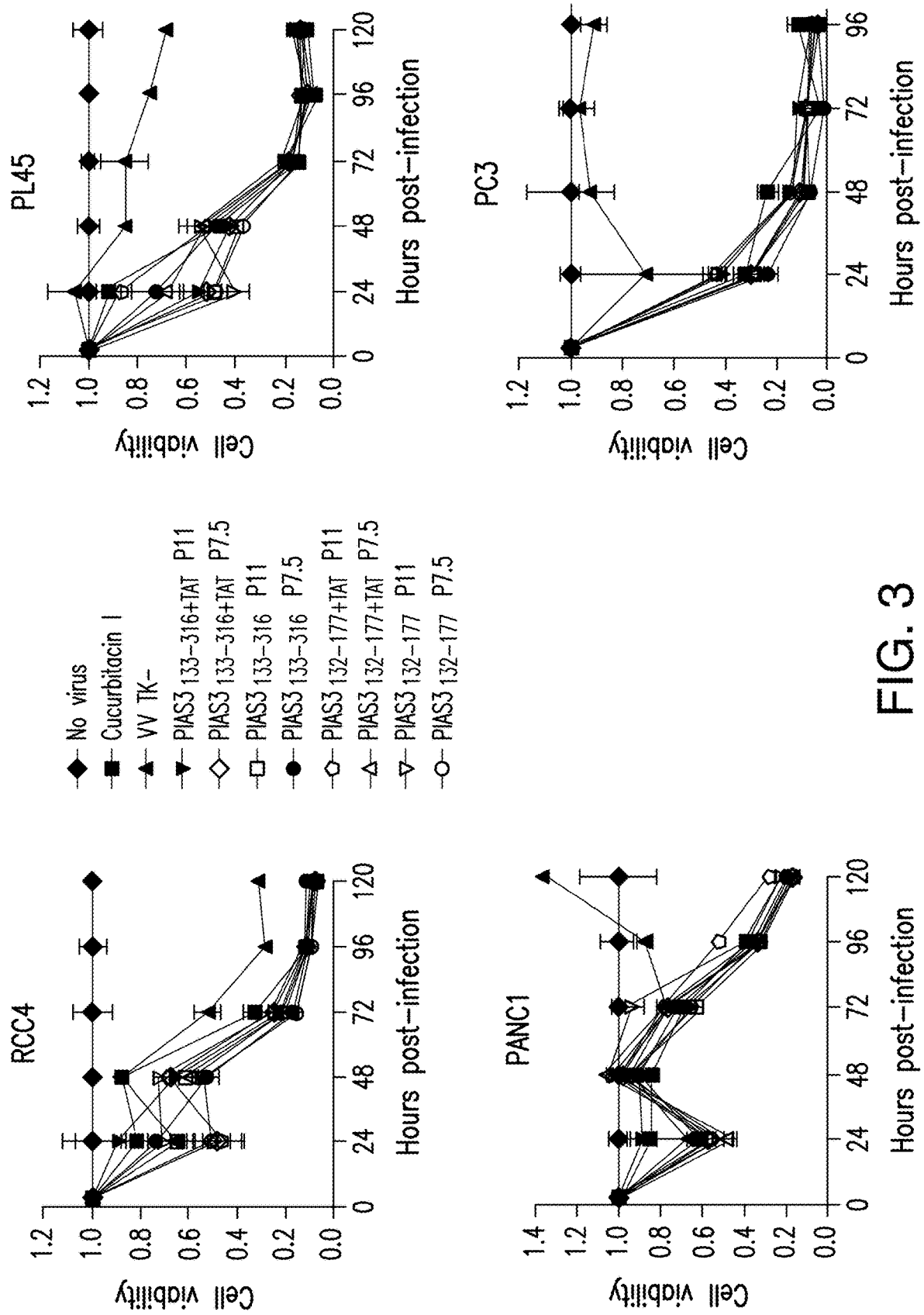
FIG. 3 shows that the expression of PIAS3 or domains of PIAS3 enhances vaccinia-mediated killing of human tumor cell lines.
Figure 4:
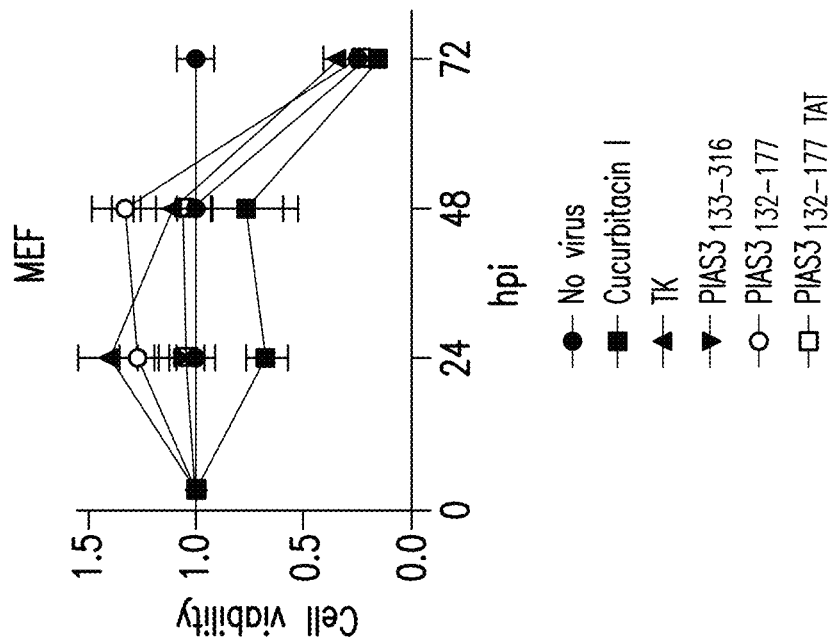
FIG. 4 shows that there is no additional killing was observed in normal cell lines using the vaccinia viruses expressing PIAS3.
Figure 4:
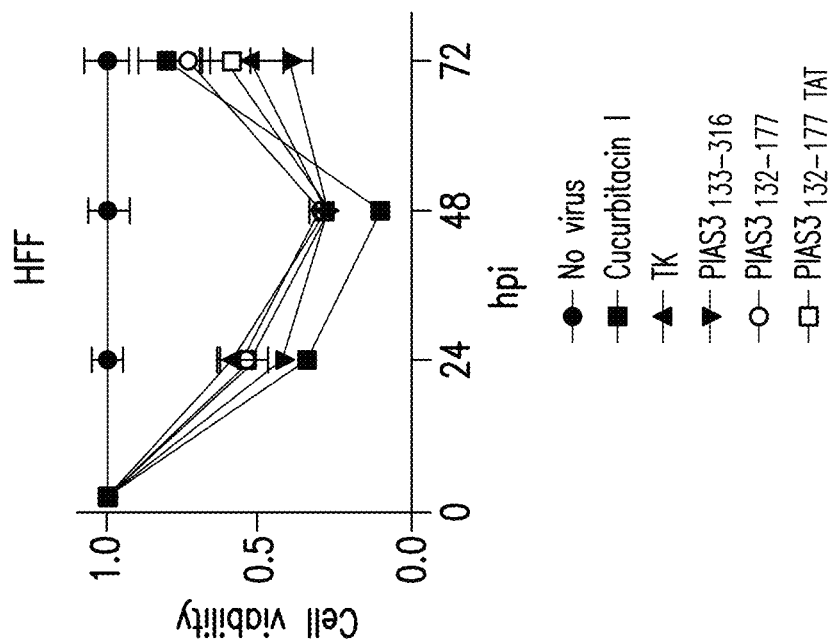

As shown in FIG. 3, the expression of PIAS3 enhanced vaccinia virus-mediated killing of the human tumor cell lines as compared to the control and the STAT3 inhibitor, cucurbitacin I. In addition, as shown in FIG. 4, no additional killing by the PIAS3-expressing vaccinia viruses was observed in normal cell lines, e.g., human foreskin fibroblasts (HFFs) and mouse embryonic fibroblasts (MEFs) as compared to the control. In particular, vaccinia viruses that express PIAS3 or a fragment thereof, e.g., PIAS$_{133-316}$, PIAS$_{132-177}$ or PIAS$_{132-177\ TAT}$, exhibited less toxicity than cucurbitacin I.

Figure 5:
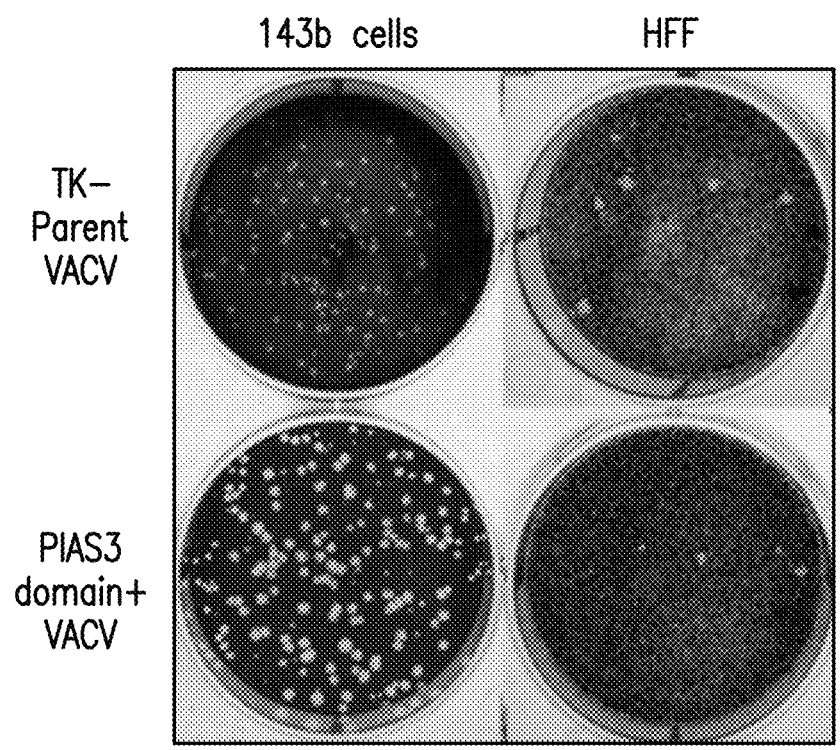
FIG. 5 shows that the expression of PIAS3 domains increases viral plaque size in tumor cells (143b) but not in normal cells (HFF).

In addition, as shown in FIG. 5, infection with the vaccinia virus expressing PIAS$_{133-316}$ resulted in increased plaque size in the osteosarcoma tumor cell line, 143b, as compared to the normal cell line, HFF. Larger plaque size can be interpreted as an enhancement of viral replication and/or enhancement of virus spreading.

These results show that the expression of the PINIT domain or the PINIT fragment of PIAS3 is sufficient to promote cancer cell death.

Example 3: Viral Replication is Increased by PIAS3 Expression

Figure 6:
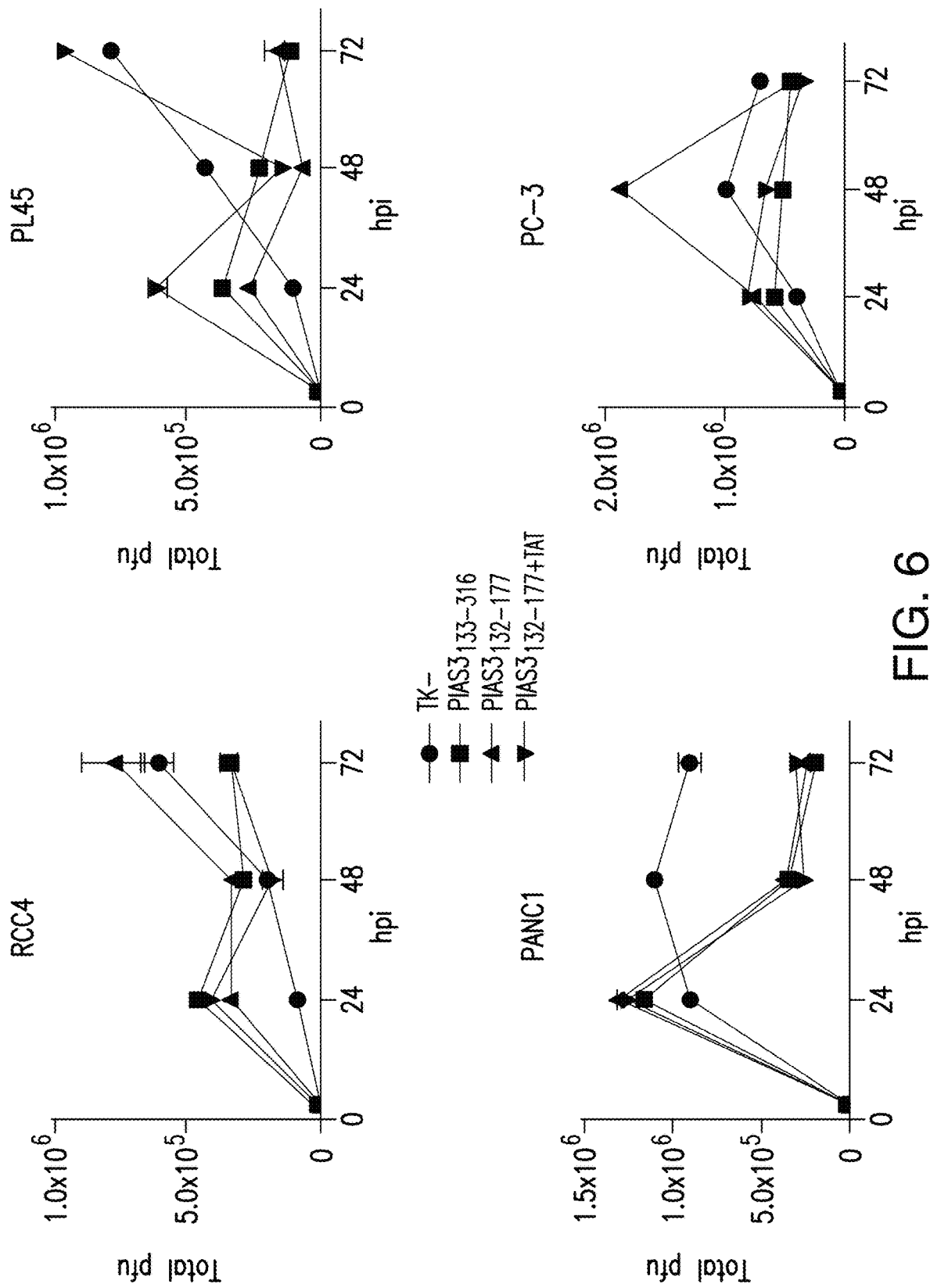
FIG. 6 shows that viral replication is increased in tumor cells when PIAS3 or domains of PIAS3 are expressed.

To determine if viral replication is affected by PIAS3 expression, the same panel of human tumor cell lines as in Example 2 were infected with vaccinia virus expressing the domains of PIAS3 and the luciferase gene. Viral replication was measured by virus plaque assay and is given as plaque forming units per mL (PFU/mL). As shown in FIG. 6, viral replication was increased in tumor cells by the expression of PIAS$_{133-316}$, PIAS$_{132-177}$ or PIAS$_{132-177\ TAT}$ as compared to viruses that are TK-.

Figure 7:
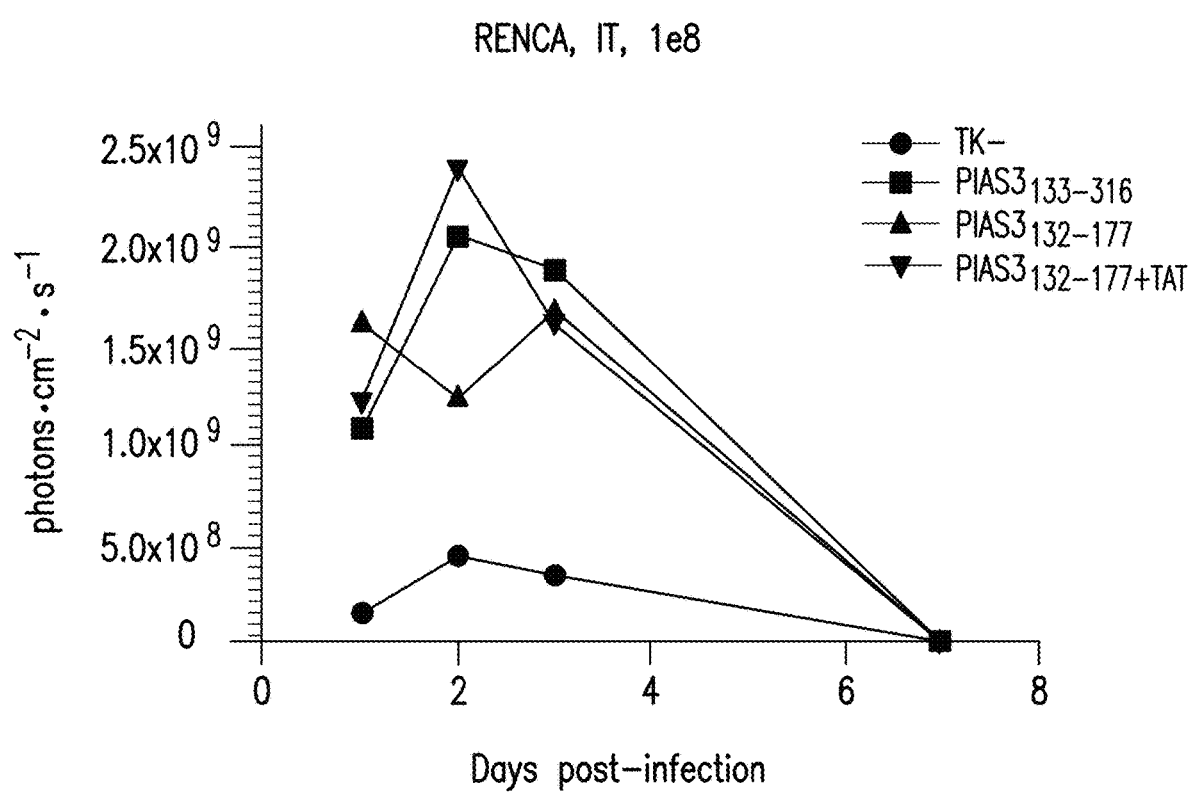
FIG. 7 shows that viral luciferase gene expression (replication) in a tumor is increased when PIAS3 domains are expressed.

Viral gene expression in the tumor was measured by bioluminescence imaging of luciferase expression in vivo. As shown in FIG. 7, in the RENCA tumor model (implanted subcutaneously in BALB/c mice) was injected with single intravenous dose of 1×10$^8$ PFU of the modified vaccinia viruses intratumorally. Viral luciferase expression in the tumor increased when PIAS3 domains were expressed, confirming that viral replication was increased in tumor cells by expression of the PIAS3 domains (FIG. 7). In particular, viral gene expression was increased about 5 to 10 fold by expression of the PIAS3 domains.

Example 4: Expression of PIAS3 Reduced Tumor Volume

Figure 8:
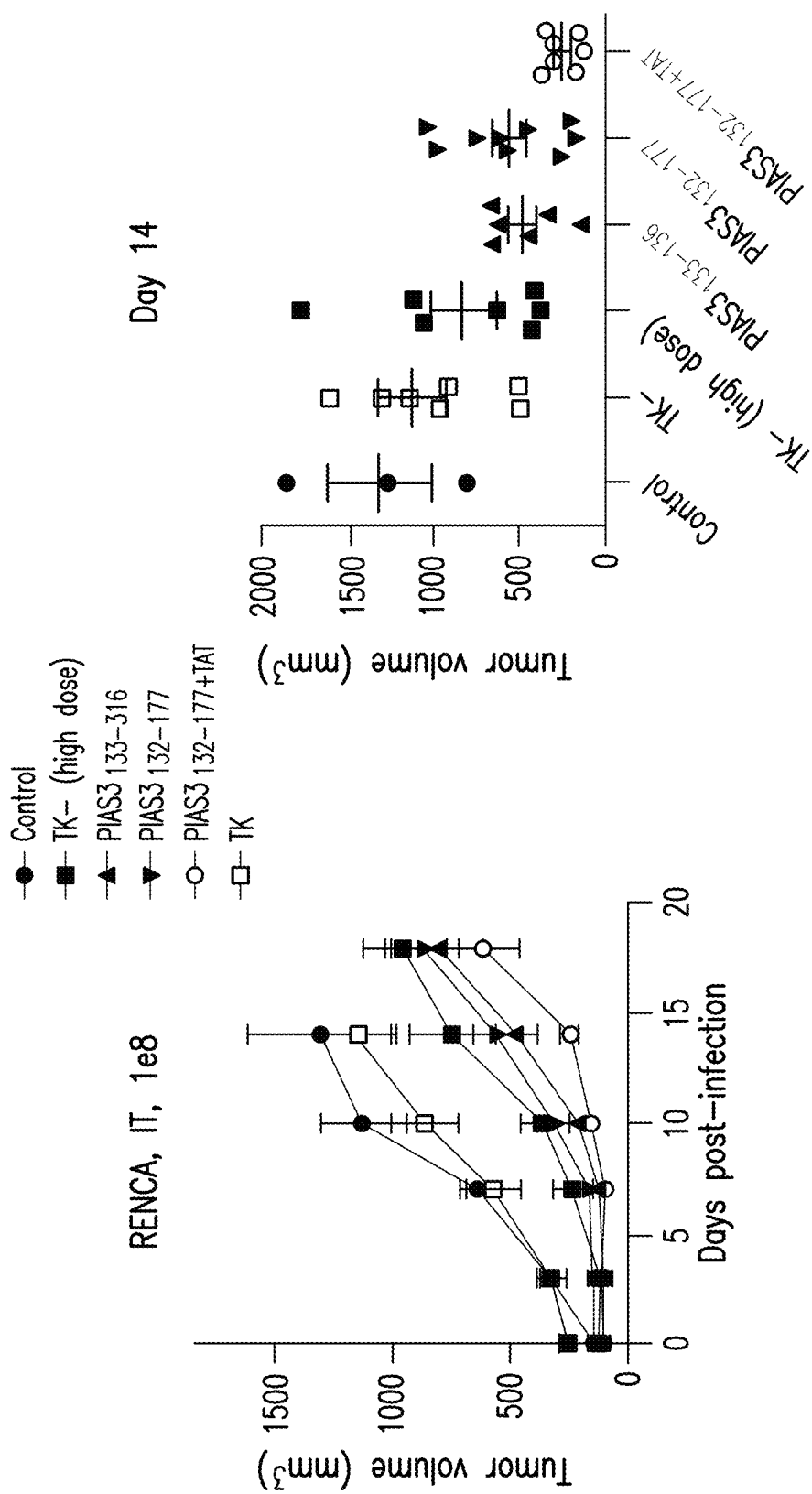
FIG. 8 shows the therapeutic effects of different vaccinia viruses expressing PIAS3 in mouse RENCA tumor models.

To determine if PIAS3 expression affected tumor volumes, tumors generated by the implantation of RENCA cells in BALB/c mice, were treated with vaccinia viruses that express PIAS3 or a fragment thereof, e.g., PIAS$_{133-316}$, PIAS$_{132-177}$ or PIAS$_{132-177\ TAT}$. A single intravenous dose of 1×10$^8$ PFU was administered intratumorally per mouse. For the high dose administration, a single intravenous dose of 5×10$^9$ PFU was administered intratumorally. As shown in FIG. 8, the tumor volume reduced by expression of PIAS$_{133-316}$, PIAS$_{132-177}$ or PIAS$_{132-177\ TAT}$, as compared to the control or the vaccinia virus with the TK deletion.

Figure 9:
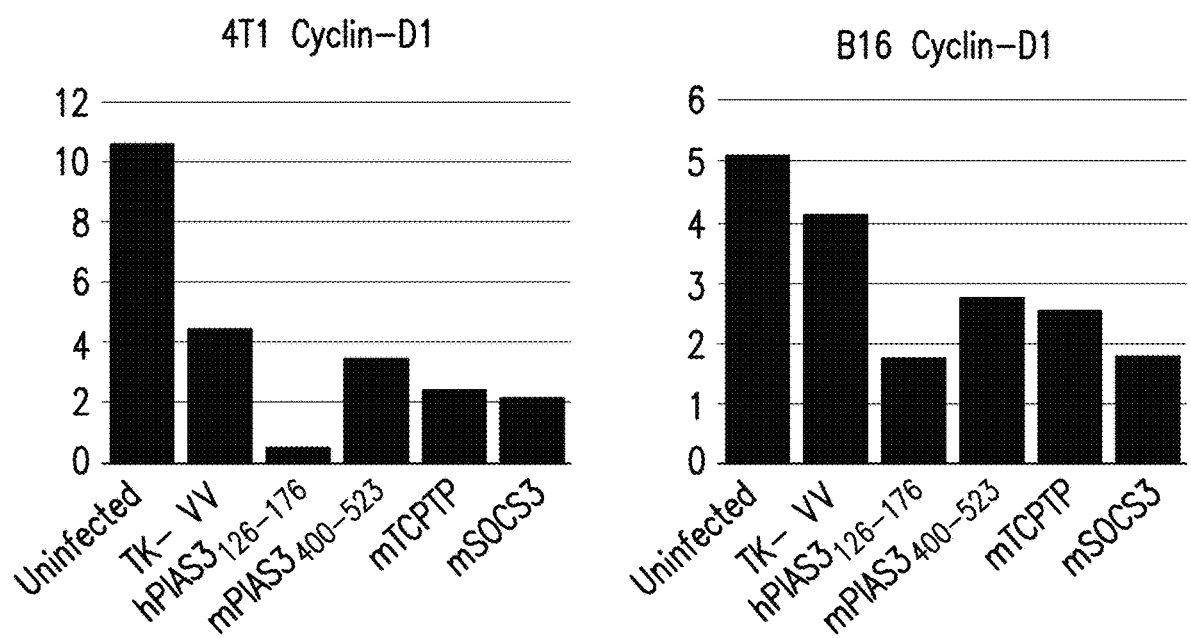
FIG. 9 shows that the expression of vaccinia viruses expressing hPIAS$_{3126\text{-}176}$, mPIAS$_{3400\text{-}523}$, mTCPTP or mSOCS3 resulted in decreased Cyclin D expression in tumor cell lines.

Example 5: Expression of the Acidic Domain of PIAS3 and Expression of TCPTP or SOCS3 Decreased STAT3 Activity To determine if the acidic domain of PIAS3 affected the expression of the downstream target of STAT3, Cyclin D1, 12-well plates of confluent mouse cell lines 4T1 or B16 were infected at 5 MOI with either TK-vaccinia virus or vaccinia viruses expressing hPIAS3$_{126-176}$ or mPIAS3$_{400-523}$. After 18 h, cells were lysed with 2× Laemmli buffer, boiled for 5 minutes, and run on SDS-PAGE for Western blotting. To detect changes in STAT3-regulated genes, membranes were stained with anti-Cyclin D1 or anti-BCL-xL antibodies and compared to control staining of β-tubulin. Results are displayed as the ratio of band intensity of STAT3-regulated genes versus β-tubulin expression. As shown in FIG. 9, the acidic domain of PIAS3 resulted in a decrease in Cyclin D1 expression.

To determine if additional regulators of STAT3 activity can affect expression of cyclin D1, 4T1 or B16 were infected at 5 MO with vaccinia viruses expressing mTCPTP or mSOCS3. As shown in FIG. 9, vaccinia virus expressing mTCPTP and vaccinia virus expressing mSOCS3 resulted in a decrease in Cyclin D1 expression.

Various NCBI accession numbers, publications, patents and patent applications are cited herein, the contents of which are hereby incorporated by reference in their entireties.

The invention claimed is:

1. A virus comprising an exogenous nucleic acid encoding a protein or a fragment thereof that modulates STAT3-mediated gene expression, wherein the protein or the fragment thereof is a PIAS3 protein or a fragment thereof, wherein the virus comprises an oncolytic vaccinia virus.

2. The virus of claim 1, wherein the protein or fragment thereof comprises a STAT3 recognition domain or a blocking fragment within said STAT3 recognition domain.

3. The virus of claim 1, wherein the exogenous nucleic acid comprises a nucleic acid sequence set forth in SEQ ID NO: 8, SEQ ID NO: 9, SEQ ID NO: 10, SEQ ID NO: 40, SEQ ID NO: 41, SEQ ID NO: 42, or SEQ ID NO: 43.

4. The virus of claim 1, wherein the PIAS3 protein or fragment thereof comprises an amino acid sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26, or SEQ ID NO: 27.

5. A virus comprising an exogenous nucleic acid encoding a protein or a fragment thereof that modulates STAT3-mediated gene expression, wherein the protein or the fragment thereof is a PIAS3 protein or a fragment thereof, wherein the exogenous nucleic acid further encodes a cell-penetrating protein.

6. The virus of claim 5, wherein the cell-penetrating protein comprises a TAT protein of HIV-1 or a fragment thereof, a YopM protein or a fragment thereof, a transportan protein or a fragment thereof, a penetratin or a fragment thereof, a poly-arginine, or a combination thereof.

7. A pharmaceutical composition comprising the virus of claim 1, and an excipient.

8. A pharmaceutical composition comprising the virus of claim 5, and an excipient.

9. The virus of claim 5, wherein the virus comprises an oncolytic vaccinia virus.

10. The virus of claim 5, wherein the protein or fragment thereof comprises a STAT3 recognition domain or a blocking fragment within said STAT3 recognition domain.

11. The virus of claim 5, wherein the exogenous nucleic acid comprises a nucleic acid sequence set forth in SEQ ID NO: 8, SEQ ID NO: 9, SEQ ID NO: 10, SEQ ID NO: 40, SEQ ID NO: 41, SEQ ID NO: 42, or SEQ ID NO: 43.

12. The virus of claim 5, wherein the PIAS3 protein or fragment thereof comprises an amino acid sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26, or SEQ ID NO: 27.

13. The virus of claim 5, wherein the PIAS3 protein or fragment thereof comprises the amino acid sequence set forth in SEQ ID NO: 2.

14. The virus of claim 5, wherein the PIAS3 protein or fragment thereof comprises the amino acid sequence set forth in SEQ ID NO: 3.

15. The virus of claim 5, wherein the PIAS3 protein or fragment thereof comprises the amino acid sequence set forth in SEQ ID NO: 24.

16. The virus of claim 1, wherein the exogenous nucleic acid further encodes a cell-penetrating protein.

17. The virus of claim 1, wherein the cell-penetrating protein comprises a TAT protein of HIV-1 or a fragment thereof, a YopM protein or a fragment thereof, a transportan protein or a fragment thereof, a penetratin or a fragment thereof, a poly-arginine, or a combination thereof.

18. The virus of claim 1, wherein the PIAS3 protein or fragment thereof comprises the amino acid sequence set forth in SEQ ID NO: 2.

19. The virus of claim 1, wherein the PIAS3 protein or fragment thereof comprises the amino acid sequence set forth in SEQ ID NO: 3.

20. The virus of claim 1, wherein the PIAS3 protein or fragment thereof comprises the amino acid sequence set forth in SEQ ID NO: 24.

* * * * *